United States Patent
Williams et al.

(10) Patent No.: US 9,322,025 B2
(45) Date of Patent: Apr. 26, 2016

(54) METHODS AND DNA CONSTRUCTS FOR HIGH YIELD PRODUCTION OF POLYPEPTIDES

(75) Inventors: James A. Williams, Lincoln, NE (US); Peng Luan, Fishers, IN (US); Yuannan Xia, Lincoln, NE (US); Scott Harley, Pensacola, FL (US)

(73) Assignee: Medtronic, Inc., Minneapolis, MN (US)

( * ) Notice: Subject to any disclaimer, the term of this patent is extended or adjusted under 35 U.S.C. 154(b) by 821 days.

(21) Appl. No.: 12/358,966

(22) Filed: Jan. 23, 2009

(65) Prior Publication Data

US 2009/0170192 A1 Jul. 2, 2009

Related U.S. Application Data

(60) Division of application No. 10/997,078, filed on Nov. 24, 2004, now Pat. No. 7,501,484, which is a continuation of application No. PCT/US03/16643, filed on May 23, 2003.

(60) Provisional application No. 60/383,370, filed on May 24, 2002.

(51) Int. Cl.
| | |
|---|---|
| C07H 21/04 | (2006.01) |
| C12N 5/10 | (2006.01) |
| C07K 19/00 | (2006.01) |
| C12N 15/63 | (2006.01) |
| C07K 14/60 | (2006.01) |
| C07K 14/605 | (2006.01) |
| C07K 14/635 | (2006.01) |

(52) U.S. Cl.
CPC ............. *C12N 15/63* (2013.01); *C07K 14/60* (2013.01); *C07K 14/605* (2013.01); *C07K 14/635* (2013.01); *C07K 2319/50* (2013.01)

(58) Field of Classification Search
None
See application file for complete search history.

(56) References Cited

U.S. PATENT DOCUMENTS

| | | | | |
|---|---|---|---|---|
| 5,352,771 | A | * | 10/1994 | Kostic et al. ................. 530/345 |
| 5,741,673 | A | * | 4/1998 | Montminy et al. .......... 435/69.1 |
| 5,814,603 | A | | 9/1998 | Oldenburg et al. |
| 6,265,540 | B1 | * | 7/2001 | Isaacs et al. ................. 530/326 |
| 6,313,092 | B1 | | 11/2001 | Holladay et al. |
| 6,703,484 | B2 | | 3/2004 | Chatterjee |
| 7,271,149 | B2 | * | 9/2007 | Glaesner et al. .............. 514/7.2 |

FOREIGN PATENT DOCUMENTS

WO    WO 93/17110    *   9/1993

OTHER PUBLICATIONS

Capone et al, Amber, ochre and opal suppressor tRNA genes derived from a human serine tRNA gene, The EMBO Journal, 1985, vol. 4(1), pp. 213-222.*
Lee, J.H., et al., "Enhanced Expression of Tandem Multimers of the Antimicrobial Peptide Buforin II in *Escherichia coli* by the DEAD-box Protein and trxB Mutant", Appl. Microbiol. Biotechnol., 58(6), May 2002, 790-6.
Simmonds, A.J. et al., "Molecular Interactions Between Vestigial and Scalloped Promote Wing Formation in Drosophia", Genes Dev. 12(24), Dec. 15, 1998, 3815-20.
Williams, J.A. et al., "Control of *Drosophila* Wing and Haltere Development by the Nuclear Vestigial Gene Product", Genes Dev. 5(12b), Dec. 1991, 2481-2495.
Smith et al., "Surface Point Mutations that Significantly Alter the Structure and Stability of a Protein's Denatured State", Protein Science 1996, vol. 5, pp. 2009-2019.
Gi:228521, Williams et al., Vestigial Gene, U.S. National Library of Medicine, Bethesda, MD, USA, Nov. 20, 1996, accessed by the PTO on Mar. 22, 2007.
Tertiary Structures—Biology pages, downloaded Oct. 14, 2005.

* cited by examiner

*Primary Examiner* — Maria Marvich
(74) *Attorney, Agent, or Firm* — Mueting, Raasch & Gebhardt, P.A.

(57) ABSTRACT

The invention provides an inclusion body fusion partner to increase peptide and polypeptide production in a cell.

31 Claims, 20 Drawing Sheets

```
|←————————— Leader sequence —————————————|
                                                BamHI
ATG GCT AGC ATG ACT GGT GGA CAG CAA ATG GGT CGC GGA TCC GGC
CAG GGA
 M   A   S   M   T   G   G   Q   Q   M   G   R   G   S   G
 Q   G
 1
             17
```

```
←——————————— Vg gene sequence ———————————————→

CAG GCT CAA TAT CTA GCG GCC TCC TTG GTT GTG TTC ACC AAC TAC
TCG GGC
 Q   A   Q   Y   L   A   A   S   L   V   V   F   T   N   Y
 S   G
 18
             34          Hydrophobic core (bold)
```

```
←——————————————————|←——————————— Linker sequence ——————→
                   HpaI
GAC ACG GCC AGC CAG GTG GAC GTT AAC GGT CCG CGT GCT ATG GTC
GAC GAC
 D   T   A   S   Q   V   D   V   N   G   P   R   A   M   V
 D   D
 35
             51
```

```
←——————————————————|————————————————————————————→

GAC GAC AAA TGC CAC TAC GCT GAC GCT ATC TTC ACC AAC TCT TAC
CGT AAA
 D   D   K   C   H ↑ Y   A   D   A   I   F   T   N   S   Y
 R   K
 52         55  56  57
             68
```

Fig. 3A

←──────────── GRF(1-44)A sequence ────────────→

GTT CTG GGT CAG CTG TCT GCT CGT AAA CTG CTG CAG GAC ATC ATG
TCC CGT
 V   L   G   Q   L   S   A   R   K   L   L   Q   D   I   M
 S   R
 69
     85

←────────────────────────────────────────────────|

CAG CAG GGT GAA TCT AAC CAG GAA CGT GGT GCT CGT GCT CGT CTG
GCA TAA
 Q   Q   G   E   S   N   Q   E   R   G   A   R   A   R   L
 A   **
 86
     101 STOP

XhoI
<u>CTC GAG</u>

Amino acid sequence is: SEQ ID NO: 120
Nucleic acid sequence is: SEQ ID NO: 121

*Fig. 3B*

```
                                                T7tag                         Bam HI          EcoRI
ATG GCT AGC ATG ACT GGT GGA CAG CAA ATG GGT CGC GGA TCC GAA TTC TCC
 M   A   S   M   T   G   G   Q   Q   M   G   R   G   S   E   F   S HpaI            Linker             SalI
TTC GTT AAC GGT CCG CGT GCT ATG GTC GAC GAC GAC GAC AAG CAC
 F   V   N   G   P   R   A   M   V   D   D   D   D   K   ↓
                                                        Enterokinase GRF(1-44)A
TAC GCT GAC GCT ATC TTC ACC AAC TCT TAC CGT AAA
 Y   A   D   A   I   F   T   N   S   Y   R   K GTT CTG GGT CAG CTG TCT GCT CGT AAA CTG CTG CAG GAC ATC ATG TCC CGT
 V   L   G   Q   L   S   A   R   K   L   L   Q   D   I   M   S   R CAG CAG GGT GAA TCT AAC CAG GAA CGT GGT GCT CGT GCT CGT CTG GCA TAA
 Q   Q   G   E   S   N   Q   E   R   G   A   R   A   R   L   A   **

EcoRV/HincII                XhoI
GAT GAC AAG CTT GCG GCC GCA CTC GAG

Amino acid sequence is: SEQ ID NO: 122
Nucleic acid sequence is: SEQ ID NO: 123
```

Fig. 4

|←—————————— Leader sequence ——————————|←————→

ATG GCT AGC ATG ACT GGT GGA CAG CAA ATG GGT CGC GGA TCC GGC
CAG GGA
 M   A   S   M   T   G   G   Q   Q   M   G   R   S   G
 Q   G
 1
     17

←—————————————— Vg gene sequence ——————————————→

CAG GCT CAA TAT CTA GCG GCC TCC TTG GTT GTG TTC ACC AAC TAC
TCG GGC
 Q   A   Q   Y   L   A   A   S   L   V   V   F   T   N   Y
 S   G
 18
     34

←————————————————|←————————— Linker sequence —————————→

GAC ACG GCC AGC CAG GTG GAC GTT AAC GGT CCG CGT GCT ATG GTC
GAC GAC
 D   T   A   S   Q   V   D   V   N   G   P   R   A   M   V
 D   D
 35
     51

←——————|←——————————————————————————————→

GAC GAC AAA TAC GCT GAC GCT ATC TTC ACC AAC TCT TAC CGT
AAA
 D   D   K   Y   A   D   A   I   F   T   N   S   Y   R   K
 52  53  54  55
 66

*Fig. 5A*

```
<—————————————— GRF(1-44)A sequence ——————————————>
GTT CTG GGT CAG CTG TCT GCT CGT AAA CTG CTG CAG GAC ATC ATG
TCC CGT
 V   L   G   Q   L   S   A   R   K   L   L   Q   D   I   M
 S   R
 67
     83

<——————————————————————————————————————————————|
CAG CAG GGT GAA TCT AAC CAG GAA CGT GGT GCT CGT GCT CGT CTG
GCA TAA
 Q   Q   G   E   S   N   Q   E   R   G   A   R   A   R   L
 A   **
 84
     99 STOP

EcoRV/HincII                            XhoI
GAT GAC AAG CTT GCG GCC GCA CTC GAG Amino acid sequence is: SEQ ID NO: 124
Nucleic acid sequence is: SEQ ID NO: 125
```

*Fig. 5B*

```
5'
ATG GCT AGC ATG ACT GGT GGA CAG CAA ATG GGT CGC GGA TCC GGC CAG GGT CAG
 M   A   S   M   T   G   G   Q   Q   M   G   R   G   S   G   Q   G   Q
         9              18          27          36          45      54

GCT CAA TAT CTG GCG TCC CTG GTT GTG TTC ACC AAC TAC TCG GGC GAC ACG
 A   Q   Y   L   A   S   L   V   V   F   T   N   Y   S   G   D   T
     63              72          81          90          99      108

GCC AGC GTG CAG GAC AAC GGT GTT GAC AAC GGT CCG CGT GCT ATG GTC GAC GAC GAC AAA
 A   S   V   Q   D   N   G   V   D   N   G   P   R   A   M   V   D   D   D   K
     117             126         135         Sall 144     153         162

TGC CAC TAC GCT GAC GCT ATC TTC ACC AAC TCT TAC CGT AAA GTT CTG GGT CAG
 C   H   Y   A   D   A   I   F   T   N   S   Y   R   K   V   L   G   Q
     171             180         189         198         207     216

CTG TCT GCT CGT AAA CTG CTG CAG GAC ATC ATG TCC CGT CAG CAG GGT GAA TCT
 L   S   A   R   K   L   L   Q   D   I   M   S   R   Q   Q   G   E   S
     225             234         243         252         261     270

AAC CAG GAA CGT GGT GCT CGT CGT CTG GCA TAA CTC GAG 3'
 N   Q   E   R   G   A   R   R   L   A   *   L   E
     279             288         297     306

Amino acid sequence is: SEQ ID NO: 126
Nucleic acid sequence is: SEQ ID NO: 127
```

Fig. 6

```
5'
ATG GCT AGC ATG ACT GGT GGA CAG ATG GGT CGC GGA TCC GGC CAG GGT CAG
 M   A   S   M   T   G   G   Q   M   G   R   G   S   G   Q   G   Q
                                                    BamHI

GCT CAA TAT gac gaa GCT TCC gac GTT TTC ACC AAC TAC TCG GGC GAC ACG
 A   Q   Y   D   E   A   S   D   V   F   T   N   Y   S   G   D   T
               EcoRI GCC AGC CAG GTG GAC GTT AAC GGT CCG CGT GCT ATG GTC GAC GAC GAC AAA
 A   S   Q   V   D   V   N   G   P   R   A   M   V   D   D   D   K TGC CAC TAC GCT GAC GCT ATC TTC ACC AAC TCT TAC CGT AAA GTT CTG GGT CAG
 C   H   Y   A   D   A   I   F   T   N   S   Y   R   K   V   L   G   Q CTG TCT GCT CGT AAA CTG CAG CAG ATC ATG TCC CGT CAG GGT GAA TCT
 L   S   A   R   K   L   Q   Q   I   M   S   R   Q   G   E   S AAC CAG GAA CGT GGT GCT CGT GCT CGT CTG GCA TAA CTC GAG 3'
 N   Q   E   R   G   A   R   A   R   L   A   *   L   E Amino acid sequence is: SEQ ID NO: 128
Nucleic acid sequence is: SEQ ID NO: 129
```

```
5'
ATG GCT AGC ATG ACT GGT GGA CAA ATG GGT CGC GGA TCC GGC CAG GGT CAG
 M   A   S   M   T   G   G   Q   M   G   R   G   S   G   Q   G   Q
             18              27              36              45              54                                 108

GCT CAA TAT CTG ncg GCC TCC CTG GTT maa TTC ACC AAC TAC TCG GGC GAC ACG
 A   Q   Y   L   T   A   S   L   V   K   F   T   N   Y   S   G   D   T
                 P           Q
                 A
                 S
 63              72              81              90              99

GCC AGC CAG GTG GAC GTT AAC GGT CCG CGT GCT ATG GTC GAC GAC GAC AAA
 A   S   Q   V   D   V   N   G   P   R   A   M   V   D   D   D   K
117             126             135             144             153             162

TGC CAC TAC GCT GAC GCT ATC TTC ACC AAC ATG TCT AAA GTT CTG GGT CAG
 C   H   Y   A   D   A   I   F   T   N   M   S   K   V   L   G   Q
171             180             189             198             207             216

CTG TCT GCT CGT AAA CTG CTG CAG GAC ATG TCC CGT CAG CAG CAG GGT GAA TCT
 L   S   A   R   K   L   L   Q   D   M   S   R   Q   Q   Q   G   E   S
225             234             243             252             261             270

AAC CAG GAA CGT GGT GCT CGT CTG GCA TAA CTC GAG 3'
 N   Q   E   R   G   A   R   L   A   *   L   E
279             288             297             306
```

Amino acid sequence is: SEQ ID NO: 130
Nucleic acid sequence is: SEQ ID NO: 131

```
                        9                 18                27           36 BamHI      45    DelI  54
5' ATG GCT AGC ATG ACT GGT GGA CAG ATG GGT CGC GGA TCC(GGC CAG GGT CAG
    M   A   S   M   T   G   G   Q   M   G   R   G   S   G   Q   G   Q
           63                72                81                90                99               108
   GCT)CAA TAT CTG GCT GCC TCC CTG GTT GTG TTC ACC AAC TAC TCG GGC GAC(ACG
    A   Q   Y   L   A   A   S   L   V   V   F   T   N   Y   S   G   D   T
        Del3
   Del2 117           126 HpaI        135 EcoRI     144               153               162
   GCC AGC CAG GTG GAC)GTT AAC(CCG GAA TTC TCT GTT)GGT GGT GGT GGT CCG
    A   S   Q   V   D   V   N   P   E   F   S   V   G   G   G   G   P
          171               180               189               198               207               216
   CGT TCT GTT TCT GAA ATC CAG CTG ATG CAC AAC CTG GGT AAA CAC CTG AAC TCT
    R   S   V   S   E   I   Q   L   M   H   N   L   G   K   H   L   N   S
          225               234               243               252               261               270
   ATG GAA CGT GTT GAA TGG CTG CGT AAA AAA CTG CAG GAC GTT CAC AAC TTC TAA
    M   E   R   V   E   W   L   R   K   K   L   Q   D   V   H   N   F   *
       279 XhoI
   GAT ATC CTC GAG 3'
```

Amino acid sequence is: SEQ ID NO: 132
Nucleic acid sequence is: SEQ ID NO: 133

Fig. 10

```
Hpa1  135 EcoRI     144              153         162
GTT AAC CCG GAA TTC TCT GTT GGT GGT GGT GGT CCG CGT TGC CAC TCT GTT TCT
 V   N   P   E   F   S   V   G   G   G   G   P   R   C   H   S   V   S
   T7tagVg              Linker               Pd Cleavage        PTH
```

Amino acid sequence is: SEQ ID NO: 134
Nucleic acid sequence is: SEQ ID NO: 135

Fig. 11 a) Del 3 leader sequence

```
                      9                18               27              36      BamHI
45                                              54
5' ATG GCT AGC ATG ACT GGT GGA CAG CAA ATG GGT CGC GGA TCC
GGC CAG GGT CAG
    --- --- --- --- --- --- --- --- --- --- --- --- --- ---
--- --- --- ---
    M   A   S   M   T   G   G   Q   Q   M   G   R   G   S
G   Q   G   Q 63               72               81              90
99       108
    GCT CAA TAT CTG GCT GCC TCC CTG GTT GTG TTC ACC AAC TAC
TCG GGC GAC ACG
    --- --- --- --- --- --- --- --- --- --- --- --- --- ---
--- --- --- ---
    A   Q   Y   L   A   A   S   L   V   V   F   T   N   Y
S   G   D   T 117              126 HpaI
    GCC AGC CAG GTG GAC GTT AAC GGT GGT GGT GGT GGT TGC CAC
    --- --- --- --- --- --- --- --- --- --- --- --- --- ---
    A   S   Q   V   D   V   N   G   G   G   G   G   C   H
```

Amino acid: SEQ ID NO: 136 – Nucleic acid: SEQ ID NO: 137 b) Del 2+ 3 leader sequence

```
                      9                18               27              36      BamHI
45                                              54
5' ATG GCT AGC ATG ACT GGT GGA CAG CAA ATG GGT CGC GGA TCC
GGC CAG GGT CAG
    --- --- --- --- --- --- --- --- --- --- --- --- --- ---
--- --- --- ---
    M   A   S   M   T   G   G   Q   Q   M   G   R   G   S
G   Q   G   Q 63               72               81              90
99
    GCT CAA TAT CTG GCT GCC TCC CTG GTT GTG TTC ACC AAC TAC
TCG GGC GAC
    --- --- --- --- --- --- --- --- --- --- --- --- --- ---
--- --- ---
    A   Q   Y   L   A   A   S   L   V   V   F   T   N   Y
S   G   D
```

*Fig. 12*

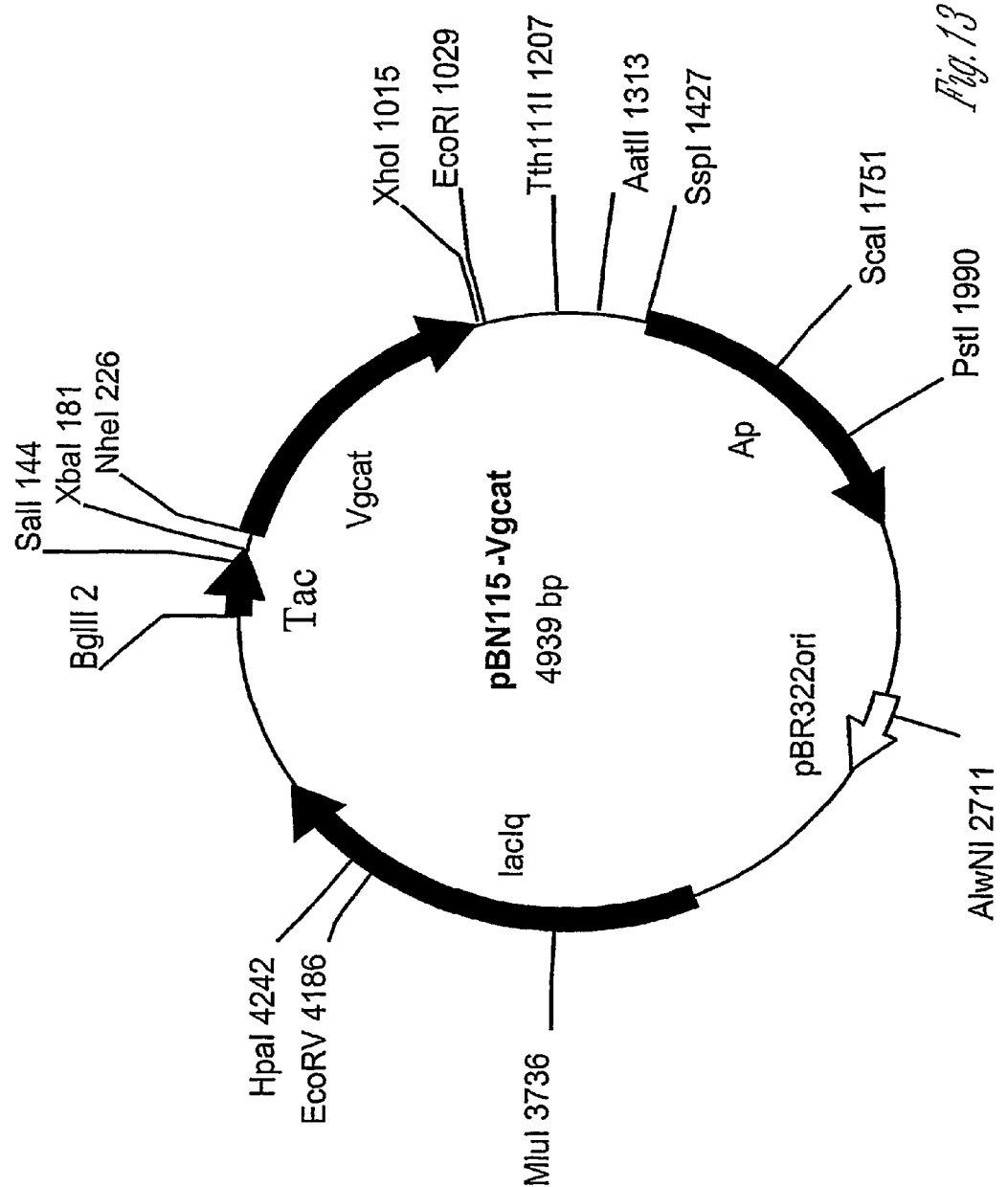

```
         NheI
          9                  18                27                   36                45              54
5' ATG GCT AGC ATG ACT GGT GGA CAG CAA ATG GGT CGC GGA TCC GGC CAG GGT CAG
    M   A   S   M   T   G   G   Q   Q   M   G   R   G   S   G   Q   G   Q 63                  72                81                   90                99             108
   GCT CAA TAT CTG GCT GCC TCC CTG GCT GTT GTG TTC ACC AAC TAC TCG GGC GAC ACG
    A   Q   Y   L   A   A   S   L   A   V   V   F   T   N   Y   S   G   D   T

NheI
        117                 126               135
   GCC AGC CAG GTG GAC GTT AAC GCT AGC GAT
    A   S   Q   V   D   V   N   A   S   D

Amino acid sequence is: SEQ ID NO: 142
Nucleic acid sequence is: SEQ ID NO: 143
```

Fig. 14

```
5' ATG GCT AGC ATG ACT GGT GGA CAG CAA ATG GGT CGC GGA TCC GGC CAG GGT CAG
   M   A   S   M   T   G   G   Q   Q   M   G   R   G   S   G   Q   G   Q
                   9              18              27              36              45              54

GCT CAA TAT CTG GCG GCC TCC CTG GTT GTG TTC ACC AAC TAC TCG GGC GAC ACG
   A   Q   Y   L   A   A   S   L   V   V   F   T   N   Y   S   G   D   T
                   63              72              81              90              99              108

GCC AGC CAG GTG GAC AAC GGT CCG CGT GCT ATG GTC GAC GAC GAC GAC GAC AAA
   A   S   Q   V   D   N   G   P   R   A   M   V   D   D   D   D   D   K
                   117             126             135             144 SalI 153             162

TGC CAT GCT GAA GGT ACC TTC ACC TCC GAC TCC TAC CTG GAA GGT
   C   H   A   E   G   T   F   T   S   D   V   S   S   Y   L   E   G
                   171             180             189             198             207             216

CAG GCT AAA GAA TTC ATC GCT TGG CTG GTT AAA GGT CGT TGC CAC TAA CTC
   Q   A   K   E   F   I   A   W   L   V   K   G   R   C   H   *
                   225             234             243             252             261             270

GAG 3'
```

Amino acid sequence is: SEQ ID NO: 144
Nucleic acid sequence is: SEQ ID NO: 145

Fig. 17

|  | Hydrophobic Core |  |  |
|---|---|---|---|
| GSGQGQAQY | LAASLVVF | TNYSGDTASQVD | (SEQ ID NO: 2) |
| GS-----QY | LAASLVVF | TNYSGDTASQVD | (SEQ ID NO: 3) |
| GSGQGQAQY | LAASLVVF | TNYSGD------ | (SEQ ID NO: 4) |

METHODS AND DNA CONSTRUCTS FOR HIGH YIELD PRODUCTION OF POLYPEPTIDES

CROSS-REFERENCE TO RELATED APPLICATIONS

This application is a divisional application of U.S. patent application Ser. No. 10/997,078, filed on Nov. 24, 2007 and published as U.S. 2005/0221444, and now U.S. Pat. No. 7,501,484, which is a continuation under 35 U.S.C. 111(a) of PCT/US03/16643, filed on May 23, 2003 and published on Dec. 4, 2003, as WO 03/100021 A2, which claims priority under 35 U.S.C. 119(e) of U.S. Provisional Application No. 60/383,370, filed on May 24, 2002, which applications and publication are incorporated herein by reference.

FIELD OF INVENTION

The present invention relates generally to the field of protein expression. More specifically, it relates to methods and DNA constructs for the expression of polypeptides and proteins.

BACKGROUND OF THE INVENTION

Polypeptides are useful for the treatment of disease in humans and animals. Examples of such polypeptides include insulin for the treatment of diabetes, interferon for treating viral infections, interleukins for modulating the immune system, erythropoietin for stimulating red blood cell formation, and growth factors that act to mediate both prenatal and postnatal growth.

Many bioactive polypeptides can be produced through use of chemical synthesis methods. However, such production methods are often times inefficient and labor intensive which leads to increased cost and lessened availability of therapeutically useful polypeptides. An alternative to chemical synthesis is provided by recombinant technology which allows the high yield production of bioactive polypeptides in microbes. Such production permits a greater number of people to be treated at a lowered cost.

While great strides have been made in recombinant technology, expression of proteins and peptides in cells can be problematic. This can be due to low expression levels or through destruction of the expressed polypeptide by proteolytic enzymes contained within the cells. This is especially problematic when short proteins and peptides are being expressed.

These problems have been addressed in the past by producing fusion proteins that contain the desired polypeptide fused to a carrier polypeptide. Expression of a desired polypeptide as a fusion protein in a cell will often times protect the desired polypeptide from destructive enzymes and allow the fusion protein to be purified in high yields. The fusion protein is then treated to cleave the desired polypeptide from the carrier polypeptide and the desired polypeptide is isolated. Many carrier polypeptides have been used according to this protocol. Examples of such carrier polypeptides include β-galactosidase, glutathione-S-transferase, the N-terminus of L-ribulokinase, bacteriophage T4 gp55 protein, and bacterial ketosteroid isomerase protein. While this protocol offers many advantages, it suffers from decreased production efficiency due to the large size of the carrier protein. Thus, the desired polypeptide may make up a small percentage of the total mass of the purified fusion protein resulting in decreased yields of the desired polypeptide.

Another method to produce a desired polypeptide through recombinant technology involves producing a fusion protein that contains the desired polypeptide fused to an additional polypeptide sequence. In this case, the additional polypeptide sequence causes the fusion protein to form an insoluble mass in a cell called an inclusion body. These inclusion bodies are then isolated from the cell and the fusion protein is purified. The fusion protein is then treated to cleave the additional polypeptide sequence from the fusion protein and the desired polypeptide is isolated. This method has provided high level of expression of desired polypeptides. An advantage of such a method is that the additional polypeptide sequence will often times be smaller than the desired polypeptide and will therefore constitute a smaller percentage of the fusion protein produced leading to increased production efficiency. A disadvantage of such systems is that they produce inclusion bodies that are very difficult to solubilize in order to isolate a polypeptide of interest.

Accordingly, a need exists for additional polypeptide sequences that may be used to produce desired polypeptides through formation of inclusion bodies. A need also exists for additional polypeptide sequences that may be used to produce inclusion bodies having characteristics that allow them to be more easily manipulated during the production and purification of desired polypeptides.

SUMMARY OF THE INVENTION

The invention provides an expression cassette for the expression of a tandem polypeptide that forms an inclusion body. The invention also provides an expression cassette for the expression of a tandem polypeptide that forms an inclusion body having isolation enhancement. Also provided by the invention is an RNA produced by transcription of an expression cassette of the invention. The invention also provides a protein produced by translation of an RNA produced by transcription of an expression cassette of the invention. Also provided by the invention is a nucleic acid construct containing a vector and an expression cassette of the invention. The invention also provides a cell containing an expression cassette or a nucleic acid construct of the invention. Also provided by the invention is a tandem polypeptide containing an inclusion body-fusion partner operably linked to a preselected polypeptide. The invention also provides a method to select an inclusion body fusion partner that confers isolation enhancement to an inclusion body.

The expression cassette can encode a tandem polypeptide that includes a preselected polypeptide that is operably linked to an inclusion body fusion partner. The expression cassette can encode a tandem polypeptide that includes a preselected polypeptide that is operably linked to an inclusion body fusion partner and a cleavable peptide linker. The expression cassette can also encode a tandem polypeptide that includes a preselected polypeptide that is operably linked to an inclusion body fusion partner, and a fusion tag. The expression cassette can also encode a tandem polypeptide that includes a preselected polypeptide that is operably linked to an inclusion body fusion partner, a cleavable linker peptide, and a fusion tag. The expression cassette can encode a tandem polypeptide having a preselected polypeptide, an inclusion body fusion partner, a cleavable peptide linker, and a fusion tag operably linked in any order that will cause the tandem polypeptide to form an inclusion body.

Preferably, the expression cassette encodes a preselected polypeptide that is a bioactive polypeptide. More preferably the expression cassette encodes a preselected polypeptide that is useful to treat a disease in a human or animal. Even more preferably the expression cassette encodes a preselected polypeptide that is glucagon-like peptide-1 (GLP-1), glucagon-like peptide-2 (GLP-2), parathyroid hormone (PTH), or growth hormone releasing factor (GRF). Preferably the expression cassette encodes a preselected polypeptide that is a protease. More preferably the expression cassette encodes a preselected polypeptide that is clostripain. The expression cassette can encode more than one copy of a preselected polypeptide. Preferably the expression cassette encodes twenty copies of a preselected polypeptide. More preferably the expression cassette encodes ten copies of a preselected polypeptide. Even more preferably the expression cassette encodes five copies of a preselected polypeptide. Still even more preferably the expression cassette encodes two copies of a preselected polypeptide. Most preferably the expression cassette encodes one copy of a preselected polypeptide.

Preferably the expression cassette encodes an inclusion body fusion partner having an amino acid sequence that is a variant of any one of SEQ ID NOs: 1-15. More preferably the expression cassette encodes an inclusion body fusion partner having an amino acid sequence corresponding to any one of SEQ ID NOs: 1-15. Preferably the expression cassette encodes an inclusion body fusion partner that confers isolation enhancement to the inclusion body formed from the tandem polypeptide. More preferably the expression cassette encodes an inclusion body fusion partner that confers protease resistance, controllable solubility, purification stability; or self-adhesion to an inclusion body formed from a tandem polypeptide. The expression cassette can encode an inclusion body fusion partner that can be operably linked to a preselected polypeptide at the amino-terminus of the preselected polypeptide, the carboxyl-terminus of the preselected polypeptide, or the amino-terminus and the carboxyl-terminus of the preselected polypeptide. Preferably the expression cassette encodes an inclusion body fusion partner that is independently operably linked to each of the amino-terminus and the carboxyl-terminus of a preselected polypeptide. More preferably the expression cassette encodes an inclusion body fusion partner that is operably linked to the carboxyl-terminus of a preselected polypeptide. Even more preferably the expression cassette encodes an inclusion body fusion partner that is operably linked to the amino-terminus of a preselected polypeptide. The expression cassette can encode one or more inclusion body fusion partners that can be operably linked to the amino-terminus, the carboxyl-terminus or the amino-terminus and the carboxyl-terminus of a preselected polypeptide. Preferably the expression cassette encodes twenty inclusion body fusion partners that are operably linked to the preselected polypeptide. More preferably the expression cassette encodes ten inclusion body fusion partners that are linked to the preselected polypeptide. Even more preferably the expression cassette encodes five inclusion body fusion partners that are linked to the preselected polypeptide. Still even more preferably the expression cassette encodes two inclusion body fusion partners that are linked to the preselected polypeptide. Most preferably the expression cassette encodes one inclusion body fusion partner that is linked to the preselected polypeptide.

Preferably the expression cassette encodes a fusion tag that increases the ease with which an operably linked tandem polypeptide can be isolated. More preferably the expression cassette encodes a fusion tag that is a poly-histidine tag. More preferably the expression cassette encodes a fusion tag that is an epitope tag. Even more preferably the expression cassette encodes a fusion tag that is a substrate binding tag. Still even more preferably the expression cassette encodes a fusion tag that is glutathione-S-transferase or arabinose binding protein.

The expression cassette can encode a fusion tag that is a ligand for a cellular receptor. Preferably the expression cassette encodes a fusion tag that is a ligand for an insulin receptor.

The expression cassette of the invention can encode one or more cleavable peptide linkers that are operably linked to an inclusion body fusion partner and a preselected polypeptide. The expression cassette of the invention can also encode one or more cleavable peptide linkers that are operably linked to an inclusion body fusion partner, a preselected polypeptide and a fusion tag. Preferably the expression cassette encodes a tandem polypeptide having twenty cleavable peptide linkers. More preferably the expression cassette encodes a tandem polypeptide having ten cleavable peptide linkers. Even more preferably the expression cassette encodes a tandem polypeptide having five cleavable peptide linkers. Most preferably the expression cassette encodes a tandem polypeptide having a cleavable peptide linker independently positioned; between an inclusion body fusion partner and a preselected polypeptide, between an inclusion body fusion partner and a fusion tag, between two preselected polypeptides, or between a preselected polypeptide and a fusion tag.

The expression cassette can encode a cleavable peptide linker that may be cleaved with a chemical agent. Preferably the expression cassette encodes a cleavable peptide linker that is cleavable with cyanogen bromide. More preferably the expression cassette encodes a cleavable peptide linker that is cleavable with palladium. The expression cassette can encode a cleavable peptide linker which may be cleaved with a protease. Preferably the expression cassette encodes a cleavable peptide linker that is cleavable with a tissue specific protease. More preferably the expression cassette encodes a cleavable peptide linker that is cleavable with a serine protease, an aspartic protease, a cysteine protease, or a metalloprotease. Most preferably the expression cassette encodes a cleavable peptide linker that is cleavable with clostripain.

The expression cassette of the invention includes a promoter. Preferably the promoter is a constitutive promoter. More preferably the promoter is a regulatable promoter. Most preferably the promoter is an inducible promoter.

The expression cassette of the invention may include one or more suppressible stop codons. Preferably a suppressive stop codon is an amber or an ochre stop codon.

The expression cassette of the invention may encode a fusion tag. The expression cassette can encode a fusion tag that may be a ligand binding domain. Preferably the expression cassette encodes a fusion tag that is a metal binding domain. More preferably the expression cassette encodes a fusion tag that is a sugar binding domain. Even more preferably the expression cassette encodes a fusion tag that is a peptide binding domain. Most preferably the expression cassette encodes a fusion tag that is an amino acid binding domain. The expression cassette can encode a fusion tag that may be an antibody epitope. Preferably the expression cassette encodes a fusion tag that is recognized by an anti-maltose binding protein antibody. More preferably the expression cassette encodes a fusion tag that is recognized by an anti-T7 gene 10 bacteriophage antibody. The expression cassette can encode a fusion tag that may be a fluorescent protein. Preferably the expression cassette encodes a fusion tag that is a green fluorescent protein, a yellow fluorescent protein, a red fluorescent protein or a cayenne fluorescent protein.

The invention provides a nucleic acid construct containing a vector and an expression cassette of the invention. Preferably the vector is a plasmid, phagemid, cosmid, F-factor, virus, bacteriophage, yeast artificial chromosome, or bacterial artificial chromosome. Preferably the nucleic acid construct is RNA. More preferably the nucleic acid construct is DNA.

The invention provides a cell containing a nucleic acid construct of the invention. Preferably the cell is a eukaryotic cell. More preferably the eukaryotic cell is a mammalian cell. Even more preferably the eukaryotic cell is a yeast cell. Most preferably the eukaryotic cell is an insect cell. More preferably the cell is a prokaryotic cell. Even more preferably the prokaryotic cell is a bacterium. Still even more preferably the prokaryotic cell is an *Escherichia coli*. Most preferably the prokaryotic cell is *Escherichia coli* BL21.

The invention provides a tandem polypeptide that includes a preselected polypeptide that is operably linked to an inclusion body fusion partner. The invention also provides a tandem polypeptide that includes a preselected polypeptide that is operably linked to an inclusion body fusion partner and a cleavable peptide linker. The invention also provides a tandem polypeptide that includes a preselected polypeptide that is operably linked to an inclusion body fusion partner, and a fusion tag. The invention also provides a tandem polypeptide that includes a preselected polypeptide that is operably linked to an inclusion body fusion partner, a cleavable linker peptide, and a fusion tag. The invention also provides a tandem polypeptide that includes a preselected polypeptide that is operably linked to an inclusion body fusion partner, and independently operably linked to one or more cleavable peptide linkers, or to one or more fusion tags in any order that will cause a tandem polypeptide to form an inclusion body.

The invention also provides a method to select an inclusion body fusion partner that confers isolation enhancement to an inclusion body. Preferably the isolation enhancement is altered isoelectric point. More preferably the isolation enhancement is protease resistance. Even more preferably the isolation enhancement is increased solubility. Still even more preferably the isolation enhancement is self-adhesion. Most preferably the isolation enhancement is purification stability.

DEFINITIONS

Abbreviations: IPTG: isopropylthio-β-D-galactoside; PCR: polymerase chain reaction; mRNA: messenger ribonucleic acid; DNA: deoxyribonucleic acid; RNA: ribonucleic acid; β-gal: β-galactosidase; GST: glutathione-S-transferase; CAT: chloramphenicol acetyl transferase; SPA: staphylococcal protein A; SPG: streptococcal protein G; MBP: maltose binding protein; SBD: starch binding protein; $CBD_{CenA}$: cellulose-binding domain of endoglucanase A; $CBD_{Cex}$: cellulose binding domain of exoglucanase Cex; FLAG: hydrophilic 8-amino acid peptide; TrpE: tryptophan synthase; GLP-1: glucagon-like peptide-1; GLP-2: glucagone-like peptide-2; PTH: parathyroid hormone; GRF: growth hormone releasing factor; PAGE: polyacrylamide gel electrophoresis, SDS: sodium dodecyl sulfate, Vg: vestigial.

The term "Altered isoelectric point" refers to changing the amino acid composition of an inclusion body fusion partner to effect a change in the isoelectric point of a tandem polypeptide that includes the inclusion body fusion partner operably linked to a preselected polypeptide.

An "Amino acid analog" includes amino acids that are in the D rather than L form, as well as other well known amino acid analogs, e.g., N-alkyl amino acids, lactic acid, and the like. These analogs include phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, pemcillamine, ornithine, citruline, N-methyl-alanine, para-benzoyl-phenylalanine, phenylglycine, propargylglycine, sarcosine, N-acetylserine, N-formylmethionine, 3-methylhistidine, 5-hydroxylysine, norleucine, norvaline, orthonitrophenylglycine, and other similar amino acids.

The terms, "cells," "cell cultures", "Recombinant host cells", "host cells", and other such terms denote, for example, microorganisms, insect cells, and mammalian cells, that can be, or have been, used as recipients for nucleic acid constructs or expression cassettes, and include the progeny of the original cell which has been transformed. It is understood that the progeny of a single parental cell may not necessarily be completely identical in morphology or in genomic or total DNA complement as the original parent, due to natural, accidental, or deliberate mutation. Many cells are available from ATCC and commercial sources. Many mammalian cell lines are known in the art and include, but are not limited to, Chinese hamster ovary (CHO) cells, HeLa cells, baby hamster kidney (BHK) cells, monkey kidney cells (COS), and human hepatocellular carcinoma cells (e.g., Hep G2). Many prokaryotic cells are known in the art and include, but are not limited to, *Escherichia coli* and *Salmonella typhimurium*. Sambrook and Russell, Molecular Cloning: A Laboratory Manual, 3rd edition (Jan. 15, 2001) Cold Spring Harbor Laboratory Press, ISBN: 0879695765. Many insect cells are known in the art and include, but are not limited to, silkworm cells and mosquito cells. (Franke et al., *J. Gen. Virol.*, 66:2761 (1985); Marumoto et al., *J. Gen. Virol.*, 68:2599 (1987)).

A "Cleavable peptide linker" (CPL) refers to a peptide sequence having a cleavage recognition sequence. A cleavable peptide linker can be cleaved by an enzymatic or a chemical cleavage agent. Examples of cleavable peptide linkers include, but are not limited to, those provided in Table V and Table VI. Numerous peptide sequences are known that are cleaved by enzymes or chemicals. Harlow and Lane, Antibodies: A Laboratory Manual, Cold Spring Harbor Laboratory Press, Cold Spring Harbor, N.Y. (1988); Walsh, Proteins Biochemistry and Biotechnology, John Wiley & Sons, LTD., West Sussex, England (2002).

A "Cleavage agent" is a chemical or enzyme that recognizes a cleavage site in a polypeptide and causes the polypeptide to be split into two polypeptides through breakage of a bond within the polypeptide. Examples of cleavage agents include, but are not limited to, chemicals and proteases.

A "Coding sequence" is a nucleic acid sequence that is translated into a polypeptide, such as a preselected polypeptide, usually via mRNA. The boundaries of the coding sequence are determined by a translation start codon at the 5'-terminus and a translation stop codon at the 3'-terminus of an mRNA. A coding sequence can include, but is not limited to, cDNA, and recombinant nucleic acid sequences.

A "Conservative amino acid" refers to an amino acid that is functionally similar to a second amino acid. Such amino acids may be substituted for each other in a polypeptide with a minimal disturbance to the structure or function of the polypeptide according to well known techniques. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q).

"Constitutive promoter" refers to a promoter that is able to express a gene or open reading frame without additional regulation. Such constitutive promoters provide constant expression of operatively linked genes or open reading frames under nearly all conditions.

A "Fusion tag" is an amino acid segment that can be operably linked to a tandem polypeptide that contains an inclusion body fusion partner operably linked to a preselected amino acid sequence. A fusion tag may exhibit numerous properties. For example, the fusion tag may selectively bind to purification media that contains a binding partner for the fusion tag and allow the operably linked tandem polypeptide to be easily purified. Such fusion tags may include, but are not limited to, glutathione-S-transferase, polyhistidine, maltose binding protein, avidin, biotin, or streptavidin. In another example, a fusion tag may be a ligand for a cellular receptor, such as an insulin receptor. This interaction will allow a tandem polypeptide that is operably linked to the fusion tag to be specifically targeted to a specific cell type based on the receptor expressed by the cell. In another example, the fusion tag may be a polypeptide that serves to label the operably linked tandem polypeptide. Examples of such fusion tags include, but are not limited to, green fluorescent protein, red fluorescent protein, yellow fluorescent protein, cayenne fluorescent protein.

The term "Gene" is used broadly to refer to any segment of nucleic acid that encodes a preselected polypeptide. Thus, a gene may include a coding sequence for a preselected polypeptide and/or the regulatory sequences required for expression. A gene can be obtained from a variety of sources, including being cloned from a source of interest or by being synthesized from known or predicted sequence information. A gene of the invention may also be optimized for expression in a given organism. For example, a codon usage table may be used to optimize a gene for expression in *Escherichia coli*. Harlow and Lane, Antibodies: A Laboratory Manual, Cold Spring Harbor Laboratory Press, Cold Spring Harbor, N.Y. (1988).

An "Inclusion body" is an amorphous deposit in the cytoplasm of a cell; an aggregated protein appropriate to the cell but damaged, improperly folded or liganded, or a similarly inappropriately processed foreign protein, such as a viral coat protein or recombinant DNA product.

An "Inclusion body fusion partner" is an amino acid sequence having any one of SEQ ID NOs: 1-15, or variants thereof, that cause a tandem polypeptide containing a preselected polypeptide and an inclusion body fusion partner to form an inclusion body when expressed within a cell. The inclusion body fusion partners of the invention can be altered to confer isolation enhancement onto an inclusion body that contains the altered inclusion body fusion partner. Examples of inclusion body fusion partners include, but are not limited to, those provided in Table I and Table II.

"Inducible promoter" refers to those regulated promoters that can be turned on by an external stimulus (e.g., a chemical, nutritional stress, or heat). For example, the lac promoter can be induced through use of IPTG (isopropylthio-β-D-galactoside). In another example, the bacteriophage lambda $P_L$ promoter can be regulated by the temperature-sensitive repressor, cIts857 which represses $P_L$ transcription at low temperatures but not at high temperatures. Thus, temperature shift may be used to induce transcription from the $P_L$ promoter. Sambrook and Russell, Molecular Cloning: A Laboratory Manual 3rd edition (Jan. 15, 2001) Cold Spring Harbor Laboratory Press, ISBN: 0879695765.

The term "Isolation enhancement" refers to the alteration of characteristics of an inclusion body that aid in purification of polypeptides that compose the inclusion body. For example, alteration of an inclusion body fusion partner to increase the solubility of an inclusion body formed from tandem polypeptides that include the altered inclusion body fusion partner would be isolation enhancement. In another example, alteration of an inclusion body fusion partner to control the solubility of an inclusion body at a select pH would be isolation enhancement.

An "open reading frame" (ORF) is a region of a nucleic acid sequence that encodes a polypeptide, such as a preselected polypeptide; this region may represent a portion of a coding sequence or a total coding sequence.

"Operably-linked" refers to the association of nucleic acid sequences or amino acid sequences on a single nucleic acid fragment or a single amino acid sequence so that the function of one is affected by the other. For example, a regulatory DNA sequence is said to be "operably linked to" or "associated with" a DNA sequence that codes for an RNA if the two sequences are situated such that the regulatory DNA sequence affects expression of the coding DNA sequence (i.e., that the coding sequence or functional RNA is under the transcriptional control of the promoter). In an example related to amino acid sequences, an inclusion body fusion partner is said to be operably linked to a preselected amino acid sequence when the inclusion body fusion partner causes a tandem polypeptide to form an inclusion body. In another example, a signal sequence is said to be operably linked to a preselected amino acid when the signal sequence directs the tandem polypeptide to a specific location in a cell.

An "Operator" is a site on DNA at which a repressor protein binds to prevent transcription from initiating at the adjacent promoter. Many operators and repressors are known and are exemplified by the lac operator and the lac repressor. Lewin, Genes VII, Oxford University Press, New York, N.Y. (2000).

The term "polypeptide" refers to a polymer of amino acids, thus, peptides, oligopeptides, and proteins are included within the definition of polypeptide. This term also includes post expression modifications of the polypeptide, for example, glycosylations, acetylations, phosphorylations and the like. Included within the definition are, for example, polypeptides containing one or more analogues of an amino acid or labeled amino acids. Examples of rabiolabeled amino acids include, but are not limited to, $S^{35}$-methionine, $S^{35}$-cysteine, $H^3$-alanine, and the like. The invention may also be used to produce deuterated polypeptides by growing cells that express the polypeptide in deuterium. Such deuterated polypeptides are particularly useful during NMR studies.

"Promoter" refers to a nucleotide sequence, usually upstream (5') to its coding sequence, which controls the expression of the coding sequence by providing the recognition site for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or environmental conditions.

The term "Purification stability" refers to the isolation characteristics of an inclusion body formed from a tandem polypeptide having an inclusion body fusion partner operably linked to a preselected polypeptide. High purification stability indicates that an inclusion body is able to be isolated from a cell in which it was produced. Low purification stability indicates that the inclusion body is unstable during purification due to dissociation of the tandem polypeptides forming the inclusion body.

"Purified" and "isolated" mean, when referring to a polypeptide or nucleic acid sequence, that the indicated molecule is present in the substantial absence of other biological macromolecules of the same type. The term "purified" as used herein preferably means at least 75% by weight, more preferably at least 85% by weight, more preferably still at least 95% by weight, and most preferably at least 98% by weight, of biological macromolecules of the same type present (but water, buffers, and other small molecules, especially molecules having a molecular weight of less than 1000, can be present).

"Regulated promoter" refers to a promoter that directs gene expression in a controlled manner rather than in a constitutive manner. Regulated promoters include inducible promoters and repressible promoters. Such promoters may include natural and synthetic sequences as well as sequences which may be a combination of synthetic and natural sequences. Different promoters may direct the expression of a gene in response to different environmental conditions. Typical regulated promoters useful in the invention include, but are not limited to, promoters used to regulate metabolism (e.g., an IPTG-inducible lac promoter) heat-shock promoters (e.g., an SOS promoter), and bacteriophage promoters (e.g., a T7 promoter).

A "Ribosome binding site" is a DNA sequence that encodes a site on an mRNA at which the small and large subunits of a ribosome associate to form an intact ribosome and initiate translation of the mRNA. Ribosome binding site consensus sequences include AGGA or GAGG and are usually located some 5 to 13 nucleotides upstream (5') of the initiator AUG codon on the mRNA. Many ribosome binding sites are known in the art. (Shine et al., Nature, 254:34, (1975); Steitz et al., "Genetic signals and nucleotide sequences in messenger RNA", in: Biological Regulation and Development: Gene Expression (ed. R. F. Goldberger) (1979)).

The term "Self-adhesion" refers to the association between individual tandem polypeptides, having an inclusion body fusion partner operably linked to a preselected polypeptide sequence, to form an inclusion body. Self-adhesion affects the purification stability of an inclusion body formed from a tandem polypeptide. Self-adhesion that is too great produces inclusion bodies having tandem polypeptides that are so tightly associated with each other that it is difficult to separate individual tandem polypeptides from an isolated inclusion body. Self-adhesion that is too low produces inclusion bodies that are unstable during isolation due to dissociation of the tandem polypeptides that form the inclusion body. Self-adhesion can be regulated by altering the amino acid sequence of an inclusion body fusion partner.

A "Signal sequence" is a region in a protein or polypeptide responsible for directing an operably linked polypeptide to a cellular location, compartment, or secretion from the cell as designated by the signal sequence. For example, signal sequences direct operably linked polypeptides to the inner membrane, periplasmic space, and outer membrane in bacteria. The nucleic acid and amino acid sequences of such signal sequences are well known in the art and have been reported. Watson, Molecular Biology of the Gene, 4th edition, Benjamin/Cummings Publishing Company, Inc., Menlo Park, Calif. (1987); Masui et al., in: Experimental Manipulation of Gene Expression, (1983); Ghrayeb et al., EMBO J., 3: 2437 (1984); Oka et al. Proc. Natl. Acad. Set. USA, 82: 7212 (1985); Palva et al., Proc. Natl. Acad. Sci. USA, 79: 5582 (1982); U.S. Pat. No. 4,336,336).

Signal sequences, preferably for use in insect cells, can be derived from genes for secreted insect or baculovirus proteins, such as the baculovirus polyhedrin gene (Carbonell et al. Gene, 22: 409 (1988)). Alternatively, since the signals for mammalian cell posttranslational modifications (such as signal peptide cleavage, proteolytic cleavage, and phosphorylation) appear to be recognized by insect cells, and the signals required for secretion and nuclear accumulation also appear to be conserved between the invertebrate cells and vertebrate cells, signal sequences of non-insect origin, such as those derived from genes encoding human α-interferon (Maeda et al., Nature, 315:592 (1985)), human gastrin-releasing peptide (Lebacq-Verheyden et al., Mol. Cell. Biol., 8: 3129 (1988)), human IL-2 (Smith et al., Proc. Natl. Acad. Sci. USA, 82: 8404 (1985)), mouse IL-3 (Miyajima et al., Gene, 58: 273 (1987)) and human glucocerebrosidase (Martin et al., DNA, 7: 99 (1988)), can also be used to provide for secretion in insects.

Suitable yeast signal sequences can be derived from genes for secreted yeast proteins, such as the yeast invertase gene (EPO Publ. No. 012 873; JPO Publ. No. 62,096,086) and the A-factor gene (U.S. Pat. No. 4,588,684). Alternatively, sequences of non-yeast origin, such as from interferon, exist that also provide for secretion in yeast (EPO Publ. No. 060 057).

The term "Solubility" refers to the amount of a substance that can be dissolved in a unit volume of solvent. For example, solubility as used herein refers to the ability of a tandem polypeptide to be resuspended in a volume of solvent, such as a biological buffer.

A "Suppressible stop codon" is a codon that serves as a stop codon to translation of an RNA that contains the suppressible stop codon when the RNA is translated in a cell that is not a suppressing cell. However, when the RNA is translated in a cell that is a suppressing cell, the suppressing cell will produce a transfer RNA that recognizes the suppressible stop codon and provides for insertion of an amino acid into the growing polypeptide chain. This action allows translation of the RNA to continue past the suppressible stop codon. Suppressible stop codons are sometimes referred to as nonsense mutations. Suppressible stop codons are well known in the art and include such examples as amber mutations (UAG) and ochre mutations (UAA). Numerous suppressing cells exist which insert an amino acid into a growing polypeptide chain at a position corresponding to a suppressible stop codon. Examples of suppressors, codon recognized, and the inserted amino acid include: supD, amber, serine; supE, amber, glutamine; supF, amber, tyrosine; supB, amber and ochre, glutamine; and supC, amber and ochre, tyrosine. Other suppressors are known in the art. Additionally, numerous cells are known in the art that are suppressing cells. Examples of such cells include, but are not limited to, the bacterial strains: 71/18 (supE); BB4 (supF58 and supE44); BNN102 (supE44); C600 (supE44); and CSH18 (supE). Those of skill in the art realize that many suppressing cells are known and are obtainable from ATCC or other commercial sources. A suppressible stop codon can be used to insert a specific amino acid into a polypeptide chain at a specific location. Such insertion can be used to create a specific amino acid sequence in a polypeptide that serves as a cleavage site for a chemical or enzymatic agent. Through selection of an appropriate suppressible stop codon and translation of an RNA containing the suppressible stop codon in an appropriate cell, one skilled in the art can control what chemical or enzymatic agent can cleave a polypeptide chain at a given position.

A "Tandem polypeptide" as defined herein is a protein having an inclusion body fusion partner operably linked to a preselected polypeptide that may optionally include additional amino acids. A tandem polypeptide is further defined as forming an inclusion body when expressed in a cell.

A "Tissue specific protease" refers to a proteolytic enzyme that is expressed in specific cells at a higher level than in other cells of a different type. Prostate specific antigen is an example of a tissue specific protease.

A "Transcription terminator sequence" is a signal within DNA that functions to stop RNA synthesis at a specific point along the DNA template. A transcription terminator may be either rho factor dependent or independent. An example of a transcription terminator sequence is the T7 terminator. Transcription terminators are known in the art and may be isolated from commercially available vectors according to recombinant methods known in the art (Sambrook and Russell, Molecular Cloning: A Laboratory Manual, 3rd edition (Jan. 15, 2001) Cold Spring Harbor Laboratory Press, ISBN: 0879695765; Stratagene, La Jolla, Calif.).

"Transformation" refers to the insertion of an exogenous nucleic acid sequence into a host cell, irrespective of the method used for the insertion. For example, direct uptake, transduction, f-mating or electroporation may be used to introduce a nucleic acid sequence into a host cell. The exogenous nucleic acid sequence may be maintained as a non-integrated vector, for example, a plasmid, or alternatively, may be integrated into the host genome.

A "Translation initiation sequence" refers to a DNA sequence that codes for a sequence in a transcribed mRNA that provides high level translation initiation. Numerous translation initiation sequences are known in the art. These sequences are sometimes referred to as leader sequences. A translation initiation sequence may include an optimized ribosome binding site. In the present invention, bacterial translational start sequences are preferred. Such translation initiation sequences are well known in the art and may be obtained from bacteriophage T7, bacteriophage φ10, and the gene encoding ompT. Those of skill in the art can readily obtain and clone translation initiation sequences from a variety of commercially available plasmids, such as the pET (plasmid for expression of T7 RNA polymerase) series of plasmids. (Stratagene, La Jolla, Calif.).

A "variant" polypeptide is a polypeptide derived from the native polypeptide by deletion or addition of one or more amino acids to the N-terminal and/or C-terminal end of the native polypeptide; deletion or addition of one or more amino acids at one or more sites in the native protein; or substitution of one or more amino acids at one or more sites in the native protein. Such substitutions or insertions are preferably conservative amino acid substitutions. Methods for such manipulations are generally known in the art. Kunkel, *Proc. Natl. Acad. Sci. USA*, 82:488, (1985); Kunkel et al., *Methods in Enzymol.*, 154:367 (1987); U.S. Pat. No. 4,873,192; Walker and Gaastra, eds. (1983) *Techniques in Molecular Biology* (MacMillan Publishing Company, New York) and the references cited therein. Also, kits are commercially available for mutating DNA. (Quick change Kit, Stratagene, La Jolla, Calif.): Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.).

A "Vector" includes, but is not limited to, any plasmid, cosmid, bacteriophage, yeast artificial chromosome, bacterial artificial chromosome, f-factor, phagemid or virus in double or single stranded linear or circular form which may or may not be self transmissible or mobilizable, and which can transform a prokaryotic or eukaryotic host either by integration into the cellular genome or exist extrachromosomally (e.g., autonomous replicating plasmid with an origin of replication).

Specifically included are shuttle vectors by which are DNA vehicles capable, naturally or by design, of replication in two different host organisms (e.g., bacterial, mammalian, yeast or insect cells).

BRIEF DESCRIPTION OF THE DRAWINGS

FIGS. 3A and B illustrates the nucleic acid amino acid sequence for the T7tagVgCH-GRF(1-44)A cassette. The leader sequence, Vg sequence, Linker sequence, and GRF(1-44)A sequences are indicated by bracketed lines. Restriction enzyme recognition sites are indicated by name and by underlining. The cleavage site is indicated by an arrow.

FIG. 4 illustrates the nucleic acid and amino acid sequence for the T7tag-GRF(1-44)A cassette. The T7tag, linker, and GRF(1-44)A nucleic acid and amino acid sequences are indicated. Restriction enzyme recognition sites are indicated by name and by underlining. An enterokinase recognition site is indicated by an arrow.

FIGS. 5A and B illustrates the nucleic acid and amino acid sequence for the T7tagVg-GRF(1-44)A cassette. The leader sequence, Vg sequence, Linder sequence, and GRF(1-44)A sequences are indicated by bracketed lines. Restriction enzyme recognition sites are indicated by name and by underlining. The cleavage site is indicated by an arrow. The stop codon is labeled and indicated by stars.

FIG. 6 illustrates the nucleic acid and amino acid sequence for T7tagVg(opt)CH-GRF(1-44)A cassette. Optimized codons are underlined. The stop codon is indicated with a star.

FIG. 8 illustrates the nucleic acid and amino acid sequence for the T7tagBfMut1CH-GRF(1-44)A cassette. Amino acid substitutions are indicated as being encoded by codons in lower case. Restriction enzyme recognition sites are indicated by name. The stop codon is indicated with a star.

FIG. 9 illustrates the nucleic acid and amino acid sequence for the T7tagVgMut4CH-GRF(1-44)A cassette. Amino acid substitutions are indicated by lower cases letters. The stop codon is indicated with a start.

FIG. 10 illustrates the nucleic acid and amino acid sequence for the T7tagVg-PTH(1-34) cassette. A thrombin cleavage site is located between amino acids at positions 55 and 56. Restriction sites are indicated by underlining and name.

FIG. 11 illustrates the nucleic acid and amino acid sequence for a linker sequence containing a paladium cleavage site located between amino acids at position 16 and 17. The T7tag, linker, and Pd cleavage sequences are indicated.

FIG. 12 provides DNA and peptide sequences of the pET23 T7tagVg(Del3)-CHPTH(1-34) and pET23T7TagVg(Del2+3)CHPTH(1-34) expression cassettes encoding the PTH precursor peptide. Optimized codons are indicated with underlining, and restriction enzyme recognition sites are indicated by name and by underlining.

FIG. 13 is a plasmid map for the pBN115-T7tagVg-CAT plasmid.

FIG. 14 illustrates the nucleic acid and amino acid sequence for a NheI-releaseable T7Vg fragment. Restriction enzyme recognition sites are indicated by name.

FIG. 17 illustrates the nucleic acid and amino acid sequence of a T7tagVgCH-GLP-1(7-36)CH cassette. A restriction enzyme recognition site is indicated by name.

DETAILED DESCRIPTION OF THE INVENTION

Figure 1:
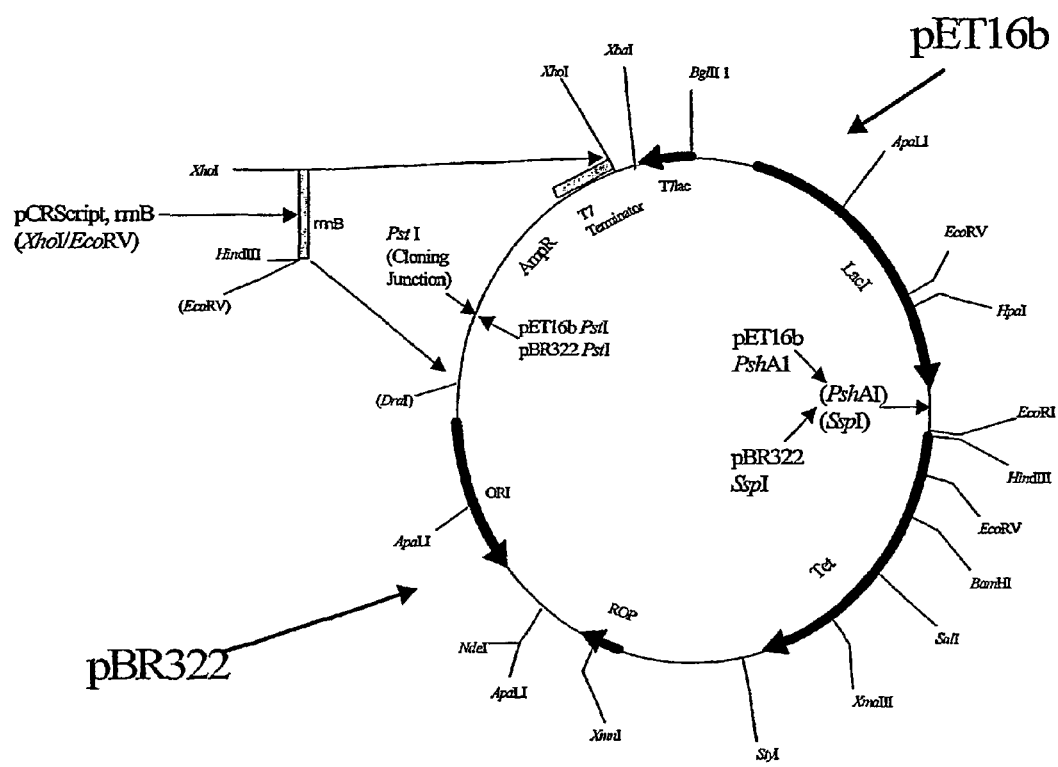
FIG. 1 is a plasmid map for the pBN95 Expression Plasmid.

The invention provides methods and materials that allow a preselected polypeptide to be efficiently expressed in a cell. A nucleic acid sequence that encodes a preselected polypeptide is inserted into an expression cassette provided by the invention. The expression cassette causes the preselected polypeptide to be operably linked to an inclusion body fusion partner to form a tandem polypeptide. The tandem polypeptide will form an inclusion body in the cell in which the tandem polypeptide is expressed.

A significant advantage of producing polypeptides by recombinant DNA techniques rather than by isolating and purifying a polypeptide from a natural source is that equivalent quantities of the protein can be produced by using less starting material than would be required for isolating the polypeptide from a natural source. Furthermore, inclusion body formation allows a tandem polypeptide to be more readily purified and protects the tandem polypeptide against unwanted degradation within the cell. Producing the polypeptide through use of recombinant techniques also permits the protein to be isolated in the absence of some molecules normally present in native cells. For example, polypeptide compositions free of human polypeptide contaminants can be produced because the only human polypeptide produced by the recombinant non-human host is the recombinant polypeptide at issue. Furthermore, potential viral agents from natural sources and viral components pathogenic to humans are also avoided.

I. Expression Cassette

The invention provides an expression cassette capable of directing the expression of a tandem polypeptide that includes a preselected polypeptide that is operably linked to an inclusion body fusion partner. The invention also provides an expression cassette capable of directing the expression of a tandem polypeptide that includes a preselected polypeptide that is operably linked to an inclusion body fusion partner and a cleavable peptide linker. The invention also provides an expression cassette capable of directing the expression of a tandem polypeptide that includes a preselected polypeptide that is operably linked to an inclusion body fusion partner and a fusion tag. The invention also provides an expression cassette capable of directing the expression of a tandem polypeptide that includes a preselected polypeptide that is operably linked to an inclusion body fusion partner, a cleavable linker peptide, and a fusion tag. The invention also provides an expression cassette capable of directing the expression of a tandem polypeptide which includes a preselected polypeptide that is operably linked to an inclusion body fusion partner, and independently operably linked to one or more cleavable peptide, linkers, or to one or more fusion tags in any order that will cause a tandem polypeptide to form an inclusion body.

Promoters

The expression cassette of the invention includes a promoter. Any promoter able to direct transcription of the expression cassette may be used. Accordingly, many promoters may be included within the expression cassette of the invention. Some useful promoters include, constitutive promoters, inducible promoters, regulated promoters, cell specific promoters, viral promoters, and synthetic promoters. A promoter is a nucleotide sequence which controls expression of an operably linked nucleic acid sequence by providing a recognition site for RNA polymerase, and possibly other factors, required for proper transcription. A promoter includes a minimal promoter, consisting only of all basal elements needed for transcription initiation, such as a TATA-box and/or other sequences that serve to specify the site of transcription initiation. A promoter may be obtained from a variety of different sources. For example, a promoter may be derived entirely from a native gene, be composed of different elements derived from different promoters found in nature, or be composed of nucleic acid sequences that are entirely synthetic. A promoter may be derived from many different types of organisms and tailored for use within a given cell.

Promoters for Use in Bacteria

For expression of a tandem polypeptide in a bacterium, an expression cassette having a bacterial promoter will be used. A bacterial promoter is any DNA sequence capable of binding bacterial RNA polymerase and initiating the downstream (3") transcription of a coding sequence into mRNA. A promoter will have a transcription initiation region that is usually placed proximal to the 5' end of the coding sequence. This transcription initiation region usually includes an RNA polymerase binding site and a transcription initiation site. A second domain called an operator may be present and overlap an adjacent RNA polymerase binding site at which RNA synthesis begins. The operator permits negatively regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *E. coli* (Raibaud et al., *Ann. Rev. Genet.*, 18:173 (1984)). Regulated expression may therefore be positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac) (Chang et al., *Nature*, 198:1056 (1977), and maltose. Additional examples include promoter sequences derived from biosynthetic enzymes such as tryptophan (trp) (Goeddel et al., *Nuc. Acids*

Res., 8:4057 (1980); Yelverton et al., *Nuc. Acids Res.*, 9:731 (1981); U.S. Pat. No. 4,738,921; and EPO Publ. Nos. 036 776 and 121 775). The β-lactamase (bla) promoter system (Weissmann, "The cloning of interferon and other mistakes", in: Interferon 3 (ed. I. Gresser), 1981), and bacteriophage lambda $P_L$ (Shimatake et al., *Nature*, 292:128 (1981)) and T5 (U.S. Pat. No. 4,689,406) promoter systems also provide useful promoter sequences. A preferred promoter is the *Chlorella* virus promoter (U.S. Pat. No. 6,316,224).

Synthetic promoters that do not occur in nature also function as bacterial promoters. For example, transcription activation sequences of one bacterial or bacteriophage promoter may be joined with the operon sequences of another bacterial or bacteriophage promoter, creating a synthetic hybrid promoter (U.S. Pat. No. 4,551,433). For example, the tac promoter is a hybrid trp-lac promoter comprised of both trp promoter and lac operon sequences that is regulated by the lac repressor (Amann et al., *Gene*, 25:167 (1983); de Boer et al., *Proc. Natl. Acad. Sci. USA* 80:21 (1983)). Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system (Studier et al., *J. Mol. Biol.*, 189:113 (1986); Tabor et al., *Proc. Natl. Acad. Sci. USA*, 82:1074 (1985)). In addition, a hybrid promoter can also be comprised of a bacteriophage promoter and an *E. coli* operator region (EPO Publ. No. 267 851).

Promoters for Use in Insect Cells

An expression cassette having a baculovirus promoter can be used for expression of a tandem polypeptide in an insect cell. A baculovirus promoter is any DNA sequence capable of binding a baculovirus RNA polymerase and initiating transcription of a coding sequence into mRNA. A promoter will have a transcription initiation region that is usually placed proximal to the 5' end of the coding sequence. This transcription initiation region usually includes an RNA polymerase binding site and a transcription initiation site. A second domain called an enhancer may be present and is usually distal to the structural gene. A baculovirus promoter may be a regulated promoter or a constitutive promoter. Useful promoter sequences may be obtained from structural genes that are transcribed at times late in a viral infection cycle. Examples include sequences derived from the gene, encoding the baculoviral polyhedron protein (Friesen et al., "The Regulation of Baculovirus Gene Expression", in: The Molecular Biology of Baculoviruses (ed. Walter Doerfler), 1986; and EPO Publ. Nos. 127 839 and 155 476) and the gene encoding the baculoviral p10 protein (Vlak et al., *J. Gen. Virol.*, 69:765 (1988)).

Promoters for Use in Yeast

Promoters that are functional in yeast are known to those of ordinary skill in the art. In addition to an RNA polymerase binding site and a transcription initiation site, a yeast promoter may also have a second region called an upstream activator sequence. The upstream activator sequence permits regulated expression that may be induced. Constitutive expression occurs in the absence of an upstream activator sequence. Regulated expression may be either positive or negative, thereby either enhancing or reducing transcription.

Promoters for use in yeast may be obtained from yeast genes that encode enzymes active in metabolic pathways. Examples of such genes include alcohol dehydrogenase (ADH) (EPO Publ. No. 284 044), enolase, glucokinase, glucose-6-phosphate isomerase, glyceraldehyde-3-phosphatedehydrogenase (GAP or GAPDH), hexokinase, phosphofructokinase, 3-phosphoglyceratemutase, and pyruvate kinase (PyK). (EPO Publ. No. 329 203). The yeast PHO5 gene, encoding acid phosphatase, also provides useful promoter sequences. (Myanohara et al., *Proc. Natl. Acad. Sci. USA;* 80:1 (1983)).

Synthetic promoters that do not occur in nature may also be used for expression in yeast. For example, upstream activator sequences from one yeast promoter may be joined with the transcription activation region of another yeast promoter, creating a synthetic hybrid promoter. Examples of such hybrid promoters include the ADH regulatory sequence linked to the GAP transcription activation region (U.S. Pat. Nos. 4,876, 197 and 4,880,734). Other examples of hybrid promoters include promoters which consist of the regulatory sequences of either the ADH2, GAL4, GAL10, or PHO5 genes, combined with the transcriptional activation region of a glycolytic enzyme gene such as GAP or PyK (EPO Publ. No. 164 556). Furthermore, a yeast promoter can include naturally occurring promoters of non-yeast origin that have the ability to bind yeast RNA polymerase and initiate transcription. Examples of such promoters are known in the art. (Cohen et al., *Proc. Natl. Acad. Sci. USA*, 77:1078 (1980); Henikoff et al., *Nature*, 283:835 (1981); Hollenberg et al., *Curr. Topics Microbiol. Immunol.*, 96:119 (1981)); Hollenberg et al., "The Expression of Bacterial Antibiotic Resistance Genes in the Yeast *Saccharomyces cerevisiae*", in: Plasmids of Medical, Environmental and Commercial Importance (eds. K. N. Timmis and A. Punier), 1979; (Mercerau-Puigalon et al., *Gene*, 11:163 (1980); Panthier et al., *Curr. Genet.*, 2:109 (1980)).

Promoters for Use in Mammalian Cells

Many mammalian promoters are known in the art that may be used in conjunction with the expression cassette of the invention. Mammalian promoters often have a transcription initiating region, which is usually placed proximal to the 5' end of the coding sequence, and a TATA box, usually located 25-30 base pairs (bp) upstream of the transcription initiation site. The TATA box is thought to direct RNA polymerase II to begin RNA synthesis at the correct site. A mammalian promoter may also contain an upstream promoter element, usually located within 100 to 200 bp upstream of the TATA box. An upstream promoter element determines the rate at which transcription is initiated and can act in either orientation (Sambrook et al., "Expression of Cloned Genes in Mammalian Cells", in: Molecular Cloning: A Laboratory Manual, 2nd ed., 1989).

Mammalian viral genes are often highly expressed and have a broad host range; therefore sequences encoding mammalian viral genes often provide useful promoter sequences. Examples include the SV40 early promoter, mouse mammary tumour virus LTR prompter, adenovirus major late promoter (Ad MLP), and herpes simplex virus promoter. In addition, sequences derived from non-viral genes, such as the murine metallothioneih gene, also provide useful promoter sequences. Expression may be either constitutive or regulated.

A mammalian promoter may also be associated with an enhancer. The presence of an enhancer will usually increase transcription from an associated promoter. An enhancer is a regulatory DNA sequence that can stimulate transcription up to 1000-fold when linked to homologous or heterologous promoters, with synthesis beginning at the normal RNA start site. Enhancers are active when they are placed upstream or downstream from the transcription initiation site, in either normal or flipped orientation, or at a distance of more than 1000 nucleotides from the promoter. (Maniatis et al., *Science*, 236:1237 (1987)); Alberts et al., Molecular Biology of the Cell, 2nd ed., 1989). Enhancer elements derived from viruses are often times useful, because they usually have a broad host range. Examples include the SV40 early gene enhancer (Dijkema et al., *EMBO J.* 4:761(1985)) and the enhancer/promoters derived from the long terminal repeat (LTR) of the Rous Sarcoma Virus (Gorman et al., *Proc. Natl. Acad. Sci. USA,* 79:6777 (1982b)) and from human cytomegalovirus (Boshart et al., Cell, 41:521 (1985)). Additionally, some enhancers are regulatable and become active only in the presence of an inducer, such as a hormone or metal ion (Sassone-Corsi and Borelli, *Trends Genet.,* 2:215 (1986); Maniatis et al., *Science,* 236:1237 (1987)).

It is understood that many promoters and associated regulatory elements may be used within the expression cassette of the invention to transcribe an encoded tandem polypeptide. The promoters described above are provided merely as examples and are not to be considered as a complete list of promoters that are included within the scope of the invention.

Translation Initiation Sequence

The expression cassette of the invention may contain a nucleic acid sequence for increasing the translation efficiency of an mRNA encoding a tandem polypeptide of the invention. Such increased translation serves to increase production of the tandem polypeptide. The presence of an efficient ribosome binding site is useful for gene expression in prokaryotes. In bacterial mRNA a conserved stretch of six nucleotides, the Shine-Dalgarno sequence, is usually found upstream of the initiating AUG codon. (Shine et al., *Nature,* 254:34 (1975)). This sequence is thought to promote ribosome binding to the mRNA by base pairing between the ribosome binding site and the 3' end of *Escherichia coli.* 16S rRNA. (Steitz et al., "Genetic signals and nucleotide sequences in messenger RNA", in: Biological Regulation and Development: Gene Expression (ed. R. F. Goldberger), 1979)). Such a ribosome binding site, or operable derivatives thereof, are included within the expression cassette of the invention.

A translation initiation sequence can be derived from any expressed *Escherichia coli* gene and can be used within an expression cassette of the invention. Preferably the gene is a highly expressed gene. A translation initiation sequence can be obtained via standard recombinant methods, synthetic techniques, purification techniques, or combinations thereof, which are all well known. (Ausubel et al., *Current Protocols in Molecular Biology,* Green Publishing Associates and Wiley Interscience, NY. (1989); Beaucage and Caruthers, *Tetra. Letts.,* 22:1859 (1981); VanDevanter et al., *Nucleic Acids Res.,* 12:6159 (1984). Alternatively, translational start sequences can be obtained from numerous commercial vendors. (Operon Technologies; Life Technologies hie, Gaithersburg, Md.). In a preferred embodiment, the T7 translation initiation sequence is used. The T7 translation initiation sequence is derived from the highly expressed T7 Gene 10 cistron and is provided in Table VII. Other examples of translation initiation sequences include, but are not limited to, the maltose-binding protein (Mai E gene) start sequence (Guan et al., Gene, 67:21 (1997)) present in the pMalc2 expression vector (New England Biolabs, Beverly, Mass.) and the translation initiation sequence for the following genes: thioredoxin gene (Novagen, Madison, Wis.), Glutathione-S-transferase gene (Pharmacia, Piscataway, N.J.), β-galactosidase gene, chloramphenicol acetyltransferase gene and *E. coli* Tip E gene (Ausubel et al., 1989, *Current Protocols in Molecular Biology,* Chapter 16, Green Publishing Associates and Wiley Interscience, NY).

Eucaryotic mRNA does not contain a Shine-Daigarno sequence. Instead, the selection of the translational start codon is usually determined by its proximity to the cap at the 5' end of an mRNA. The nucleotides immediately surrounding the start codon in eucaryotic mRNA influence the efficiency of translation. Accordingly, one skilled in the art can determine what nucleic acid sequences will increase translation of a tandem polypeptide encoded by the expression cassette of the invention. Such nucleic acid sequences are within the scope of the invention.

Cleavable Peptide Linker

A cleavable peptide linker is an amino acid sequence that can be recognized by a cleavage agent and cleaved. Many amino acid sequences are known that are recognized and cleaved. Examples of cleavage agents and their recognition sites include, but are not limited to, chymotrypsin cleaves after phenylalanine, threonine, or tyrosine; thrombin cleaves after arginine, trypsin cleaves after lysine or arginine, and cyanogen bromide cleaves after methionine. Examples of cleavable peptide linkers include, but are not limited to, those provided in Table V and Table VI. Those of skill in the art realize that many amino acid sequences exist that may be used as a cleavable peptide linker within the scope of the invention. The expression cassette of the invention may encode a tandem polypeptide containing an inclusion body fusion partner operably linked to a preselected polypeptide and a cleavable peptide linker. Thus, an expression cassette of the invention can be designed to encode a tandem polypeptide containing a cleavable peptide linker that can be cleaved by a specific agent. In addition, the expression cassette of the invention may be designed to encode a tandem polypeptide containing multiple cleavable peptide linkers. These cleavable peptide linkers may be cleaved by the same cleavage agent or by different cleavage agents. The cleavable peptide linkers may also be positioned at different positions within the tandem polypeptide. Such a tandem polypeptide may be treated with select cleavage agents at different times to produce different cleavage products of the tandem polypeptide.

Furthermore, an expression cassette of the invention may be designed to express a tandem polypeptide containing a tissue specific protease that will promote cleavage of the tandem polypeptide in a tissue specific manner. For example, prostate specific antigen is a serine protease expressed in cells lining prostatic ducts. Prostate specific antigen exhibits a preference for cleavage at the amino acid sequence serine-serine-(tyrosine/phenylalanine)-tyrosine↓serine-(glycine/serine). (SEQ ID NO: 149) Coombs et al., *Chem. Biol.,* 5:475 (1998). Accordingly, a tandem polypeptide can be designed that is specifically cleaved in prostate tissue. Thus, the expression cassette of the invention may be used to express a tandem polypeptide that is a prodrug which is activated at a specific tissue in the body of a patient in need thereof. Such a tandem polypeptide offers the advantage that the prodrug is only activated at the site of action and potentially toxic effects on other tissues can be avoided. Those of skill in the art will recognize that the expression cassette of the invention can be used to express many different tandem polypeptides that contain a cleavable peptide linker that is tissue specific.

Inclusion Body Fusion Partner

The expression cassette of the present invention encodes a tandem polypeptide that includes an inclusion body fusion partner that is operably linked to a preselected polypeptide. It has been surprisingly found that linking an inclusion body fusion partner to a preselected polypeptide will cause the tandem polypeptide produced to form an inclusion body. Examples of inclusion body fusion partners include, but are not limited to, the inclusion body fusion partners provided in Table I and Table II. It has also been surprisingly found that the amino acid sequence of an inclusion body fusion partner can be altered to produce inclusion bodies that exhibit useful characteristics. These useful characteristics provide isolation enhancement of inclusion bodies that are formed from tandem polypeptides that include an inclusion body fusion partner of the invention. Isolation enhancement allows a tandem polypeptide containing an inclusion body fusion partner that is fused to a preselected polypeptide to be isolated and purified more readily than the preselected polypeptide in the absence of the inclusion body fusion partner. For example, the inclusion body fusion partner may be altered to produce inclusion bodies that are more or less soluble under a certain set of conditions. Those of skill in the art realize that solubility is dependent on a number of variables that include, but are not limited to, pH, temperature, salt concentration, and protein concentration. Thus, an inclusion body fusion partner of the invention may be altered to produce an inclusion body having desired solubility under differing conditions. In another example, an inclusion body fusion partner of the invention may be altered to produce inclusion bodies that contain tandem polypeptides having greater or lesser self-association. Self-association refers to the strength of the interaction between two or more tandem polypeptides that form an inclusion body and that contain an inclusion body fusion partner of the invention. Such self-association may be determined-though use of a variety of known methods used to measure protein-protein interactions. Such methods are known in the art and have been described. Freifelder, Physical Biochemistry: Applications to Biochemistry and Molecular Biology, W.H. Freeman and Co., 2nd edition, New York, N.Y. (1982). Self-adhesion can be used to produce inclusion bodies that exhibit varying stability to purification. For example, greater self-adhesion may be desirable to stabilize inclusion bodies against dissociation in instances where harsh conditions are used to isolate the inclusion bodies from a cell. Such conditions may be encountered if inclusion bodies are being isolated from cells having thick cell walls. However, where mild conditions are used to isolate the inclusion bodies, less self-adhesion may be desirable as it may allow the tandem polypeptides composing the inclusion body to be more readily solubilized or processed. Accordingly, an inclusion body fusion partner of the invention may be altered to provide a desired level of self-adhesion for a given set of conditions.

Such an inclusion body fusion partner may be linked to the amino-terminus, the carboxyl-terminus or both termini of a preselected polypeptide to form a tandem polypeptide. An inclusion body fusion partner is of an adequate size to cause an operably linked preselected polypeptide to form an inclusion body. It is preferred that the inclusion body fusion partner is 100 or less amino acids, more preferably 50 or less amino acids, and most preferably 30 or less amino acids in length.

In one example, the inclusion body fusion partner has an amino acid sequence corresponding to: GSGQGQAQYL-SASCVVFTNYSGDTASQVD (SEQ ID NO: 1). This amino acid sequence has been surprisingly found to be able to cause tandem polypeptides having an inclusion body fusion partner operably linked to a preselected polypeptide to form inclusion bodies. Another surprising discovery is that the amino acid sequence of the inclusion body fusion partner can be altered in order to produce tandem polypeptides that form inclusion bodies that exhibit isolation enhancement. The inclusion body fusion partner can also have an amino acid sequence that is a variant of SEQ ID NO. 1 and which causes inclusion body formation by an operably linked preselected polypeptide. For example, an inclusion body fusion partner can have, but is not limited to, an amino sequence corresponding to:

GSGQGQAQYLAASLVVFTNYSGDTASQVTD;        (SEQ ID NO: 2)

GSQYLAASLVVFTNYSGDTASQVD;              (SEQ ID NO: 3)

GSGQGQAQYLAASLVVFTNYSGD;               (SEQ ID NO: 4)

GSQYLAASLVVFTNYSGD;                    (SEQ ID NO: 5)

GSQYLAAVLVVFTNYSGDTASQVD;              (SEQ ID NO: 6)

GSGQGQAQYLTASLVKFTNYSGDTASQVD;         (SEQ ID NO: 7)

GSGQGQAQYLTASLVQFTNYSGDTASQVD;         (SEQ ID NO: 8)

GSGQGQAQYLPASLVKFThYSGDTASQVD;         (SEQ ID NO: 9)

GSGQGQAQYLPASLVQFTNYSGDTASQVD;         (SEQ ID NO: 10)

GSGQGQAQYLAASLVKFTNYSGDTASQVD;         (SEQ 10 NO: 11)

GSGQGQAQYLAASLVQFTNYSGDTASQVD;         (SEQ ID NO: 12)

GSGQGQAQYLSASLVKFTNYSGDTASQVD;         (SEQ ID NO: 13)

GSGQGQAQYLSASLVQFTNYSGDTASQVD;         (SEQ ID NO: 14)
or

GSGQGQAQYLAAVLVVFTNYSGDTASQVD.         (SEQ ID NO: 15)

Exemplary nucleic acid sequences that encode each of SEQ ID NOs: 1-15 are provided in Table II. Thus, an inclusion body fusion partner can also have an amino acid sequence corresponding to any one of SEQ ID NOs: 1-15, or a variant thereof, which cause inclusion body formation by an operably linked preselected polypeptide. The inclusion body fusion partner can also be linked to other amino acid sequences, such as the T7 tag sequence provided in Table VII.

An inclusion body fusion partner of the invention can be identified by operably linking an inclusion body fusion partner to a preselected polypeptide and determining if the tandem polypeptide produced forms an inclusion body within a cell. Recombinant methods that may be used to construct such variant inclusion body fusion partners are well known in the art and have been reported. Sambrook and Russell, Molecular Cloning: A Laboratory Manual, 3rd edition (Jan. 15, 2001) Cold Spring Harbor Laboratory Press, ISBN: 0879695765.

An inclusion body fusion partner variant also can be identified by comparing their sequence homology, to any one of SEQ ED NOs: 1-15. A protein fragment possessing 75% or more amino acid sequence homology, especially 85-95%, to an one of SEQ ED NOs: 1-15 is considered a variant and is encompassed by the present invention.

Mathematical algorithms, for example the Smith-Waterman algorithm, can also be used to determine sequence homology. (Smith & Waterman, *J. Mol. Biol.*, 147:195 (1981V. Pearson. *Genomics,* 11:635 (1991)). Although any sequence algorithm can be used to identify a variant, the present invention defines a variant with reference to the Smith-Waterman algorithm, where any one of SEQ ID NOs: 1-15 is used as the reference sequence to define the percentage of homology of peptide homologues over its length. The choice of parameter values for matches, mismatches, and inserts or deletions is arbitrary, although some parameter values have been found to yield more biologically realistic results than others. One preferred set of parameter values for the Smith-Waterman algorithm is set forth in the "maximum similarity segments" approach, which uses values of 1 for a matched residue and −⅓ for a mismatched residue (a residue being either a single nucleotide or single amino acid) (Waterman, *Bulletin of Mathematical Biology*, 46:473 (1984)). Insertions and deletions x, are weighted as $x_k=1+k/3$, where k is the number of residues in a given insert or deletion. Preferred variant inclusion body fusion partners are those having greater than 75% amino acid sequence homology to any one of SEQ ID NOs: 1-15 using the Smith-Waterman algorithm. More preferred variants have greater than 90% amino acid sequence homology. Even more preferred variants have greater than 95% amino acid sequence homology, and most preferred variants have at least 98% amino acid sequence homology.

Open Reading Frames

Numerous nucleic acid sequences can be inserted into an expression cassette or a nucleic acid construct of the invention and used to produce many different preselected polypeptides. Such preselected polypeptides include those that are soluble or insoluble within the cell in which they are expressed. Examples of preselected polypeptides include, but are not limited to, those provided in Table III and Table IV. One skilled in the art can determine if a nucleic acid sequence can be expressed using the expression cassette of the invention by inserting the nucleic acid sequence into an expression cassette and determining if a corresponding polypeptide is produced when the nucleic acid construct is inserted into an appropriate cell.

More than one copy of an open reading frame can be inserted into an expression cassette of the invention. Preferably, a cleavable peptide linker is inserted between open reading frames if more than one is inserted into an expression cassette of the invention. Such a construct allows the tandem polypeptide to be cleaved by a cleavage agent to produce individual preselected polypeptides from the polyprotein expressed from an expression cassette containing more than one open reading frame.

An expression cassette or nucleic acid construct of the invention is thought to be particularly advantageous for producing preselected polypeptides that are degraded within a cell in which they are expressed. Short polypeptides are examples of such preselected polypeptides. The present expression cassettes and nucleic acid constructs are also thought to be advantageous for producing preselected polypeptides that are difficult to purify from cells. For example, operably linking an inclusion body fusion partner to a preselected polypeptide that would normally associate tightly with a cell wall or membrane may allow the protein to be more easily purified from an inclusion body.

Preferred open reading frames encode glucagon-like peptide-1 (GLP-1, glucagon-like peptide-2 (GLP-2), parathyroid hormone (PTH), and growth hormone releasing factor (GRF). Other preferred open reading frames include those that encode glucagon-like peptides, analogs of glucagon-like peptide-1, analogs of glucagon-like peptide-2, GLP-2(7-36), and analogs of growth hormone releasing factor. Such analogs may be identified by their ability to bind to their respective receptors. For example, an analog of glucagon-like peptide-1 will detectably bind to glucagon-like protein-1 receptor.

One skilled in the art realizes that many open reading frames may be used within an expression cassette or nucleic acid construct of the invention. Examples of such open reading frames include, but are not limited to, open reading frames encoding the polypeptides listed below in Table I.

Suppressible Stop Codon

The expression cassette of the invention may also include a suppressible stop codon. A suppressible stop codon is sometimes referred to as a nonsense mutation. A suppressible stop codon serves as a signal to end translation of an RNA at the location of the suppressible stop codon in the absence of a suppressor. However, in the presence of a suppressor, translation will continue through the suppressible stop codon until another stop codon signals the end of translation of the RNA. Suppressible stop codons and suppressors are known in the art. Sambrook and Russell, Molecular Cloning: A Laboratory Manual, 3rd edition (Jan. 15, 2001) Cold Spring Harbor Laboratory Press, ISBN: 0879695765. Such codons are exemplified by ochre (UAA) and amber (UAG) codons. Suppressible stop codons can be suppressed in cells that encode a tRNA that recognizes the codon and facilitates insertion of an amino acid into the polypeptide chain being translated from the RNA containing the codon. Different cells contain different tRNAs that facilitate insertion of different amino acids into the polypeptide chain at the suppressible stop codon. For example, an amber codon can be suppressed by supD, supE, supF, supB and supC bacterial strains that insert serine, glutamine, tyrosine, glutamine, and tyrosine respectively into a polypeptide. An ochre codon can be suppressed by supB and supC bacterial strains that insert glutamine and tyrosine respectively into a polypeptide chain. Additional suppressible codons and suppressors may be used within the expression cassette of the invention.

Use of a suppressible stop codon in the expression cassette of the invention allows for the production of polypeptides that have a different amino acid inserted at the position coded for by the suppressible stop codon without altering the expression cassette. The use of a suppressible stop codon also allows tandem polypeptides of differing molecular weights to be expressed from the same expression cassette. For example, an expression cassette designed to contain an amber mutation can be expressed in a non-suppressing strain to produce a tandem polypeptide that terminates at the amber codon. The same expression cassette can be expressed in a supE *Escherichia coli* to produce a tandem polypeptide having a glutamine inserted into the fusion polypeptide at the amber mutation. This tandem polypeptide may also include an addition amino acid sequence, such as a fusion tag that is terminated with a second stop codon. An expression cassette of the invention that contains a suppressible stop codon provides for the production of numerous variations of a tandem polypeptide that can be expressed from the same expression cassette. Such tandem polypeptide variations will depend on the combination of the suppressible stop codon used within the expression cassette and the cell in which the expression cassette is inserted.

One or more cleavage agent recognition sites may be introduced into a tandem polypeptide expressed from an expression cassette of the invention through use of an appropriate suppressible stop codon and suppressing cell. For example, a tandem polypeptide can be designed to contain a chymotrypsin cleavage site through use of an expression cassette that encodes the tandem polypeptide and has an amber codon in a supF or supC bacterium such that a tyrosine is inserted into the fusion polypeptide. In another example, a *Neisseria* type 2 IgA protease recognition site can be created through use of an amber containing expression cassette in a supD cell. In yet another example, a recognition site for Plum pox polyvirus Nia protease, Poliovirus 2Apro protease, or Nia Protease (tobacco etch virus) can be created through appropriate use of an expression cassette containing an amber or ochre codon in a supF or a supC cell. Accordingly, an expression cassette of the invention may contain more than one suppressible codon to express a tandem polypeptide that can contain more than one engineered cleavage agent recognition site.

Furthermore, an expression cassette of the invention may be used to express a tandem polypeptide having a preselected amino acid inserted at any position along the polypeptide chain that corresponds to a suppressible stop codon. Briefly, an aminoacyl-tRNA synthetase may be introduced into a cell which specifically acylates a suppressor tRNA with a predetermined amino, acid. An expression cassette containing a suppressible stop codon that may be suppressed by the acylated-tRNA can be expressed in the cell. This will cause a tandem polypeptide to be produced that has the predetermined amino acid inserted into the tandem polypeptide at a position corresponding to the suppressible stop codon. Such a system allows for the design and production of a tandem polypeptide having one or more cleavage agent recognition sites. This in turn allows for the production of tandem polypeptides that can be cleaved by tissue specific proteases. Methods to facilitate the insertion of a specific amino acid into polypeptide chain are known in the art and have been reported. Kowal et al., *Proc. Natl. Acad. Sci. (USA)* 99:2268 (2001).

An expression cassette of the invention may also be used to produce tandem polypeptides having an amino acid analog inserted at any amino acid position. Briefly, a tRNA that is able to suppress a suppressible stop codon is aminoacylated with a desired amino acid analog in vitro according to methods known in the art. The aminoacylated suppressor tRNA can then be imported into a cell containing an expression cassette of the invention. The imported tRNA then facilitates incorporation of the amino acid analog at a position of the tandem polypeptide expressed from the expression cassette at a position corresponding to that of the suppressible stop codon. Such methods may be used with mammalian cells, such as COS1 cells. Kohrer et al., *Proc. Natl. Acad. Sci. (USA)*, 98:14310 (2001).

Fusion Tap

An expression cassette of the invention can optionally express a tandem polypeptide containing a fusion tag. A fusion tag is an amino acid sequence that confers a useful property to the tandem polypeptide. In one example, a fusion tag may be a ligand binding domain that can be used to purify the tandem polypeptide by applying a tandem polypeptide containing the fusion tag to separation media containing the ligand. Such a combination is exemplified by application of a tandem polypeptide containing a glutathione-S-transferase domain to a chromatographic column containing glutathione-linked separation media. In another example, a tandem polypeptide containing a polyhistidine fusion tag may be applied to a nickel column for purification of the tandem polypeptide. In yet another example, a fusion tag can be a ligand. Such a tandem polypeptide can include glutathione as a fusion tag and be applied to a chromatographic column containing glutathione-S-transferase-linked separation media. In still another example, the fusion tag may be an antibody epitope. Such a combination is exemplified by a tandem polypeptide containing maltose binding protein as a fusion tag. Such a tandem polypeptide can be applied to separation media containing an anti-maltose binding protein. Such systems are known in the art and are commercially available. (New England Biolabs, Beverly, Mass.; Stratagene, La Jolla, Calif.). Those of skill in the art realize that numerous fusion tags may incorporated into the expression cassette of the invention.

Termination Sequences

Termination Sequences for Use in Bacteria

Usually, transcription termination sequences recognized by bacteria are regulatory regions located 3' to the translation stop codon, and thus together with the promoter flank the coding sequence. These sequences direct the transcription of an mRNA that can be translated into the polypeptide encoded by the DNA. Transcription termination sequences frequently include DNA sequences of about 50 nucleotides capable of forming stem loop structures that aid in terminating transcription. Examples include transcription termination sequences derived from genes with strong promoters, such as the trp gene in *E. coli* as well as other biosynthetic genes.

Termination Sequences for Use in Mammalian Cells

Usually, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-transcriptional cleavage and polyadenylation (Birnstiel et al., *Cell*, 41:349 (1985); Proudfoot and Whitelaw, "Termination and 3' end processing of eukaryotic RNA", in: Transcription and Splicing (eds. B. D. Hames and D. M. Glover), 1988; Proudfoot, *Trends Biochem. Sci.*, 14:105 (1989)). These sequences direct the transcription of an mRNA that can be translated into the polypeptide encoded by the DNA. Examples of transcription terminator/polyadenylation signals include those derived from SV40 (Sambrook et al., "Expression of cloned genes in cultured mammalian cells", in: Molecular Cloning: A Laboratory Manual, 1989).

Termination Sequences for use in Yeast and Insect Cells

Transcription termination sequences recognized by yeast are regulatory regions that are usually located 3' to the translation stop codon. Examples of transcription terminator sequences that may be used as termination sequences in yeast and insect expression systems are well known. Lopez-Ferber et al., *Methods Mol. Biol.*, 39:25 (1995); King and Possee, The baculovirus expression system. A laboratory guide. Chapman and Hall, London, England (1992); Gregor and Proudfoot, *EMBO J.*, 12:4771 (1998); O'Reilly et al., Baculovirus expression vectors: a laboratory manual. W.H. Freeman & Company, New York, N.Y. (1992); Richardson, *Crit. Rev. Biochem. Mol. Biol.*, 28:1 (1993); Zhao et al., *Microbiol. Mol. Biol. Rev.*, 63:405 (1999).

II. Nucleic Acid Constructs and Expression Cassettes

Nucleic acid constructs and expression cassettes can be created through use of recombinant methods that are well known. (Sambrook and Russell, Molecular Cloning: A Laboratory Manual, 3rd edition (Jan. 15, 2001) Cold Spring Harbor Laboratory Press, ISBN: 0879695765; Ausubel et al., *Current Protocols in Molecular Biology*, Green Publishing Associates and Wiley Interscience, NY (1989)). Generally, recombinant methods involve preparation of a desired DNA fragment and ligation of that DNA fragment into a preselected position in another DNA vector, such as a plasmid.

In a typical example, a desired DNA fragment is first obtained by digesting a DNA that contains the desired DNA fragment with one or more restriction enzymes that cut on both sides of the desired DNA fragment. The restriction enzymes may leave a "blunt" end or a "sticky" end. A "blunt" end means that the end of a DNA fragment does not contain a region of single-stranded DNA. A DNA fragment having a "sticky" end means that the end of the DNA fragment has a region of single-stranded DNA. The sticky end may have a 5' or a 3' overhang. Numerous restriction enzymes are commercially available and conditions for their use are also well known. (USB, Cleveland, Ohio; New England Biolabs, Beverly, Mass.). The digested DNA fragments may be extracted according to known methods, such as phenol/chloroform extraction, to produce DNA fragments free from restriction enzymes. The restriction enzymes may also be inactivated with heat or other suitable means. Alternatively, a desired DNA fragment may be isolated away from additional nucleic acid sequences and restriction enzymes through use of electrophoresis, such as agarose gel or polyacrylamide gel electrophoresis. Generally, agarose gel electrophoresis is used to isolate large nucleic acid fragments while polyacrylamide gel electrophoresis is used to isolate small nucleic acid fragments. Such methods are used routinely to isolate DNA fragments. The electrophoresed DNA fragment can then be extracted from the gel following electrophoresis through use of many known methods, such as electoelution, column chromatography, or binding to glass beads. Many kits containing materials and methods for extraction and isolation of DNA fragments are commercially available. (Qiagen, Venlo, Netherlands; Qbiogene, Carlsbad, Calif.).

The DNA segment into which the fragment is going to be inserted is then digested with one or more restriction enzymes. Preferably, the DNA segment is digested with the same restriction enzymes used to produce the desired DNA fragment. This will allow for directional insertion of the DNA fragment into the DNA segment based on the orientation of the complimentary ends. For example, if a DNA fragment is produced that has an EcoRI site on its 5' end and a BamHI site at the 3' end, it may be directionally inserted into a DNA segment that has been digested with EcoRI and BamHI based on the complimentarity of the ends of the respective DNAs. Alternatively, blunt ended cloning may be used if no convenient restriction sites exist that allow for directional cloning. For example, the restriction enzyme BsaAI leaves DNA ends that do not have a 5' or 3' overhang. Blunt ended cloning may be used to insert a DNA fragment into a DNA segment that was also digested with an enzyme that produces a blunt end. Additionally, DNA fragments and segments may be digested with a restriction enzyme that produces an overhang and then treated with an appropriate enzyme to produce a blunt end. Such enzymes include polymerases and exonucleases. Those of skill in the art know how to use such methods alone or in combination to selectively produce DNA fragments and segments that may be selectively combined.

A DNA fragment and a DNA segment can be combined though conducting a ligation reaction. Ligation links two pieces of DNA through formation of a phosphodiester bond between the two pieces of DNA. Generally, ligation of two or more pieces of DNA occurs through the action of the enzyme ligase when the pieces of DNA are incubated with ligase under appropriate conditions. Ligase and methods and conditions for its use are well known in the art and are commercially available.

The ligation reaction or a portion thereof is then used to transform cells to amplify the recombinant DNA formed, such as a plasmid having an insert. Methods for introducing DNA into cells are well known and are disclosed herein.

Those of skill in the art recognize that many techniques for producing recombinant nucleic acids can be used to produce an expression cassette or nucleic acid construct of the invention. These techniques may be used to isolate individual components of an expression cassette of the invention from existing DNA constructs and insert the components into another piece of DNA to construct an expression cassette. Such techniques can also be used to isolate an expression cassette of the invention and insert it into a desired vector to create a nucleic acid construct of the invention. Additionally, open reading frames may be obtained from genes that are available or are obtained from nature. Methods to isolate and clone genes from nature are known. For example, a desired open reading frame may be obtained through creation of a cDNA library from cells that express a desired polypeptide. The open reading frame may then be inserted into an expression cassette of the invention to allow for production of the encoded preselected polypeptide.

Vectors

Vectors that may be used include, but are not limited to, those able to be replicated in prokaryotes and eukaryotes. For example, vectors may be used that are replicated in bacteria, yeast insect cells, and mammalian cells. Vectors may be exemplified by plasmids, phagemids, bacteriophages, viruses, cosmids, and F-factors. The invention includes any vector into which the expression cassette of the invention may be inserted and replicated in vitro or in vivo. Specific vectors may be used for specific cells types. Additionally, shuttle vectors may be used for cloning and replication in more than one cell type. Such shuttle vectors are known in the art. The nucleic acid constructs may be carried extrachromosomally within a host cell or may be integrated into a host cell chromosome. Numerous examples of vectors are known in the art and are commercially available. (Sambrook and Russell, Molecular Cloning: A Laboratory Manual, 3rd edition (Jan. 15, 2001) Cold Spring Harbor Laboratory Press, ISBN: 0879695765; New England Biolab, Beverly, Mass.; Stratagene, La Jolla, Calif.; Promega, Madison, Wis.; ATCC, Rockville, Md.; CLONTECH, Palo Alto, Calif.; Invitrogen, Carlsbad, Calif.; Origene, Rockville, Md.; Sigma, St Louis, Mo.; Pharmacia, Peapack, N.J.; USB, Cleveland, Ohio). These vectors also provide many promoters and other regulatory elements that those of skill in the art may include within the nucleic acid constructs of the invention through use of known recombinant techniques.

Vectors for Use in Prokaryotes

A nucleic acid construct for use in a prokaryote host, such as a bacteria, will preferably include a replication system allowing it to be maintained in the host for expression or for cloning and amplification. In addition, a nucleic acid construct may be present in the cell in either high or low copy number. Generally, about 5 to about 200, and usually about 10 to about 150 copies of a high copy number nucleic acid construct will be present within a host cell. A host containing a high copy number plasmid will preferably contain at least about 10, and more preferably at least about 20 plasmids. Generally, about 1 to 10, and usually about 1 to 4 copies of a low copy number nucleic acid construct will be present in a host cell. The copy number of a nucleic acid construct may be controlled by selection of different origins of replication according to methods known in the art. Sambrook and Russell, Molecular Cloning: A Laboratory Manual, 3rd edition (Jan. 15, 2001) Cold Spring Harbor Laboratory Press, ISBN: 0879695765.

A nucleic acid construct containing an expression cassette can be integrated into the genome of a bacterial host cell through use of an integrating vector. Integrating vectors usually contain at least one sequence that is homologous to the bacterial chromosome that allows the vector to integrate. Integrations are thought to result from recombinations between homologous 1 DNA in the vector and the bacterial chromosome. For example, integrating vectors constructed with DNA from various *Bacillus* strains integrate into the *Bacillus* chromosome (EPO Publ. No. 127 328). Integrating vectors may also contain bacteriophage or transposon sequences.

Extrachromosomal and integrating nucleic acid constructs may contain selectable markers to allow for the selection of bacterial strains that have been transformed. Selectable markers can be expressed in the bacterial host and may include genes which render bacteria resistant to drugs such as ampicillin, chloramphenicol, erythromycin, kanamycin (neomycin), and tetracycline (Davies et al., *Ann. Rev. Microbiol.* 32:469 (1978)). Selectable markers may also include biosynthetic genes, such as those in the histidine, tryptophan, and leucine biosynthetic pathways.

Numerous vectors, either extra-chromosomal or integrating vectors, have been developed for transformation into many bacteria. For example, vectors have been developed for the following bacteria: *B. subtilis* (Palva et al., *Proc. Natl. Acad. Sci. USA,* 79:5582 (1982)); EPO Publ. Nos. 036 259 and 063 953; PCT Publ. No. WO 84/04541), *E. coli* (Shimatake et al., *Nature,* 222:128 (1981); Amann et al. Gene, 40:183 (1985): Studier et al. *J. Mol. Biol.,* 189:113 (1986); EPO Publ. Nos. 036 776, 136 829 and 136 907), *Streptococcus cremoris* (Powell et al., *Appl. Environ. Microbiol.,* 54: 655 (1988)); *Streptococcus lividans* (Powell et al., *Appl. Environ. Microbiol.,* 54:655 (1988)), and *Streptomyces lividans* (U.S. Pat. No. 4,745,056). Numerous vectors are also commercially available (New England Biolabs, Beverly, Mass.; Stratagene, La Jolla, Calif.).

Vectors for Use in Yeast

Many vectors may be used to construct a nucleic acid construct that contains an expression cassette of the invention and mat provides for the expression of a tandem polypeptide in yeast. Such vectors include, but are not limited to, plasmids and yeast artificial chromosomes. Preferably the vector has two replication systems, thus allowing it to be maintained, for example, in yeast for expression and in a prokaryotic host for cloning and amplification. Examples of such yeast-bacteria shuttle vectors include YEp24 (Botstein, et al., *Gene,* 8:17 (1979)), pCl/1 (Brake et al., *Proc. Natl. Acad. Sci. USA.* 81:4642 (1984)), and YRp17 (Stinchcomb et al., *J. Mol. Biol.* 158:157 (1982)). A vector may be maintained within a host cell in either high or low copy number. For example, a high copy number plasmid will generally have a copy number ranging from about 5 to about 200, and usually about 10 to about 150. A host containing a high copy number plasmid will preferably have at least about 10, and more preferably at least about 20. Either a high or low copy number vector may be selected, depending upon the effect of the vector and the tandem polypeptide on the host (Brake et al., *Proc. Natl. Acad. Sci. USA* 81:4642 (1984)).

A nucleic acid construct may also be integrated into the yeast genome with an integrating vector. Integrating vectors usually contain at least one sequence homologous to a yeast chromosome that allows the vector to integrate, and preferably contain two homologous sequences flanking an expression cassette of the invention. Integrations appear to result from recombinations between homologous DNA in the vector and the yeast chromosome, (Orr-Weaver et al., *Methods in Enzymol.,* 101:228 (1983)). An integrating vector may be directed to a specific locus in yeast by selecting the appropriate homologous sequence for inclusion in the vector. One or more nucleic acid constructs may integrate, which may affect the level of recombinant protein produced. (Rine et al. *Proc. Natl. Acad. Sci. USA,* 80:6750 (1983)). The chromosomal sequences included in the vector can occur either as a single segment in the vector, which results in the integration of the entire vector, or two segments homologous to adjacent segments in the chromosome and flanking an expression cassette included in the vector, which can result in the stable integration of only the expression cassette.

Extrachromosomal and integrating nucleic acid constructs may contain selectable markers that allow for selection of yeast strains that have been transformed. Selectable markers may include, but are not limited to, biosynthetic genes that can be expressed in the yeast host, such as ADE2, HES4, LEU2, TRP1, and ALG7, and the G418 resistance gene, which confer resistance in yeast cells to tunicamycin and G418, respectively. In addition, a selectable marker may also provide yeast with the ability to grow in the presence of toxic compounds, such as metal. For example, the presence of CUP1 allows yeast to grow in the presence of copper ions. (Butt et al., *Microbiol. Rev.* 51:351 (1987)).

Many vectors have been developed for transformation into many yeasts. For example, vectors have been developed for the following yeasts: *Candida albicans* (Kurtz et al., *Mol. Cell. Biol.,* 6:142 (1986)), *Candida maltose* (Kunze et al., *J. Basic Microbiol.,* 25:141 (1985)), *Hansenula polymorpha* (Gleeson et al., *J. Gen. Microbiol.,* 132:3459 (1986); Roggenkamp et al., *Mol. Gen. Genet.,* 202:302 (1986), *kluyveromyces fragilis* (Das et al., *J. Bacteriol.,* 158: 1165 (1984)), *Kluyveromyces lactis* (De Louvencourt et al., *J. Bacteriol.,* 154:737 (1983); van den Berg et al., *Bio/Technology,* 8:135 (1990)), *Pichia guillerimondii* (Kunze et al., *J. Basic Microbiol.* 25:141 (1985)), *Pichia pastoris* (Cregg et al., *Mol. Cell. Biol.,* 5: 3376, 1985; U.S. Pat. Nos. 4,837,148 and 4,929,555), *Saccharomyces cerevisiae* (Hinnen et al., *Proc. Natl. Acad. Sci. USA.* 75:1929 (1978); Ito et al., *J. Bacteriol.,* 153:163 (1983)), *Schizosaccharomyces pombe* (Beach and Nurse, *Nature,* 300:706 (1981)), and *Yarrowia lipolytica* (Davidow et al., *Curr. Genet.,* 10:39 (1985); Gaillardin et al., *Curr. Genet.,* 10:49 (1985)).

Vectors for Use in Insect Cells

Baculovirus vectors have been developed for infection into several insect cells and may be used to produce nucleic acid constructs that contain an expression cassette of the invention. For example, recombinant baculoviruses have been developed for *Aedes aegypti, Autographa californica, Bombyx mori, Drosophila melanogaster, Spodoptera frugiperda,* and *Trichoplusia ni* (PCT Pub. No. WO 89/046699; Carbonell et al., *J. Virol.,* 56:153 (1985); Wright, *Nature.,* 321: 718 (1986); Smith et al., *Mol. Cell. Biol.,* 2: 2156 (1983); and see generally, Fraser et al., *In Vitro Cell Dev. Biol.* 25:225 (1989)). Such a baculovirus vector may be used to introduce an expression cassette into an insect and provide for the expression of a tandem polypeptide within the insect cell.

Methods to form a nucleic acid construct having an expression cassette of the invention inserted into a baculovirus vector are well known in the art. Briefly, an expression cassette of the invention is inserted into a transfer vector, usually a bacterial plasmid that contains a fragment of the baculovirus genome, through use of common recombinant methods. The plasmid may also contain a polyhedrin polyadenylation signal (Miller et al., *Ann. Rev. Microbiol.,* 42:177 (1988)) and a prokaryotic selection marker, such as ampicillin resistance, and an origin of replication for selection and propagation in *Escherichia coli.* A convenient transfer vector for introducing foreign genes into AcNPV is pAc373. Many other vectors, known to those of skill in the art, have been designed. Such a vector is pVL985 (Luckow and Summers, *Virology.* 12-31 (1989)).

A wild-type baculoviral genome and the transfer vector having an expression cassette insert are transfected into an insect host cell where the vector and the wild-type viral genome recombine. Methods for introducing an expression cassette into a desired site in a baculovirus virus are known in the art. (Summers and Smith, Texas Agricultural Experiment Station Bulletin No. 1555, 1987. Smith et al., *Mol. Cell. Biol.,* 3:2156 (1983); and Luckow and Summers, *Virology,* 17:31 (1989)). For example, the insertion can be into a gene such as the polyhedrin gene, by homologous double crossover recombination; insertion can also be into a restriction enzyme site engineered into the desired baculovirus gene (Miller et al., *Bioessays,* 4:91 (1989)). The expression cassette, when cloned in place of the polyhedrin gene in the nucleic acid construct, will be flanked both 5' and 3' by polyhedrin-specific sequences. An advantage of inserting an expression cassette into the polyhedrin gene is that occlusion bodies resulting from expression of the wild-type polyhedrin gene may be eliminated. This may decrease contamination of tandem polypeptides produced through expression and formation of occlusion bodies in insect cells by wild-type proteins that would otherwise form occlusion bodies in an insect cell having a functional copy of the polyhedrin gene.

The packaged recombinant virus is expressed and recombinant plaques are identified and purified. Materials and methods for baculovirus and insect cell expression systems are commercially available in kit form. (Invitrogen, San Diego, Calif., USA ("MaxBac" kit)). These techniques are generally known to those skilled in the art and fully described in Summers and Smith, Texas Agricultural Experiment Station Bulletin No. 1555, 1987.

Plasmid-based expression systems have also been developed that may be used to introduce an expression cassette of the invention into an insect cell and produce a tandem polypeptide. (McCarroll and King, *Curr. Opin. Biotechnol.,* 8:590 (1997)). These plasmids offer an alternative to the production of a recombinant virus for the production of tandem polypeptides.

Vectors for Use in Mammalian Cells

An expression cassette of the invention may be inserted into many mammalian vectors that are known in the art and are commercially available. (CLONTECH, Palo Alto, Calif.; Promega, Madison, Wis.; Invitrogen, Carlsbad, Calif.). Such vectors may contain additional elements such as enhancers and introns having functional splice donor and acceptor sites. Nucleic acid constructs may be maintained extrachromosomally or may integrate in the chromosomal DNA of a host cell. Mammalian vectors include those derived from animal viruses, which require trans-acting factors to replicate. For example, vectors containing the replication systems of papovaviruses, such as SV40 (Gluzman, *Cell,* 23:175 (1981)) or polyomaviruses, replicate to extremely high copy number in the presence of the appropriate viral T antigen. Additional examples of mammalian vectors include those derived from bovine papillomavirus and Epstein-Barr virus. Additionally, the vector may have two replication systems, thus allowing it to be maintained, for example, in mammalian cells for expression and in a prokaryotic host for cloning and amplification. Examples of such mammalian-bacteria shuttle vectors include pMT2 (Kaufman et al., *Mol. Cell. Biol.,* 9:946 (1989)) and pHEBO (Shimizu et al., *Mol. Cell. Biol.,* 6:1074 (1986).

III. Cells Containing an Expression Cassette or a Nucleic Acid Construct

The invention provides cells that contain an expression cassette of the invention or a nucleic acid construct of the invention. Such cells may be used for expression of a preselected polypeptide. Such cells may also be used for the amplification of nucleic acid constructs. Many cells are suitable for amplifying nucleic acid constructs and for expressing preselected polypeptides. These cells may be prokaryotic or eukaryotic cells.

In a preferred embodiment, bacteria are used as host cells. Examples of bacteria include, but are not limited to, Gram-negative and Gram-positive organisms. *Escherichia coli* is a preferred organism for expression of preselected polypeptides and amplification of nucleic acid constructs. Many publically available *E. coli* strains include Restrains such as MM294 (ATCC 31, 466); X1776 (ATCC 31, 537); KS 772 (ATCC 53, 635); JM109; MC1061; HMS174; and the B-strain BL21. Recombination minus strains may be used for nucleic acid construct amplification to avoid recombination events. Such recombination events may remove concatamers of open reading frames as well as cause inactivation of an expression cassette. Furthermore, bacterial strains that do not express a select protease may also be useful for expression of preselected polypeptides to reduce proteolytic processing of expressed polypeptides. Such a strain is exemplified by Y1090hsdR which is deficient in the lon protease.

Eukaryotic cells may also be used to produce a preselected polypeptide and for amplifying a nucleic acid construct. Eukaryotic cells are useful for producing a preselected polypeptide when additional cellular processing is desired. For example, a preselected polypeptide may be expressed in a eukaryotic cell when glycosylation of the polypeptide is desired. Examples of eukaryotic cell lines that may be used include, but are not limited to: AS52, H187, mouse L cells, NIH-3T3, HeLa, Jurkat, CHO-K1, COS-7, BHK-21, A-431, HEK293, L6, CV-1, HepG2, HC11, MDCK, silkworm cells, mosquito cells, and yeast.

Methods for introducing exogenous DNA into bacteria are well known in the art, and usually include either the transformation of bacteria treated with $CaCl_2$ or other agents, such as divalent cations and DMSO. DNA can also be introduced into bacterial cells by electroporation, use of a bacteriophage, or ballistic transformation. Transformation procedures usually vary with the bacterial species to be transformed (Masson et al., *FEMS Microbiol. Lett.,* 60:273 (1989); Palva et al., *Proc. Natl. Acad. Sci. USA.,* 72:5582 (1982); EPO Publ. Nos. 036 259 and 063 953; PCT Publ. No. WO 84/04541 *[Bacillus]*, Miller et al. *Proc. Natl. Acad. Sci. USA.,* 8:856 (1988): Wang et al. *J. Bacteriol.* 172:949 (1990) *[Campylobacter]*, Cohen et al., *Proc. Natl. Acad. Sci. USA.,* 69:2110 (1973); Dower et al., *Nuc. Acids Res.,* 16:6127 (1988); Kushner, "An improved method for transformation of *Escherichia coli* with ColE1-derived plasmids", in: Genetic Engineering: Proceedings of the International Symposium on Genetic Engineering (eds. H. W. Boyer and S. Nicosia), 1978; Mandel et al., *J. Mol. Biol.,* 53:159 (1970); Taketo, *Biochim. Biophys. Acta.,* 949:318 (1988) *[Escherichia]*, Chassy et al., *FEMS Microbiol. Lett.,* 44:173 (1987) *[Lactobacillus]*, Fiedler et al., *Anal. Biochem.,* 170:38 (1988) *[Pseudomonas]*, Augustin et al., *FEMS Microbiol. Lett.,* 66:203 (1990) *[Staphylococcus]*, Barany et al., *J. Bacteriol.,* 144:698 (1980); Harlander, "Transformation of *Streptococcus lactis* by electroporation", in: *Streptococcal Genetics* (ed. J. Ferretti and R. Curtiss III), 1987; Perry et al., *Infec. Immun.,* 32:1295 (1981); Powell et al., *Appl. Environ. Microbiol.* 54:655 (1988); Somkuti et al., *Proc. 4th Eur. Cong. Biotechnology,* 1:412 (1987) *[Streptococcus]*).

Methods for introducing exogenous DNA into yeast hosts are well known in the art, and usually include either the transformation of spheroplasts or of intact yeast cells treated with alkali cations. Transformation procedures usually vary with the yeast species to be transformed (see, e.g., Kurtz et al., *Mol. Cell. Biol.,* 6:142 (1986); Kunze et al., *J. Basic Microbiol.,* 25:141 (1985) *[Candida]*, Gleeson et al., *J. Gen. Microbiol.,* 132:3459 (1986); Roggenkamp et al., *Mol. Gen. Genet.,* 202:302 (1986) *[Hansenula]*, Das et al., *J. Bacteriol.,* 158: 1165 (1984); De Louvencourt et al., *J. Bacteriol.,* 754:737 (1983); Van den Berg et al., *Bio/Technology,* 8:135 (1990) *[Kluyveromyces]*, Cregg et al., *Mol. Cell. Biol.,* 5:3376 (1985); Kunze et al., *J. Basic Microbiol.,* 25:141 (1985); U.S. Pat. Nos. 4,837,148 and 4,929,555 *[Pichia]*, Hinnen et al., *Proc. Natl. Acad. Sci. USA,* 25:1929 (1978); Ito et al., *J. Bacteriol.,* 153:163 (1983) *[Saccharomyces]*, Beach and Nurse, *Nature,* 300:706 (1998) *[Schizosaccharomyces]*, and Davidow et al., *Curr. Genet.*, 10:39 (1985); Gaillardin et al., *Curr. Genet.*, 10:49 (1985) [*Yarrowia*]).

Exogenous DNA is conveniently introduced into insect cells through use of recombinant viruses, such as the baculoviruses described herein.

Methods for introduction of heterologous polynucleotides into mammalian cells are known in the art and include lipid-mediated transfection, dextran-mediated transfection, calcium phosphate precipitation, polybrene-mediated transfection, protoplast fusion, electroporation, encapsulation of the polynucleotide(s) in liposomes, biollistics, and direct microinjection of the DNA into nuclei. The choice of method depends on the cell being transformed, as certain transformation methods are more efficient with one type of cell than another. (Feigner et al., *Proc. Natl. Acad. Sci.*, 154:7413 (1987); Feigner et al., *J. Biol. Chem.*, 269:2550 (1994); Graham and van der Eb, *Virology*, 52:456 (1973); Vaheri and Pagano, *Virology*, 27:434 (1965); Neuman et al., *EMBO J.*, 1:841 (1982); Zimmerman, *Biochem. Biophys. Acta.*, 694: 227 (1982); Sanford et al. *Methods Enzymol.*, 217:483 (1993); Kawai and Nishizawa, *Mol. Cell. Biol.*, 4:1172 (1984); Chanev et al. *Somat. Cell Mol. Genet.*, 12:237 (1986): Aubin et al. *Methods Mol. Biol.*, 62:319 (1997)). In addition, many commercial kits and reagents for transfection of eukaryotic are available.

Following transformation or transfection of a nucleic acid into a cell, the cell may be selected for through use of a selectable marker. A selectable marker is generally encoded on the nucleic acid being introduced into the recipient cell. However, co-transfection of selectable marker can also be used during introduction of nucleic acid into a host cell. Selectable markers that can be expressed in the recipient host cell may include, but are not limited to, genes which render the recipient host cell resistant to drugs such as actinomycin $C_1$, actinomycin D, amphotericin, ampicillin, bleomycin, carbenicillin, chloramphenicol, geneticin, gentamycin, hygromycin B, kanamycin monosulfate, methotrexate, mitomycin C, neomycin B sulfate, novobiocin sodium salt penicillin G sodium salt, puromycin dihydrochloride, rifampicin, streptomycin sulfate, tetracycline hydrochloride, and erythromycin. (Davies et al., *Ann. Rev. Microbiol.*, 32:469, 1978). Selectable markers may also include biosynthetic genes, such as those in the histidine, tryptophan, and leucine biosynthetic pathways. Upon transfection or transformation of a host cell, the cell is placed into contact with an appropriate selection marker.

For example, if a bacterium is transformed with a nucleic acid construct that encodes resistance to ampicillin, the transformed bacterium may be placed on an agar plate containing ampicillin. Thereafter, cells into which the nucleic acid construct was not introduced would be prohibited from growing to produce a colony while colonies would be formed by those bacteria that were successfully transformed. An analogous system may be used to select for other types of cells, including both prokaryotic and eukaryotic cells.

IV. Tandem Polypeptides

The invention provides numerous tandem polypeptides that include a preselected polypeptide operably linked to an inclusion body fusion partner that causes the tandem polypeptide to form inclusion bodies having useful isolation enhancement characteristics. In one embodiment, tandem polypeptides can include an inclusion body fusion partner that is operably linked to a preselected polypeptide. The inclusion body fusion partner may be linked to the amino-terminus or the carboxyl-terminus of the preselected polypeptide. In another embodiment, a tandem polypeptide can have an inclusion body fusion partner operably linked to both the amino-terminus and the carboxyl-terminus of a preselected polypeptide. A tandem polypeptide may also include multiple copies of an inclusion body fusion partner. In other embodiments, a tandem polypeptide can have additional amino acid sequences in addition to an inclusion body fusion partner and a preselected polypeptide. For example, a tandem polypeptide may contain one or more cleavable peptide linkers, fusion tags, and preselected polypeptides. Cleavable peptide linkers can be operably linked between an inclusion body fusion partner and a preselected polypeptide, between a preselected polypeptide and a fusion tag, between multiple copies of a preselected polypeptide, or any combination thereof. Also cleavable peptide linkers that are cleaved by different cleavage agents can be operably linked within a single tandem polypeptide. In additional embodiments, a tandem polypeptide can include one or more fusion tags.

The tandem polypeptide can have numerous preselected polypeptides operably linked to an inclusion body fusion partner. Preferably the preselected polypeptide is a bioactive polypeptide. Examples of such polypeptides are GLP-1, GLP-2, PTH, GRF, and active forms thereof.

V. Method to Produce a Tandem Polypeptide

Methods to produce a tandem polypeptide are provided by the invention. The methods involve using an expression cassette of the invention to produce a tandem polypeptide. A tandem polypeptide can be produced in vitro through use of an in vitro transcription and translation system, such as a rabbit reticulocyte lysate system, Preferably a tandem polypeptide is expressed within a cell into which an expression cassette encoding the tandem polypeptide has been introduced.

Generally, cells having an expression cassette integrated into their genome or which carry an expression cassette extrachromosomally are grown to high density and then induced. Following induction, the cells are harvested and the tandem polypeptide is isolated. Such a system is preferred when an expression cassette includes a repressed promoter. This type of system is useful when a tandem polypeptide contains a preselected polypeptide that is toxic to the cell. Examples of such preselected polypeptides include proteases and other polypeptides that interfere with cellular growth. The cells can be induced by many art recognized methods that include, but are not limited to, heat shift, addition of an inducer such as IPTG, or infection by a virus or bacteriophage that causes expression of the expression cassette.

Alternatively, cells that carry an expression cassette having a constitutive promoter do not need to be induced as the promoter is always active. In such systems, the cells are allowed to grow until a desired quantity of tandem polypeptide is produced and then the cells are harvested.

Methods and materials for the growth and maintenance of many types of cells are well known and are available commercially. Examples of media that may be used include, but are not limited to: YEPD, IB, TB, 2xYT, GYT, M9, NZCYM, NZYM, NZN, SOB, SOC, Alsever's solution, CHO medium, Dulbecco's Modified Eagle's Medium, and HBSS. (Sigma, St. Louis, Mo.; Sambrook and Russell, Molecular Cloning: A Laboratory Manual, 3rd edition (Jan. 15, 2001) Cold Spring Harbor Laboratory Press, ISBN: 0879695765; Summers and Smith, Texas Agricultural Experiment Station Bulletin No. 1555, (1987)).

Tables

TABLE I

Amino acid sequences of inclusion body fusion partner examples

| Name | Amino Acid Sequences | SEQ ID NO: |
|---|---|---|
| IBFP1 | GSGQGQAQYLSASCVVFTNYSGDTASQVD | 1 |
| IBFP2 | GSGQGQAQYLAASLVVFTNYSGDTASQVD | 2 |
| IBFP3 | GSQYLAASLVVFTNYSGDTASQVD | 3 |
| IBFP4 | GSGQGQAQYLAASLVVFTNYSGD | 4 |
| IBFP5 | GSQYLAASLVVFTNYSGD | 5 |
| IBFP6 | GSQYLAAVLVVFTNYSGDTASQVD | 6 |
| IBFP7 | GSGQGQAQYLTASLVKFTNYSGDTASQVD | 7 |
| IBFP8 | GSGQGQAQYLTASLVQFTNYSGDTASQVD | 8 |
| IBFP9 | GSGQGQAQYLPASLVKFTNYSGDTASQVD | 9 |
| IBFP10 | GSGQGQAQYLPASLVQFTNYSGDTASQVD | 10 |
| IBFP11 | GSGQGQAQYLAASLVKFTNYSGDTASQVD | 11 |
| IBFP12 | GSGQGQAQYLAASLVQFTNYSGDTASQVD | 12 |
| IBFP13 | GSGQGQAQYLSASLVKFTNYSGDTASQVD | 13 |
| IBFP14 | GSGQGQAQYLSASLVQETNYSGDTASQVD | 14 |
| IBFP15 | GSGQGQAQYLAAVLVVETNYSGDTASQVD | 15 |

TABLE II

Nucleic acid sequences of inclusion body fusion partner examples

| Name | Nucleic Acid Sequences | SEQ ID NO: |
|---|---|---|
| IBFP1 | GGC AGT GGC CAG GGA CAG GCT CAA TAT CTA TCG GCC TCC TGC GTT GTG TTC ACC AAC TAC TCG GGC GAC ACG GCC AGC CAG GTG GAC | 16 |
| IBFP2 | GGA TCC GGC CAG GGA CAG GCT CAA TAT CTA GCG GCC TCC TTG GTT GTG TTC ACC AAC TAC TCG GGC GAC ACG GCC AGC CAG GTG GAC | 17 |
| IBFP3 | GGA TCC GGC CAG GGT CAG GCT CAA TAT CTG GCT GCC TCC CTG GTT GTG TTC ACC AAC TAC TCG GGC GAC ACG GCC AGC CAG GTG GAC | 18 |
| IBFP4 | GGA TCC GGC CAG GGT CAG GCT CAA TAT CTG GCT GCC TCC CTG GTT GTG TTC ACC AAC TAC TCG GCC GAC | 19 |
| IBFP5 | GGA TCC CAA TAT CTG GCT GCC TCC CTG GTT GTG TTC ACC AAC TAC TCG GGC GAC | 20 |
| IBFP6 | GGA TCC CAA TAT CTG GCT GCC GTG CTG GTT GTG TTC ACC AAC TAC TCG GGC GAC ACG GCC AGC CAG GTG GAC | 21 |
| IBFP7 | GGA TCC GGC CAG GGT CAG GCT CAA TAT CTG ACG GCC TCC CTG GTT AAA TTC ACC AAC TAC TCG GGC GAC ACG GCC AGC CAG GTG GAC | 22 |
| IBFP8 | GGA TCC GGC CAG GGT CAG GCT CAA TAT CTG ACG GCC TCC CTG GTT CAA TTC ACC AAC TAC TCG GGC GAC ACG GCC AGC CAG GTG GAC | 23 |
| IBFP9 | GGA TCC GGC CAG GGT CAG GCT CAA TAT CTG CCG GCC TCC CTG GTT AAA TTC ACC AAC TAC TCG GGC GAC AGC GCC AGC CAG GTG GAC | 24 |
| IBFP10 | GGA TCC GGC CAG GGT CAG GCT CAA TAT CTG CCG GCC TCC CTG GTT CAA TTC ACC AAC TAC TCG GGC GAC ACG GCC AGC CAG GTG GAC | 25 |
| IBFP11 | GGA TCC GGC CAG GGT CAG GCT CAA TAT CTG GCG GCC TCC CTG GTT AAA TTC AAG TAC TCG GGC GAC ACG GCC AGC CAG GTG GAC | 26 |
| IBFP12 | GGA TCC GGC CAG GGT CAG GCT CAA TAT CTG GCG GCC TCC CTG GTT CAA TTC ACC AAC TAC TCG GGC GAC ACG GCC AGC CAG GTG GAC | 27 |
| IBFP13 | GGA TCC GGC CAG GGT CAG GCT CAA TAT CTG TCG GCC TCC CTG GTT AAA TTC ACC AAC TAC TCG GGC GAC ACG GCC AGC CAG GTG GAC | 28 |
| IBFP14 | GGA TCC GGC CAG GGT CAG GCT CAA TAT CTG TCG GCC TCC CTG GTT CAA TTC ACC AAC TAC TCG GGC GAC ACG GCC AGC CAG GTG GAC | 29 |
| IBFP15 | GGA TCC GGC CAG GGT CAG GCT CAA TAT CTG GCT GCC GTG CTG GTT GTG TTC ACC AAC TAC TCG GGC GAC ACG GCC AGC CAG GTG GAC | 30 |

TABLE III

Amino acid sequences and modifications of preselected polypeptide examples

| Name | Amino Acid Sequences | SEQ ID NO: |
|---|---|---|
| GLP-1(7-36) | HAEGTFTSDVSSYLEGQAAKEFIAWLVKGR | 31 |
| GLP-1(7-36) NH$_2$ | HAEGTFTSDVSSYLEGQAAKEFIAWLVKGR-NH$_2$ | 31 |

TABLE III-continued

Amino acid sequences and modifications of preselected polypeptide examples

| Name | Amino Acid Sequences | SEQ ID NO: |
|---|---|---|
| GLP-1 (7-37) | HAEGTFTSDVSSYLEGQAAKEFIAWLVKGRG | 32 |
| GLP-1(7-37) NH$_2$ | HAEGTFTSDVSSYLEGQAAKEFIAWLVKGRG-NH$_2$ | 32 |
| GLP-1(7-36) K26R | HAEGTFTSDVSSYLEGQAAREFIAWLVKGR | 33 |
| GLP-1(7-36) K26R-NH$_2$ | HAEGTFTSDVSSYLEGQAAREFIAWLVKGR-NH$_2$ | 33 |
| GLP-1(7-37) K26R | HAEGTFTSDVSSYLEGQAAREFIAWLVKGRG | 34 |
| GCLP1(7-37) K26R-NH$_2$ | HAEGTFTSDVSSYLEGQAAREFIAWLVKGRG-NH$_2$ | 34 |
| GLP-2(1-34) | HADGSFSDGMNTILDNLAARDFINWLIQTKITDR | 35 |
| GLP-2(1-34)-NH$_2$ | HADGSFSDGMNTILDNLAARDFINWLIQTKTDR-NH$_2$ | 35 |
| GLP-2(1-33) | HADGSFSDGMNTILDNLAARDFINWLIQTKITD | 36 |
| GLP-2(1-33)-NH$_2$ | HADGSFSDGMNTILDNLAARDFINWLIQTKITD-NH$_2$ | 36 |
| GLP-2(1-33) A2G | HGDGSFSDGMNTILDNLAARDFINWLIQTKITD | 37 |
| GLP-2(1-33) A2G-NH$_2$ | HGDGSFSDGMNTILDNLAARDFINWLIQTKITD-NH$_2$ | 37 |
| GLP-2(1-34) A2G | HGDGSFSDGMNTILDNLAARDFINWLIQTKITDR | 38 |
| GLP-2(1-34)A2G-NH$_2$ | HGDGSFSDGMNTILDNLAARDFINWLIQTKITDR-NH$_2$ | 38 |
| GRF(1-44) | YADAIFTNSYRKVLGQLSARKLLQDIMSRQQGESNQERGARARL | 39 |
| PTH(1-34) | SVSEIQLMHNLGKHLNSMERVEWLRKKLQDVHNF | 40 |
| PTH(1-37) | SVSEIQLMHNLGKHLNSMERVEWLRKKLQDVHNFVAL | 41 |
| PTH(1-84) | SVSEIQLMHNLGKHLNSMERVEWLRKKLQDVHNFVALGAPLAPRDAGSQRPRKKEDNVLVESHEKSLGEADKADVNVLTKAKSQ | 42 |
| Amyloid P Component (27-38) Amide | H-Glu-Lys-Pro-Leu-Gln-Asn-Phe-Thr-Leu-Cys-Phe-Arg-NH$_2$ | 43 |
| (TyrO)-Fibrinopeptide A | H-Tyr-Ala-Asp-Ser-Gly-Glu-Gly-Asp-Phe-Leu-Ala-Glu-Gly-Gly-Gly-Val-Arg-OH | 44 |
| Urechistachykinin II | H-Ala-Ala-Gly-Met-Gly-Phe-Phe-Gly-Ala-Arg-NH$_2$ | 45 |
| Amyloid β-Protein (12-28) | H-Val-His-His-Gln-Lys-Leu-Val-Phe-Phe-Ala-Glu-Asp-Val-Gly-Ser-Asn-Lys-OH | 46 |
| Amyloid β-Protein (22-35) | H-Glu-Asp-Val-Gly-Ser-Asn-Lys-Gly-Ala-Ile-Ile-Gly-Leu-Met-OH | 47 |

TABLE III-continued

Amino acid sequences and modifications of preselected polypeptide examples

| Name | Amino Acid Sequences | SEQ ID NO: |
|---|---|---|
| β-Endorphin (camel) | H-Tyr-Gly-Phe-Met-Thr-Ser-Glu-Lys-Ser-Gln-Thr-Pro-Leu-Val-Thr-Leu-Phe-Lys-Asn-Ala-Ile-Ile-Lys-Asn-Ala-His-Lys-Gly-Gln-OH | 48 |
| Valosin (porcine) | H-Val-Gln-Tyr-Pro-Val-Glu-His-Pro-Asp-Lys-Phe-Leu-Lys-Phe-Gly-Met-Thr-Pro-Ser-Lys-Gly-Val-Leu-Phe-Tyr-OH | 49 |
| Vasoactive Intestinal Contractor Peptide (mouse) | H-Cys-Ser-Cys-Asn-Ser-Trp-Lou-Asp-Lys-Glu-Cys-Val-Tyr-Phe-Cys-His-Leu-Asp-Ile-Ile-Trp-OH | 50 |

TABLE IV

Nucleic acid sequences of preselected polypetide examples

| Name | Nucleic Acid Sequences | SEQ ID NO: |
|---|---|---|
| GLP-1(7-36) | CAT GCT GAG GGT ACC TTC ACC TCC GAC GTT TCC TCC TAC CTG GAA GGT CAG GCT GCT AAA GAA TTC ATC GCT TGG CTG GTT AAA GGT CGT | 51 |
| GLP-1(7-36)-NH$_2$ | CAT GCT GAG GGT ACC TTC ACC TCC GAC GTT TCC TCC TAC CTG GAA GGT CAG GCT GCT AAA GAA TTC ATC GCT TGG CTG GTT AAA GGT CGT | 51 |
| GLP-1(7-37) | CAT GCT GAG GGT ACC TTC ACC TCC GAC GTT TCC TCC TAC CTG GAA GGT CAG GCT GCT AAA GAA TTC ATC GCT TGG CTG GTT AAA GGT CGT GGT | 52 |
| GLP-1(7-37)-NH$_2$ | CAT GCT GAG GGT ACC TTC ACC TCC GAC GTT TCC TCC TAC CTG GAA GGT CAG GCT GCT AAA GAA TTC ATC GCT TGG CTG GTT AAA GGT CGT GGT | 52 |
| GLP-1(7-36) K26R | CAT GCT GAG GGT ACC TTC ACC TCC GAC GTT TCC TCC TAC CTG GAA GGT CAG GCT GCT CGT GAA TTC ATC GCT TGG CTG GTT AAA GGT CGT | 53 |
| GLP-1(7-36)K26R-NH$_2$ | CAT GCT GAG GGT ACC TTC ACC TCC GAC GTT TCC TCC TAC CTG GAA GGT CAG GCT GCT CGT GAA TTC ATC GCT TGG CTG GTT AAA GGT CGT | 53 |
| GLP-1(7-37)K26R | CAT GCT GAG GGT ACC TTC ACC TCC GAC GTT TCC TCC TAC CTG GAA GGT CAG GCT GCT CGT GAA TTC ATC GCT TGG CTG GTT AAA GGT CGT GGT | 54 |
| GLP-1(7-37)K26R-NH$_2$ | CAT GCT GAG GGT ACC TTC ACC TCC GAC GTT TCC TCC TAC CTG GAA GGT CAG GCT GCT CGT GAA TTC ATC GCT TGG CTG GTT AAA GGT CGT GGT | 54 |
| GLP-2(1-34) | CAT GCT GAT GGT TCT TTC TCT GAT GAG ATG AAC ACC ATT CTT GAT AAT CTT GCC GCC CGT GAC TTT ATC AAC TGG TTG ATT CAG ACC AAA ATC ACT GAC CGT | 55 |
| GLP-2(1-34)-NH$_2$ | CAT GCT GAT GGT TCT TTC TCT GAT GAG ATG AAC ACC ATT CTT GAT AAT CTT GCC GCC CGT GAC TTT ATC AAC TGG TTG ATT CAG ACC AAA ATC ACT GAC CGT | 55 |

| | | |
|---|---|---|
| GLP-2(1-33) | CAT GCT GAT GGT TCT TTC TCT GAT GAG ATG AAC ACC ATT CTT GAT AAT CTT GCC GCC CGT GAC TTT ATC AAC TGG TTG ATT CAG ACC AAA ATC ACT GAC | 56 |
| GLP-2(1-33)-NH$_2$ | CAT GCT GAT GGT TCT TTC TCT GAT CAG ATG AAC ACC ATT CTT GAT AAT CTT GCC GCC CGT GAC TTT ATC AAC TGG TTG ATT CAG ACC AAA ATC ACT GAC | 56 |
| GLP-2(1-33)A2G | CAT GGT GAT GGT TCT TTC TCT GAT GAG ATG AAC ACC ATT CTT GAT AAT CTT GCC GCC CGT GAC TTT ATC AAC TGG TTG ATT CAG ACC AAA ATC ACT GAC | 57 |
| GLP-2(1-33)A2G-NH$_2$ | CAT GGT GAT GGT TCT TTC TCT GAT GAG ATG AAC ACC ATT CTT GAT AAT CTT GCC GCC CGT GAC TTT ATC AAC TGG TTG ATT CAG ACC AAA ATC ACT GAC | 57 |
| GLP-2(1-34)A2G | CAT GGT GAT GGT TCT TTC TCT GAT GAG ATG AAC ACC ATT CTT GAT AAT CTT GCC GCC CGT GAC TTT ATC AAC TGG TTG ATT CAG ACC AAA ATC ACT GAC CGT | 58 |
| GLP-2(1-34)A2G-NH$_2$ | CAT GGT GAT GGT TCT TTC TCT GAT GAG ATG AAC ACC ATT CTT GAT AAT CTT GCC GCC CGT GAC TTT ATC AAC TGG TTG ATT CAG ACC AAA ATC ACT GAC CGT | 58 |
| GRF(1-44) | TAC GCT GAC GCT ATC TTC ACC AAC TCT TAC CGT AAA GTT CTG GGT CAG CTG TCT GCT CGT AAA CTG CTG CAG GAC ATC ATG TCC CGT CAG CAG GGT GAA TCT AAC CAG GAA CGT GGT GCT CGT GCT CGT CTG | 59 |
| PTH(1-34) | TCT GTT TCT GAA ATC CAG CTG ATG CAC AAC CTG GGT AAA CAC CTG AAC TCT ATG GAA CGT GTT GAA TGG CTG CGT AAA AAA CTG CAG GAC GTT CAC AAC TTC | 60 |
| PTH(1-37) | TCT GTT TCT GAA ATC CAG CTG ATG CAC AAC CTG GGT AAA CAC CTG AAC TCT ATG GAA CGT GTT GAA TGG CTG CGT AAA AAA CTG CAG GAC GTT CAC AAC TTC GTT GCT CTG | 61 |
| PTH(1-84) | TCT GTT TCT GAA ATC CAG CTG ATG CAC AAC CTG GGT AAA CAC CTG AAC TCT ATG GAA CGT GTT GAA TGG CTG CGT AAA AAA CTG CAG GAC GTT CAC AAC TTC GTT GCT CTG GGT GCT CCG CTG GCT CCG CGT GAC GCT GGT TCC CAG CGT CCG CGT AAA AAA GAA GAC AAC GTT CTG GTT GAA TCC CAC GAA AAA TCC CTG GGT GAA GCT GAC AAA GCT GAC GTT AAC GTT CTG ACC AAA GCT AAA TCC CAG | 62 |
| Amyloid P Component (27-38)-NH$_2$ | GAA AAA CCG CTG CAG AAC TTC ACC CTG TGC TTC CGT | 63 |
| (TyrO)-Fibrinopeptide A | TAC GCT GAT TCC GGT GAA GGT GAT TTC CTG GCT GAA GGT GGT GGT GTC CGT | 64 |
| Urechistachykinin II-NH$_2$ | GCT GCT GGT ATG GGT TTC TTC GGT GCG CGT | 65 |
| Amloid β-Protein (12-28) | GTC CAT CAT CAG AAA CTG GTC TTC TTC GCT GAA GAT GTC GGT TCC AAC AAA | 66 |

| Name | Sequence | SEQ ID NO: |
|---|---|---|
| Amyloid β-Protein (22-35) | GAA GAT GTC GGT TCC AAC AAA GGT GCT ATT ATT GGT CTG ATG | 67 |
| β-Endorphin (camel) | TAC GGT GGT TTC ATG ACC TCC GAA AAA TCC CAG ACC CCG CTG GTC ACC CTG TTC AAA AAC GCT ATT ATT AAA AAC GCT CAT AAA AAA GGT CAG | 68 |
| Valosin (porcine) | GTC CAG TAC CCG GTC GAA CAT CCG GAT AAA TTC CTG AAA TTC GGT ATG ACC CCG TCC AAA GGT GTC CTG TTC TAC | 69 |
| Vasoactive Intestinal Contractor Peptide mouse | TGC TCC TGC AAC TCC TGG CTG GAT AAA GAA TGC GTC TAC TTC TGC CAT CTG GAT ATT ATT TGG | 70 |

TABLE V

Amino acid sequences of cleavable peptide linker (CPL) examples

| Name | Amino Acid Sequences | SEQ ID NO: |
|---|---|---|
| CPL1 | Ala-Phe-Leu-Gly-Pro-Gly-Asp-Arg | 71 |
| CPL2 | Val-Asp-Asp-Arg | 72 |
| CPL3 | Gly-Ser-Asp-Arg | 73 |
| CPL4 | Ile-Thr-Asp-Arg | 74 |
| CPL5 | Pro-Gly-Asp-Arg | 75 |

TABLE VI

Nucleic acid sequences of cleavable neptide linker (CPL) examples

| Name | Nucleic Acid Sequences | SEQ ID NO: |
|---|---|---|
| CPL1 | GCTTTCCTGGGGCCGGGTGATCGT | 76 |
| CPL2 | GTCGACGATCGT | 77 |
| CPL3 | GGATCTGACCGT | 78 |
| CPL4 | ATCACTGACCGT | 79 |
| CPL5 | CCGGGTGACCGT | 80 |

TABLE VIII

Additional sequences

| Name | Sequence | SEQ ID NO: |
|---|---|---|
| FLAG | DYKDDDDK | 81 |
| T7 translation initiation sequence | TCTAGAAATAATTTTGTTTAACTT TAAGAAGGAGATATA | 82 |
| T7tag | MASMTGGQQMGR | 83 |
| T7tag | ATGGCTAGCATGACTGGTGGACAG CAAATGGGTCGCGGATCC | 84 |

EXAMPLES

Primers were ordered from companies specialized in DNA oligonucleotides synthesis (e.g., Operon Technologies, Alamedo, Calif.). General cloning procedures were followed as described in Molecular Cloning (Sambrook et al., $2^{nd}$ edition). Restriction enzymes were from New England Bio lab (Beverly, Mass.)

Example 1

Construction of a pBN95(Tac) Vector pBN95(Tac) is an optimized expression vector containing the backbone, origin of replication, and the tetracycline resistance gene from the pBR322 plasmid (New England Biolab, Beverly, Mass.); the lad gene (encoding a repressor protein) from pET16b (Novagen, Madison, Wis.); the tac promoter from pGEX2T (Amersham Pharmacia Biotech, Piscataway, N.J.); and the rrnB termination sequence from pKK223-3 (Amersham Pharmacia Biotech). The plasmid was constructed as described below.

The pBR322 vector backbone was prepared by cleaving the pBR322 plasmid (New England Biolabs, Beverly, Mass.) with PstI-SspI and isolating the large (approximately 3.5 kb) backbone fragment from an agarose gel. The lad gene was excised from the pET16b vector (Novagen) by cleavage with PstI, SapI and PshAI. The larger of the three released fragments (2.8 kb, compared to 1.2 kb and 1.7 kb) was isolated from an agarose gel. The lacI containing fragment was mixed with the 3.5 kb pBR322 backbone fragment and ligated using T4DNA ligase (Life Technologies, division of Invitrogen, Carlsbad, Calif.). The ligation mixture was transformed into high efficiency E. coli competent cells by heat shock at 42° C. for 45 seconds. Transformed cells were selected in LB+15 μl/ml tetracycline (LBT)+agar plates. Shaking cultures in 5 ml LBT media were started from single colonies and plasmids were prepared from these cultures. A correct plasmid construct was identified by restriction enzyme mapping. The resulting plasmid was designated pBN93.

The pBN95 plasmid then was constructed by digesting the pBN93 plasmid with XhoI and DraI and ligating the purified larger fragment to a EcoKV-XhoI fragment from a pCR-Script-rrnB plasmid, which contained the rrnB termination sequence as in pKK223-3 (Amersham Pharmacia Biotech). This terminator provides a highly effective termination signal that was used to replace the T7 terminator in the pBN93 plasmid. A map showing how the three fragments from pET16b, pBR322 and rrnB were ligated to form the pBN95 (T7) plasmid is provided in FIG. 1.

The T7 promoter was subsequently replaced with a modified tac promoter. A redesigned tac promoter was amplified by PCR using the pGEX2T plasmid (Amersham Pharmacia Biotech) which contained the tac promoter sequence. The following primers were used:

```
Primer 1:
                                        (SEQ ID NO: 85)
5' TGC ATT TCT AGA ATT GTG AAT TGT TAT CCG CTC

A 3'

Primer 2:
                                        (SEQ ID NO: 86)
5' TCA AAG ATC TTA TCG ACT GCA CGG 3'
```

PCR amplification produced the following product

```
                                        (SEQ ID NO: 87)
TCAAAGATCTTATCGACTGCACGGTGCACCAATGCTTCTGGCGTCAGGCA

GCCATCGGAAGCTGTGGTATGGCTGTGCAGGTCGTAAATCACTGCATAAT

TCGTGTGTCGCTCAAGGCGCACTCCCGTTCTGGATAATGTTTTTTGCGCC

GACATCATAACGGTTCTGGCAAATATTCTGAAATGAGCTG.TTGACA.

ATTAATCATCGGCTCG.TATAAT.GTGT[GGAATTGTGAGCGGATAACAATT

C]ACAATTCTAGAAATGCA
```

Figure 2:
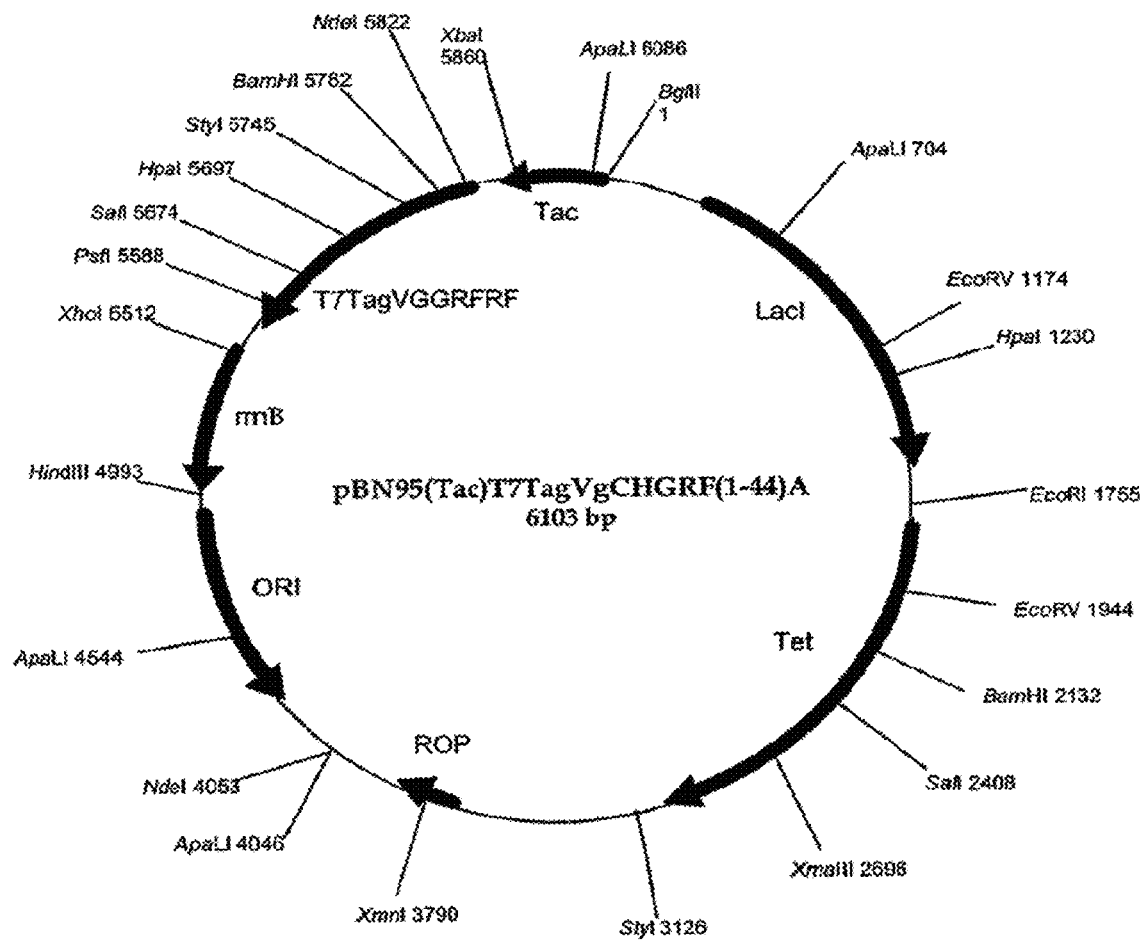
FIG. 2 is a plasmid map for the pBN95(Tac)-T7tagVgCH-GRF(1-44)A plasmid.

The upstream BglII restriction endonuclease recognition sequence (A/GATCT) and the downstream XbaI (T/CTAGA) recognition sequence are underlined with a single line. The −35 and −10 promoter consensus sequences are bolded and underlined with dots. The downstream transcriptional start A residue (within the lac operator gene sequence) is bolded and underlined with a solid line. The lac operator sequence is enclosed within brackets. The BglII-XbaI fragment of above product was inserted into the pBN95(T7) plasmid in replacement of the T7 promoter. The restriction map and components of a pBN95(Tac) plasmid containing T7tagVg-linker-GRF(1-44)A expression cassette are shown in FIG. 2.

Example 2

Construction of the pET23a-T7tagVg-GRF(1-44)A Plasmid, the pBN95(Tac)-T7tagVgCH-GRF(1-44)A Plasmid, and the pBN95-T7tagVgCH-GRF-(1-44)A Plasmid Polypeptide production by different *E. coli* strains (e.g., K strain or B strain) was developed through use of expression vectors containing different promoters (e.g., tac or T7) and different antibiotic selections (e.g., tetracycline or ampicillin). The expression vector pET23a (Novagen) has the T7 promoter and the ampicillin resistance gene. The expression vector pBN95(Tac) has the tac promoter and the tetracycline resistance gene. Expression vectors were constructed to contain the gene sequences for the following: (a) 12 amino acids of the T7tag (MASMTGGQQMGR) (SEQ ID NO: 83); (b) 29 amino acids of the vestigial (Vg) peptide (GSGQGQAQYL AASLVVFTNY SGDTA SQVD) (SEQ ID NO: 2) (Williams et al., *Genes & Development* 5:2481, 1991); (c) an amino acid linker (VNGPR AMVDD DDKCH) (SEQ ID NO: 146); and (d) the target peptide of GRF(1-44)A. The sequence of an expression cassette for T7tagVgCH-GRF(1-44)A is shown in FIG. 3.

(1) Construction of the pET23a-T7tag-GRF(1-44)A Plasmid.

The pET23a-T7tag-GRF(1-44)A plasmid was constructed by digesting pET23a plasmid (Novagen) with EcoRI-HincII and inserting the linker and GRF(1-44)A gene sequence as an EcoRI-EcoRV cleaved gene fragment. The gene sequence was constructed by cloning annealing overlapping synthetic oligonucleotides by standard methodology. The pET23a plasmid (Novagen) was digested with EcoRI-HincRII, and a 3.7 kb band from the agarose gel was excised and purified. The EcoRI-EcoRV GRF(1-44)A gene sequence was resolved on a 7.5% PAGE gel, and the GRF-containing fragment was purified. The two fragments were mixed and ligated. The ligation mixture was transformed to high efficiency *E. coli* competent cells by heat shock at 42° C. for 45 seconds. Transformed cells were selected in LB+50 µg/ml ampicillin (LBA)+agar plates. Plasmids from single transformants were prepared. A recombinant construct that contained the correct pET23a-T7tag-GRF(1-44)A plasmid was identified and confirmed by restriction enzyme mapping. This construct contains the linker sequence, from which GRF is released by enterokinase digestion. The sequence of this construct is shown in FIG. 4.

(2) Construction of the 29 Amino Acid Vestigial (Vg) Gene Fragment.

Two primers, which would anneal to each other, were designed as PCR primers to facilitate synthesis of the 29 amino acid fragment of the vestigial (Vg) gene.

```
SH17V:
                                        (SEQ ID NO:147)
CCG CGG ATC CGG CCA GGG ACA GGC TCA ATA TCT ATC

GGC CTC CTT GGT TGT GTT CAC CA-3'

↑
G

SH18V:
                                        (SEQ ID NO:148)
CGC GTT AAC GTC CAA CCT GGC TGG CCG TGT CGC -CCGA

GTA GTT GGT GAA CAC AAC CAA GG-3'
```

The oligo primers are self-annealing, so no additional template was required. The BamHI-HpaI sites in SH17V and SH18V, respectively, are underlined. The PCR reaction product was purified and cloned into the pCRBlunt vector (Invitrogen Corp., Carlsbad, Calif.) using Invitrogen's Zero Blunt PCR Cloning Kit to produce the pCRBlunt-Vg plasmid. The Vg fragment in pCRBunt-Vg was digested with BamHI-HpaI and purified on a 7.5% polyacrylamide gel. The fragment was eluted and ligated with a BamHI-HpaI digested pBT23a-T7tag-GRF(1-44)A plasmid (see FIG. 4 for sites). A recombinant clone pET23a-T7TagVg-GRF(1-44)A was isolated and shown by restriction mapping and sequencing to contain the correct plasmid construct (FIG. 5). The insert contained a single base substitution as indicated on primer 17.

(3) Construction of the pET23a-T7tagVgCH-GRF(1-44)A Plasmid.

The CH-GRF(1-44)A gene fragment was PCR-amplified using the plasmid pET23a-T7tagVg-GRF(1-44)A as a template and the following two primers:

```
SH23CH:
                                              (SEQ ID NO: 88)
CCG CTC GAG TTA TGC CAG ACG AGC ACG AGC-3'

SH-24:
                                              (SEQ ID NO: 89)
GCT ATG GTC GAC GAC GAC GAC AAA TGC CAC TAC GCT

ATC TTC ACC AAC-3'
```

The XhoI site in primer SH23CH is underlined and is placed immediately after the stop codon (bold). The SalI site in primer SH-24 is underlined. Primer SH-24 also contained a coding sequence of Cys-His to provide a palladium (Pd) cleavage site (bold). The resulting product was digested with SalI-XhoI and ligated to the SalI-XhoI digested pET23a-T7tagVg-GRF(1-44)A plasmid. A recombinant construct containing the correct pET23a-T7tagVgCH-GRF(1-44)A plasmid was identified (see FIG. 3 for expression cassette sequence).

(4) Construction of the pBN95(Tac)-T7tagVgCH-GRF(1-44)A Plasmid.

The expression cassette of the pET23a-T7tagVgCH-GRF(1-44)A plasmid was excised with XbaI-XhoI and isolated as a 0.4 kb fragment. The fragment was ligated into the XbaI-XhoI site of the pBN95(Tac) plasmid. A recombinant construct, designated pBN95(Tac)-T7tagVgCH-GRF(1-44)A, was isolated and confirmed to contain the correct insert (see FIG. 3 for expression cassette sequence).

Example 3

E. coli Shaking Culture Expression of Polypeptides Containing GRF(1-44)A

To express polypeptides, *E. coli* BL21 was die host cell when using tac promoter while BL21(DE3) was the host cell when using T7 promoter (Both cells are from Novagen, Madison, Wis.). Plasmids of the pET23a-T7tag-GRF(1-44)A pET23a-T7tagVg-GRF(1-44)A, pET23a-T7tagVgCH-GRF(1-44)A and pBN95(Tac)-T7tagVgCH-GRF(1-44)A were transformed into CaCl$_2$-treated competent cells by heat shock at 42° C. for 45 seconds. Transformed cells were selected on LB+50 µg/mL ampicillin (LBA)+agar plates for pET23a constructs, or on LB+15 µg/mL tetracycline (LBT) media+agar plates for pBN95(tac) constructs. Shaking flask cultures of 5 ml LBA or LBT media were started from single colonies of the transformed cells. Late log phase or overnight cell cultures were preserved in 10-15% glycerol at −80° C. or below (glycerol stocks). Shaking flask cultures in 5 ml to 500 ml LBA or LBT media (inoculated by 100 ul to 10 ml overnight culture) were grown at 37° C./220 rpm to an A$_{600}$ of 0.5-1.0, and polypeptide expression was induced by addition of IPTG (1 mM final concentration). Cultures were induced for lengths of time ranging from 3 hrs to overnight. Samples were taken from pre- and post-induced cells. Cells were pelleted and then lysed in TE (10 mM Tris, 1 mM EDTA, pH 8) buffer by sonication. The sample was centrifuged to separate insoluble and soluble proteins. The supernatant (soluble protein) was mixed 1:1 with 2×SDS-PAGE sample buffer. The pellets were resuspended directly in 1×SDS-PAGE sample. These samples were resolved on SDS-PAGE (Biorad or Novex) according to manufacturer's instructions and stained with Coomassie Brilliant Blue.

No expression was observed from the pET23a-T7tag-GRF(1-44)A/BL21(DE3) construct. High-level expression of insoluble precursor peptide of the predicted molecular weight (11 kDalton) was observed with the pET23a-T7tagVg-GRF(1-44)A plasmid in BL21(DE3). The results demonstrated that the Vg sequence promoted high-level expression of polypeptide inclusion bodies. However, the construct without the Vg sequence showed no detectable polypeptide expression.

Both the pET23a-T7tagVgCH-GRF(1-44)A/BL21(DE3) and pBN95(Tac)-T7tagVgCH-GRF(1-44)A/BL21 constructs produced high levels of polypeptide having the predicted size. This demonstrated that high level expressions of polypeptides containing Vg could be achieved using either the tac or the T7 promoter. Expression from both the pET23a-T7tagVg-GRF(1-44)A and the pET23a-T7tagVgCH-GRF(1-44)A constructs further demonstrated that the alteration of the linker region did not affect the ability of the Vg sequence to promote high level expression of polypeptide inclusion bodies.

Example 4

Codon Optimization of Vg in E. coli

The genetic codons used by *Drosophila melanogaster* for its Vg gene are not optimized for *E. coli*. For example, codons such as GGA that codes for Glycine, CTA that codes for Leucine, and TTG that codes for leucine are rarely used by *E. coli*. These codons were changed to GGT for residue 17, CTA to CTG for residue 22 and TTG to CTG for residue 26 (underlined in FIG. 6) by PCR using the following primers:

```
PL33VG:
                                              (SEQ ID NO: 90)
5'-CGC GGA TCC GGC CAG GGT CAG GCT CAA TAT CTG GCG

GCC TCC CTG GTT GTG TTC-3'

PL34GRF:
                                              (SEQ ID NO: 91)
5'-GAG CTC GAG TTA TGC CAG ACG AGC ACG AGC AAC

ACG-3'
```

The resulting PCR product was digested with BamHI-XhoI and cloned into the pET23a plasmid (Novagen, Madison, Wis.) at the BamHI-XhoI site to produce the plasmid pET23a-T7tagVg(opt)CH-GRF(1-44)A The XbaI-XhoI fragment from pET23a-T7tagVg(opt)CH-GRF(1-44)A was cloned into the pBN95(Tac) vector at the XbaI-XhoI site to produce the pBN95(Tac)-T7tagVg(opt)-CHGRF(1-44)A plasmid. This plasmid was transformed into *E. coli* BL21 cells. The transformed cells were selected in LBT media and a correct construct was identified and confirmed by restriction enzyme mapping and DNA sequencing. Polypeptide expression of this construct in a shaking flask culture was evaluated as described in Example 3. A high level expression of inclusion bodies of the polypeptide T7tagVgCH-GRF(1-44)A was observed by SDS-PAGE analysis.

Example 5

E. coli Fermentation Production of Polypeptides

Fermentation of an *E. coli* BL21 containing the pBN95(Tac)-T7tagVg(opt)-CHGRF(1-44)A plasmid was evaluated by 5 L or larger fermentation. A 100 µl glycerol stock of the bacterial containing the plasmid was used to inoculate 100 ml LBT media in a shaking flask. The shaking culture was grown in a rotary shaker at 37° C. until the A540 reached 1.5±0.5. The contents of the shaking flask culture were then used to inoculate a 5 L fermentation tank containing a defined minimal media (e.g., M9 media. Molecular Cloning, $2^{nd}$ edition, Sambrook et al.). Glucose served as the carbon source and was maintained at below 4%. About 15 µg/ml tetracycline was used in the fermentation. Dissolved oxygen was controlled at 40% by cascading agitation and aeration with additional oxygen. Ammonium hydroxide solution was fed to maintain the pH at about 6.9 and to serve as an additional nitrogen source. The cells were induced with a final concentration of 0.1-1 mM IPTG after the $A_{540}$ reached 50-75 for 4-10 hours. After the induction was complete, the cells were cooled and harvested by centrifugation. The cell sediments were either stored at a temperature below −20° C. until used or were lysed immediately. Cells, after thawing if they were frozen, were resuspended in 50 mM Tris, 2.5 mM EDTA, pH7.5 and lysed by sonication or homogenization. The lysate was centrifuged to pellet inclusion bodies of the expressed polypeptide. The polypeptide sediments were dissolved in 8M urea or in 95% formic acid for analysis or further treatment. More than 5 g of the desired polypeptide was obtained from 1 L of fermentation broth.

Example 6

Modification of the Vg Hydrophobic Core

Figure 7:
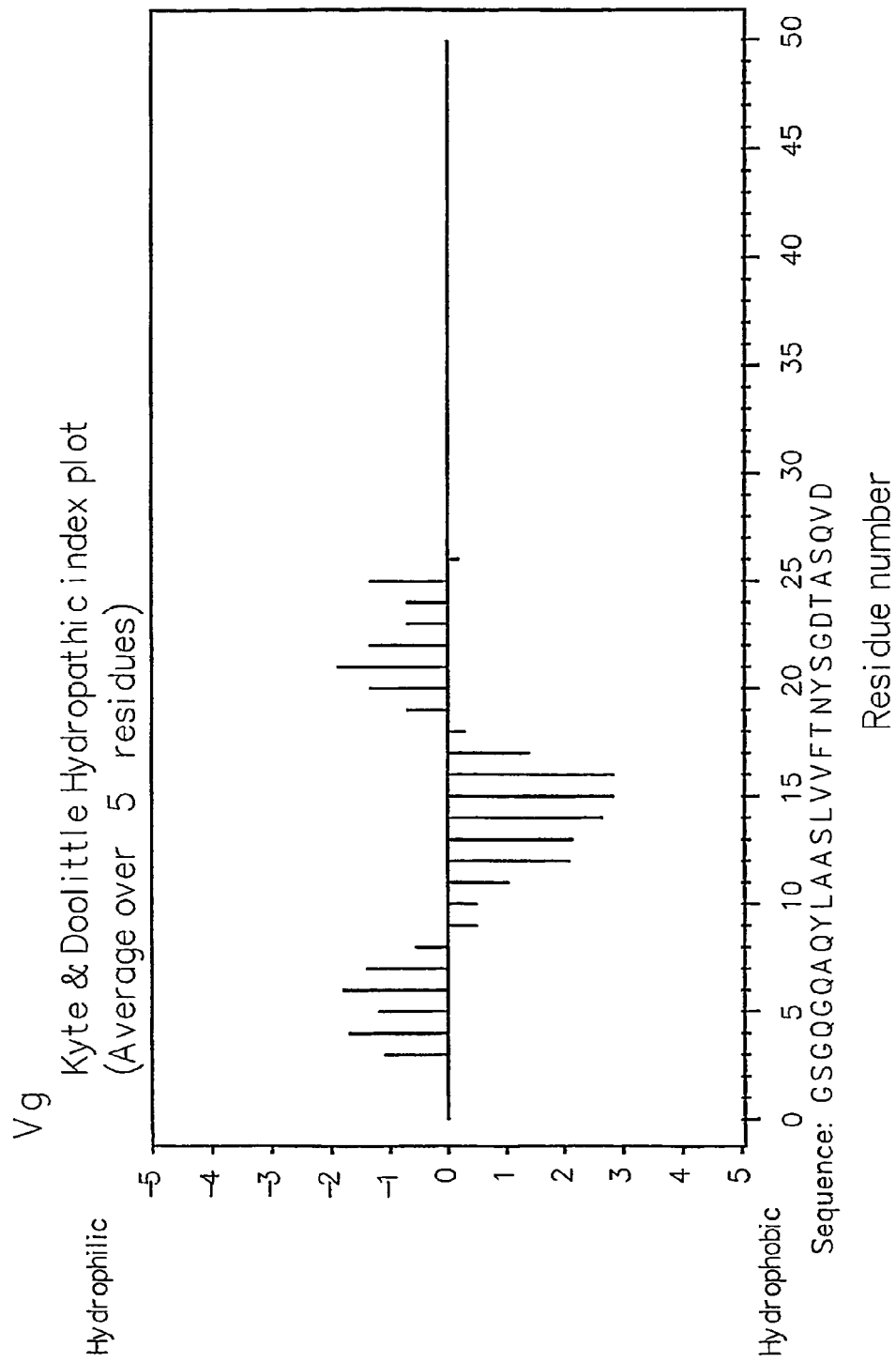
FIG. 7 illustrates a hydrophobicity plot for an inclusion body fusion partner having SEQ ID NO:2.

A hydrophobic core sequence (LAASLVVF) (SEQ ED NO:92) was identified by Hydrophobicity plot (e.g., Kyte & Doolittle, Hopp & Woods in the DNAsis program) (see FIG. 7) (Kyte et al., *J. Mol. Biol.*, 157:105 (1982)). This region was substituted with other amino acids to alter the solubility, expression yield, effects on linker cleavage and other characteristics of the polypeptide. The substitution was achieved by PCR using degenerate primers. VgMut1 was designed to change the amino acid sequence LAASLVV to DEASDVE in the Vg hydrophobic core region. The DNA coding the mutated Vg was amplified by PCR using the pET23a-T7tagVgCH-GRF(1-44)A plasmid as the template and the following primers.

VgXY1:
(SEQ ID NO: 93)
5'-CGC GGA TCC GGC CAG GGT CAG GCT CAA TAT <u>GAC GAA</u>
<u>GCT</u> TCC <u>GAC</u> GTT <u>GAA</u> TTC ACC AAC TAC TCG-3'

XBAXY2:
(SEQ ID NO: 94)
5'-TCA GTC ACG ATG AAT TCC C-3'.

The underlined bases in the VGXY1 primer represent the codons of changed residues. The PCR product was digested with BamHI-XhoI and then cloned into pET23a vector at the BamHI-XhoI site, producing the pET23a-T7tagVgMut1CH-GRF(1-44)A plasmid (see FIG. 8 for sequence of the polypeptide containing VgMut1). After it was confirmed by restriction enzyme mapping and DNA sequencing, the plasmid was transformed into BL21(DE3) cells and evaluated for polypeptide expression as described in Example 3.

SDS-PAGE analysis showed no significant amount of polypeptide corresponding to T7tagVgMut1CH-GRF(1-44)A was observed, indicating that the dramatic change of the LAASLVVF (SEQ ID NO: 92) hydrophobic core to a hydrophilic region abolished the Vg function to enhance inclusion body formation and the overall production of the polypeptide in *E. coli*.

Another mutation (designated as VgMut4) in the Vg hydrophobic core region was prepared by annealing two degenerate primers that are complementary to each other. The primer sequences are as follows:

PL35Vg:
(SEQ ID NO: 95)
5'-GAT CCG GCC AGG GTC AGG CTC AAT ATC TGN CGG CCT
CCC TGG <u>TTM</u>-3'

PL36VgR:
(SEQ ID NO: 96)
5'-AAT <u>TKA</u> ACC AGG GAG GCA GNC AGA TAT TGA GCC TGA
CCC TGG CCG-3'

The underlined bases in these two primers, represent the changed residues (see FIG. 9 for the sequence of the polypeptide containing VgMut4). The two primers were mixed at equal molar concentration, denatured, at 94° C. for one minute, annealed at 50° C. for 10 minutes, and then cloned into pET23a-T7tagVgMut1CH-GRF(1-44)A at the BamHI-EcoRI site to produce a library of pET23a-T7tagVgMut4CH-GRF(1-44)A plasmids. The resulting plasmids were transformed into BL21(DE3) cells and evaluated for polypeptide expression as in Example 3.

Several clones showed high level expression of polypeptide inclusion bodies by SDS-PAGE analysis. Plasmids from these clones were sequenced and the mutation in the Vg hydrophobic core region was determined. The inclusion bodies were isolated by lysis and centrifugation of cells from 5 ml to 500 ml LBA cultures that were induced with IPTG. The inclusion bodies were men evaluated for solubility in 4 M urea and 50 mM HCl. The same quantity of inclusion bodies from different polypeptides of T7VgMut4CH-GRF(1-44)A were suspended in a small amount of 4 M urea or 50 mM HCl so that the solution was saturated with the polypeptides. The concentration of the solubilized polypeptide was determined by measurement of UV absorbance at 280 nm and SDS-PAGE analysis. If a polypeptide could reach a higher concentration in 4 M urea or 50 mM HCl than the other polypeptides, it was identified as exhibiting higher solubility. A clone containing a single amino acid substitution (see Table VET) demonstrated high levels of expression, with altered solubility properties in the urea solvent.

TABLE VIII

The Solubility of Polypeptides with Modified Vg

| Hydrophobic core of Vg (changes from original sequence bolded) | Inclusion body yield (by SDS-PAGE) | Inclusion body solubility in 4M urea | Inclusion body solubility in 50 mM HCl |
|---|---|---|---|
| LAASLVVF (SEQ ID NO: 92) | Very High | Good | Good |

TABLE VIII-continued

The Solubility of Polypeptides with Modified Vg

| Hydrophobic core of Vg (changes from original sequence bolded) | Inclusion body yield (by SDS-PAGE) | Inclusion body solubility in 4M urea | Inclusion body solubility in 50 mM HCl |
|---|---|---|---|
| LAASLVQF (SEQ ID NO: 97) | Very High | Better | Better |
| LSASLVQF (SEQ ID NO: 98) | High | NA | NA |
| LTASLVKF (SEQ ID NO: 99) | High | NA | NA |

Example 7

Expression of T7tagVg-PTH(1-34) Polypeptides

The PTH sequence was amplified using the following primers:

PTH19981:
(SEQ ID NO: 100)
5' ACC GCT CGA GGA TAT CTT AGA AGT TGT GAA CGT

CCT GCA G-3'

PTH19982:
(SEQ ID NO: 101)
5' CAG CGT TAA CCC GGA ATT CTC TGT TGG TGG TGG

TGG TGG TCC GCG TTC T-3'

The XhoI and HpaI sites are underlined in the PTH19981 and PTH19982 primers, respectively. The amplified fragment was cleaved with XhoI-HpaI and cloned into the XhoI-HpaI site in the pET23a-T7tagVg-GRF(1-44)A plasmid. The polypeptide sequence of the resulting pET23a-T7tagVg-PTH(1-34) plasmid is shown in FIGS. 10 and 12. The 'Gly-Pro-Arg' sequence prior to PTH is a thrombin cleavage site that provides for release of the PTH peptide.

A Cys-His dipeptide for Pd cleavage was inserted between the thrombin linker and PTH(1-34) by PCR using the pET23a-T7tagVg-PTH(1-34) as template and using the PTH19981 primer from above and PTH 19983 primer, identified below.

PTH19983:
(SEQ ID NO: 102)
5' CCG GAA TTC TCT GTT GGT GGT GGT GGT CCG CGT

TGC CAC TCT GTT TCT GAA ATC 3'

An EcoRI site in this primer is underlined. The PCR product was cleaved with EcoRI-XhoI, and cloned into an EcoRI-XhoI cleaved pET23a-T7tagVg-PTH(1-34) plasmid. The sequence of the resulting clone was named as pET23a-T7tagVgCH-PTH(1-34).

The above two plasmids were transformed into BL21(DE3) cells and evaluated for polypeptide expression as describe in Example 3. Both constructs expressed high levels of IPTG inducible, insoluble inclusion bodies of the desired polypeptide, which had different linkers and target peptides from Examples 1 to 3.

Example 8

Deletions in the Vg

Portions of the Vg leader were deleted to minimize the length of the leader. A PCR reaction was performed using pET23a-T7tagVgCH-PTH(1-34) as template, the PTH19981 primer described in Example 7, and the following primer:

GRFXY629:
(SEQ ID NO: 103)
5' CTC GGA TCC CAA TAT CTG GCT GCC GTG CTG GTT GTG

TTC ACC AAC TAC TCG-3'.

The GRFXY629 primer deletes the amino acid sequence GQGQA (SEQ ID NO: 104) that immediately follows the BamHI site (underlined), and introduces a serine (TCC) to Valine (GTG, bold) substitution in the Vg hydrophobic sequence (LAASLVVF (SEQ ID NO: 92) to LAAVLVVF (SEQ ID NO: 105)). This substitution increased the hydrophobicity of the Vg peptide (Kyte & Doolittle plot). The deletion also decreased the percentage of the inclusion body fusion partner in the tandem polypeptide and thereby increased the percentage of the preselected polypeptide in the tandem polypeptide. The PCR product was cleaved with BamHI-HpaI and cloned into HpaI-BamHI cleaved pET23a-T7tagVgCH-GRF(1-44)A. The resultant clone, pET23a-T7tagVg(Del1)CH-GRF(1-44)A expressed high levels of IPTG-inducible inclusion bodies.

The PTH(1-34) gene was substituted for GRF(1-44)A in the pET23a-T7tagVg(Del1)CH-GRF(1-44)A vector as follows.

The pET23a-T7tagVg(Del1)CH-GRF(1-44)A was cleaved with HpaI-XhoI to remove GRF(1-44)A, and the PTH(1-34) element from pET23a-T7tagVg-PTH(1-34) was obtained by HpaI/XhoI digestion. Ligation of these fragments produced the plasmid pET23a-T7tagVg(Del1)-PTH(1-34) (see FIG. 10). A high level of IPTG-inducible inclusion bodies of the T7tagVg(Del1)-PTH(1-34) polypeptide was produced by this construct in BL21(DE3).

A second deletion of the Vg peptide was made in which amino acids TASQVD (SEQ ID NO: 106) immediately N-terminal to the HpaI site in the Vg peptide were deleted (Del2; see FIGS. 10 & 12). The primers utilized for PCR were MGDEL3 and PL28 (PL28 anneals to the 5' region of the ribosome binding site), using the pET23a-T7tagVg-PTH(1-34) clone as template.

MGDEL3:
(SEQ ID NO: 107)
5' GAC GTT AAC GTC GCC CGA GTA GTT GGT GAA CAC-3'
(HpaI site is underlined)

PL28:
(SEQ ID NO: 108)
5' GAG CGG ATA ACA ATT CAC A-3'

The PCR product was cleaved with HpaI-XbaI and cloned into a HpaI-XbaI cleaved pET23a-T7tagVg-PTH(1-34) plasmid. The resultant plasmid, pET23a-T7tagVg(Del2)-PTH(1-34) expressed high levels of IPTG-inducible, insoluble inclusion bodies of a size corresponding to the T7tagVg(Del2)-PTH(1-34) precursor peptide. The experiment demonstrated that this region (TASQVD) (SEQ ID NO: 106), was dispensable for Vg to form inclusion bodies.

In another experiment, the linker region of the T7tagVgCH-PTH(1-34) precursor peptide was deleted. The PEFSV (SEQ ID NO:109) amino acid sequence immediately C-terminal to the HpaI site were deleted (Del 3; see FIG. 10). The Del 3 region was created by PCR amplification using the pET23a-T7tagVg-PTH(1-34) plasmid as a template, and using the primers depicted below. The PL39 primer anneals to the plasmid in the terminator region.

MGDEL2:
(SEQ ID NO: 110)
5' GAC GTT AAC GGT GGT GGT GGT GGT TGC CAC TCT GTT TCT GAA ATC-3'

PL39:
(SEQ ID NO: 111)
5'-TGC TAG TTA TTG CTC AGC GGT G-3'

The PCR product contained a Cys-His coding sequence at the N-terminus of PTH(1-34) as shown in FIG. 11. After the PCR product was confirmed by sequencing, it was digested by HpaI-XhoI and then cloned into the pET23a-T7tagVg-PTH(1-34) plasmid at HpaI-XhoI sites to produce the pET23a-T7tagVg(Del3)CH-PTH(1-34) plasmid. When the HpaI-XhoI digested PCR fragment was cloned into the pET23a-T7tagVg(Del2)CH-PTH(1-34) plasmid at HpaI-XhoI sites, it produced the pET23a-T7tagVg(Del2+3)CH-PTH(1-34) plasmid. The DNA sequences and predicted amino acid sequences of both constructs are shown in FIGS. 10 and 12.

Both of the above plasmids and the pET23a-T7tagVg-PTH(1-34) plasmid (without deletion) were transformed separately into the E. coli K strain, HMS-174<DE3). Expression was induced with IPTG. All three clones produced high levels of IPTG-inducible, insoluble inclusion bodies. The results showed that the Vg was not strain-specific, as it functions in both the BL21 and HMS-174 strains and that the Del1, Del2, Del3 or Del2+3 deletions do not affect Vg function. The Del2+3 deletion removed 11 amino acids, and the entire length of the T7tagVg(Del2+3)CH leader element was reduced to 44 amino acids. Thus, the entire. T7tagVg(Del2+3)CHPTH(1-34) construct was reduced to 78 amino acids in length.

Example 9

Expression of T7tagVg-CAT

To determine whether the disclosed invention enhances the production of large peptides or soluble proteins, a DNA construct encoding chloramphenicol acetyltransferase (CAT) was prepared, with and without fusion to Vg. Active CAT confers chloramphenicol resistance.

(1) pB115 Vector pBN115 was derived from pGEX-2T by replacing the FspI-SmaI fragment containing the tac promoter-GST structural gene fusion with a BglII-XbaI-NheI-XhoI cassette from the pBN95(Tac) plasmid. The tac promoter was replaced with the *chlorella* virus promoter (U.S. Pat. No. 6,316,224) at the BglII-XbaI site. Plasmid pBN115 contains lacI$^q$ and Amp$^r$. Use of the pBN115 vector has been described in U.S. Pat. No. 6,316,224 to Xia.

(2) CAT (Chloramphenicol Acetyltransferase)

The CAT gene (encoding 219 amino acids) was PCR-amplified from plasmid pKK232-8 (Amersham Pharmacia Biotech, Piscataway, N.J.). The following two oligos were used in the PCR reaction:

(SEQ ID NO: 112)
CATXY1: 5'-GGT GCT AGC ATG GAG AAA AAA ATC ACT-3'

(SEQ ID NO: 113)
CATXY2: 5'-ATC CTC GAG CTG CCA AGG GTT-3'

CATXY1 was used as the forward primer and contains the NheI site (GCTAGC) for cloning. CATXY2 was used as the reverse primer and contains the XhoI site (CTCGAG) for cloning. The resultant PCR product was inserted into pBN115 at the NheI-XhoI sites to create the pBN115-CAT plasmid (FIG. 13). The pBN115-CAT plasmid was transformed into E. coli and expressed as described in Example 3. CAT was over-expressed as a soluble, active enzyme protein under the control of the *chlorella* virus promoter at 37° C.

(3) T7tagVg-CAT

A NheI-releasable DNA fragment containing the T7tagVg fusion gene was prepared by PCR. The following primers were used as PCR primers:

VGNHE:
(SEQ ID NO: 114)
5'-ATC GCT AGC GTT AAC GTC CAC CTG GCT GGC-3'

XBAXY1:
(SEQ ID NO: 115)
5'-CCC GGG TCG ACA ACT TTA AGA AGG AGA TA-3'

VGNHE served as the reverse primer and contained the restriction sites HpaI (GTTAAC) and NheI (GCTAGC). XBAXY1 served as the forward primer and contained the DNA sequence upstream of the start codon. The pBN95(Tac)-T7tagVg(opt)-CHGRF(1-44)A plasmid containing the codon-optimized Vg served as the template for PCR.

The PCR generated NheI fragment containing the T7tagVg fusion (FIG. 14) was inserted into pBN115-CAT at the NheI site to produce the pBN115-T7tagVg-CAT plasmid. The plasmid was restriction enzyme mapped to confirm that the right orientation of the insert was obtained. The plasmid was transformed into E. coli and expressed as described in Example 3. T7TagVg-CAT was over-expressed as an insoluble protein at 37° C., although CAT was expressed as a soluble protein.

Example 10

Expression of T7tagVg-β-galactosidase

The gene encoding a β-galactosidase of 1021 amino acids was amplified from E. coli MG1655 LacZ gene using the following two primers:

BGXY1:
(SEQ ID NO: 116)
5'-ATG GCT AGC ATA GAT CCC GTC GTT TTA CAA CGT CGT

GAC-3'

BGXY2:
(SEQ ID NO: 117)
5'-CGG CTC GAG TTA TTA TTT TTG ACA CCA GAC CAA CTG

GTA-3'

Figure 15:
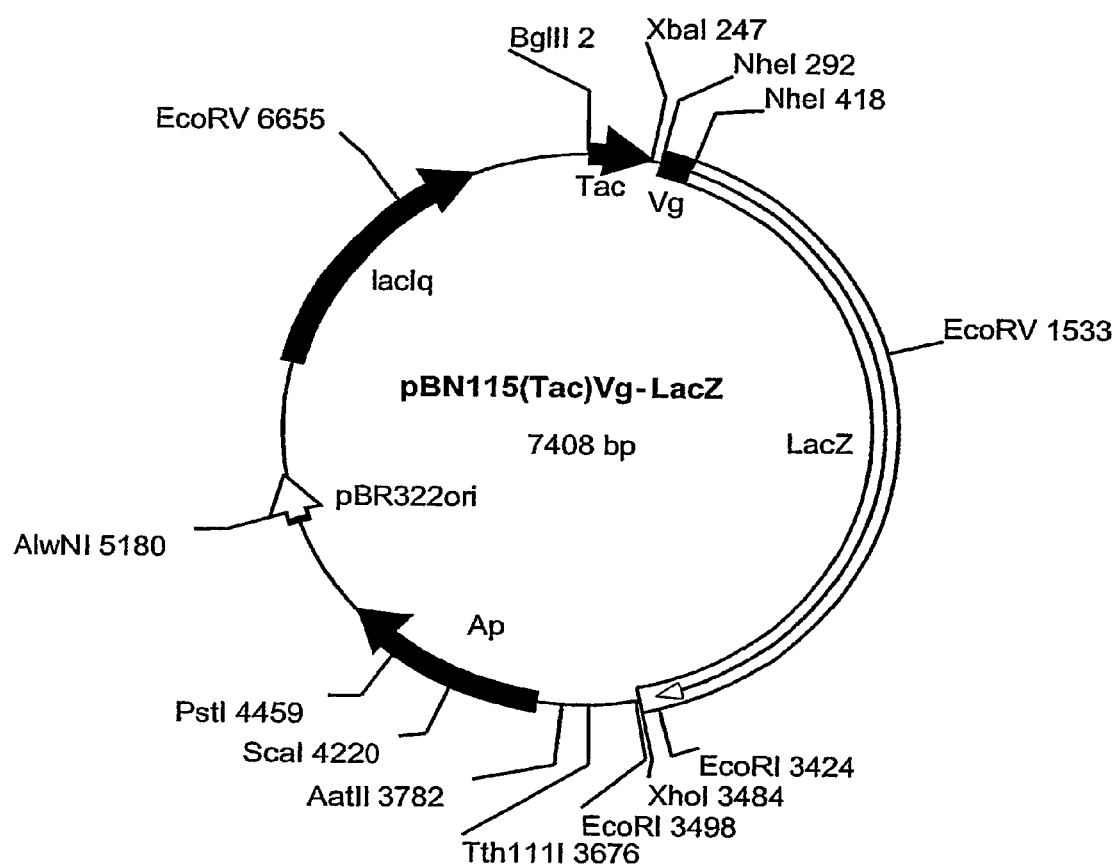
FIG. 15 is a plasmid map for the pBN115-T7tagVg-LacZ plasmid.

The forward primer BGXY1 introduced an NheI site (underlined) into the PCR product, while the reverse primer BGXY2 introduced an XhoI site (underlined). The PCR product was digested with NheI-XhoI and then cloned into the pBN115 plasmid at an NheI-XhoI sites to produce the pBN115-LacZ plasmid. The NheI-releasable T7tagVg fragment from Example 9 was inserted into the pBN115-LacZ plasmid at the NheI site to produce the pBN115-T7tagVg-LacZ plasmid (FIG. 15). The plasmid was restriction enzyme mapped to confirm that the right orientation of the insert was obtained. The plasmid was transformed into *E. coli* and expressed as described in Example 3.

Figure 16:
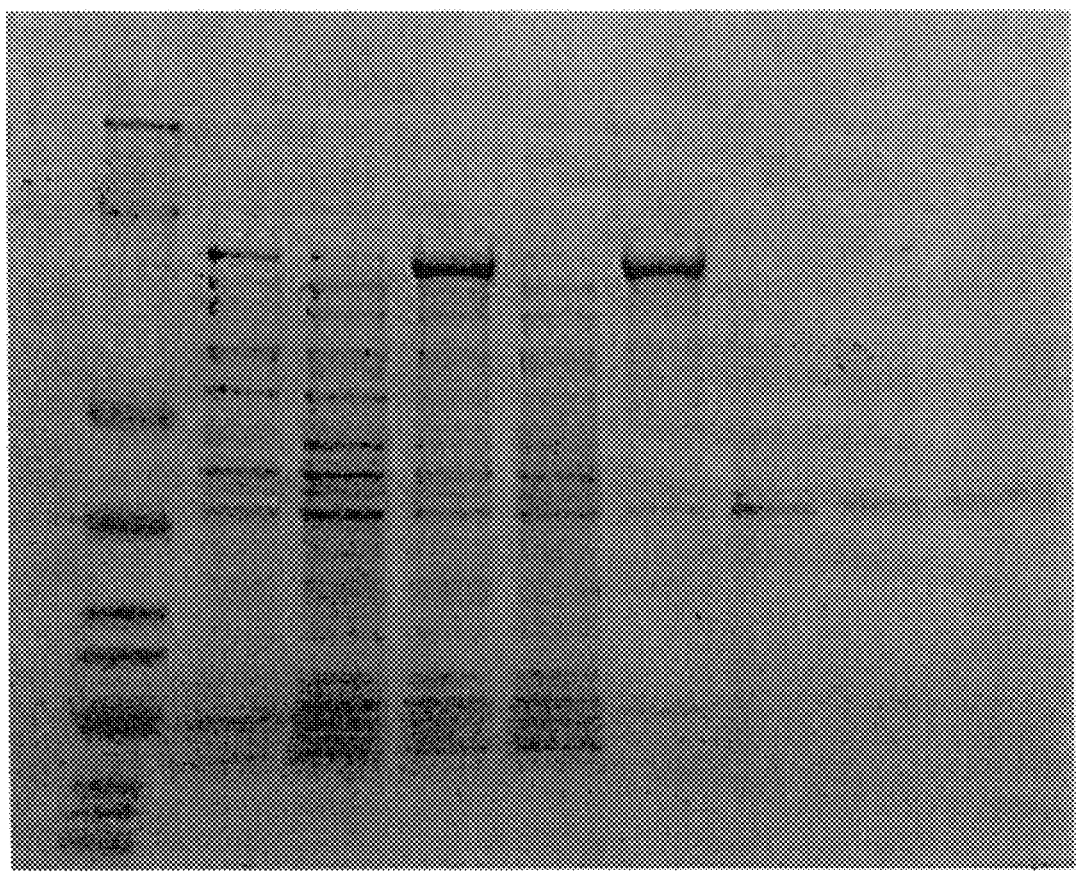
FIG. 16 illustrates an SDS-PAGE gel of samples obtained from cells that were treated according to the indicated conditions. Lane 1: Novex multimark molecular weight marker, Lane 2: 37° C., induced 2 hr, soluble fraction of pBN115 (Tac)-T7tagVg-LacZ; Lane 3: 37° C., uninduced, soluble fraction of pBN115(Tac)-T7tagVg-LacZ; Lane 4: 27° C., induced 2 hr, soluble fraction of pBN115(Tac)-T7tagVg-LacZ; Lane 5: 27° C., uninduced, soluble fraction of pBN115 (Tac)-T7tagVg-LacZ; Lane 6: 37° C., induced 2 hr, insoluble fraction of pBN115(Tac)-T7tagVg-LacZ; Lane 7: 37° C., uninduced, insoluble fraction of pBN115(Tac)-T7tagVg-LacZ; Lane 8: 27° C., induced 2 hr, insoluble fraction of pBN115(Tac)-T7tagVg-LacZ; Lane 9: 27° C., uninduced, insoluble fraction of pBN115(Tac)-T7tagVg-LacZ.

Shaking culture expression indicated that the tandem polypeptide of T7tagVg-LacZ was expressed mostly as inclusion bodies at 37° C. and was partially soluble at 27° C. (FIG. 16). Without the Vg leader, LacZ was expressed as soluble protein in *E. coli*. This surprising result showed that the Vg leader promoted the formation of inclusion bodies or polypeptide aggregates even when fused to large soluble proteins. The formation of inclusion bodies or polypeptide aggregates increased at higher expression temperature.

Example 11

Expression of T7tagVgCH-GLP(7-36)CH

The CH-GLP(7-36)CH fragment was produced by PCR using the following primers:

Primer CHGLP:
(SEQ ID NO: 118)
5' GCT ATG GTC GAC GAC GAC GAC AAA TGC CAC CAT GCT

GAA GGT ACC TTC ACC TCC 3'

Primer GLPCH:
(SEQ ID NO: 119)
5' ATG CAT CTC GAG TTA GTG GCA ACG ACC TTT AAC CAG

CCA AGC GAT GAA 3'

The SalI site in primer CHGLP and the XhoI site in primer GLPCH are underlined. The PCR product was cleaved with SalI-XhoI and ligated into a SalI-XhoI cleaved and alkaline phosphatase treated pBN95(Tac)-T7tagVg(opt)CH-GRF(1-44)A vector. The resultant plasmid pBN95(Tac)-T7tagVgCH-GLP(7-36)CH was transformed into *E. coli* HMS174 and BL21. All of these cell lines expressed a high level of polypeptide inclusion bodies corresponding to T7VgCH-GLP(7-36)CH after IPTG induction.

Example 12

Generalized Expression Cassettes

Figures 18, 19:
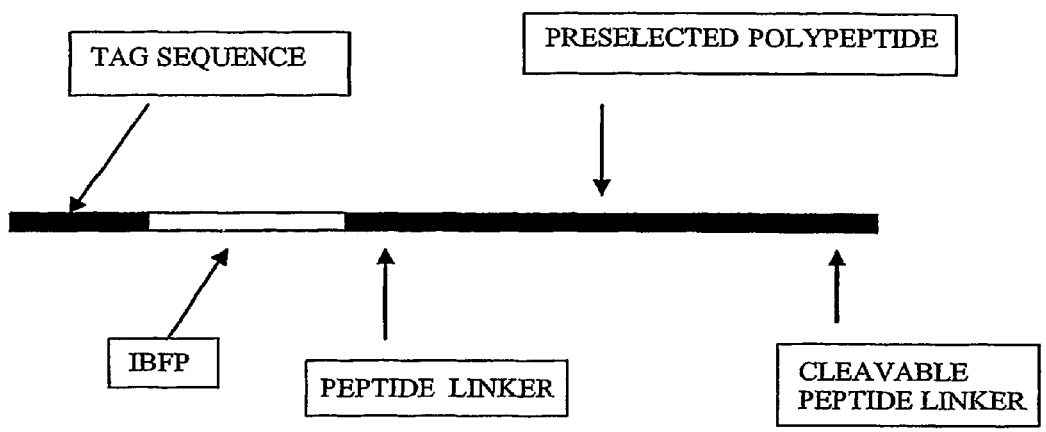
FIG. 18 illustrates a generalized structure of a polypeptide of the invention.
FIG. 19 illustrates a series of amino acid deletions occurring around the hydrophobic core of SEQ ID NO: 2.

Numerous preselected polypeptides can be produced through use of the methods, constructs, and inclusion body fusion partners described herein. Preferably a preselected polypeptide is operably linked to an inclusion body fusion partner having SEQ ID NO:2-4. These tandem polypeptides are exemplified by the generalized structure illustrated in FIG. 18. The methods described in examples 1 and 2 can be used to prepare a nucleic acid construct containing a nucleic acid sequence that encodes virtually any preselected polypeptide. This nucleic acid construct can be grown and used to produce the preselected polypeptide according to the methods described in examples 3, 5, 7 and 9-11. Thus, the methods and constructs may be used under a wide variety of concumstances to produce numerous different preselected polypeptides.

REFERENCES

Alberts et al. Molecular Biology of the Cell, 2nd ed, 1989
Amann et al., *Gene*, 25:167 (1983)
Aubin et al. *Methods Mol. Biol.*, 62:319 (1997)
Augustin et al., *FEMS Microbiol Lett.*, 66:203 (1990)
Ausubel et al., *Current Protocols in Molecular Biology*, Green Publishing Associates and Wiley Interscience, N.Y. (1989)
Barany et al., *J. Bacteriol.*, 144:698 (1980)
Beach and Nurse, *Nature*, 300:706 (1981)
Beaucage and Caruthers, *Terra. Letts.*, 22:1859 (1981)
Birnstiel et al., *Cell*, 41:349 (1985)
Boshart et al. *Cell*, 41:521 (1985)
Botstein, et al. *Gene*, 8:17 (1979)
Brake et al., *Proc. Natl. Acad. Sci. USA*, 81:4642 (1984)
Butt et al., *Microbiol. Rev.*, 51:351 (1987)
Carbonell et al. *Gene*, 21: 409 (1988)
Carbonell et al., *J. Virol.*, 56:153 (1985)
Chaney et al., *Somat. Cell Mol. Genet.*, 12:237 (1986)
Chang et al. *Nature*, 198:1056 (1977)
Chassy et al., *FEMS Microbiol. Lett.*, 44:173 (1987)
Cohen et al., *Proc. Natl. Acad. Sci. USA*, 69:2110 (1973)
Cohen et al., *Proc. Natl. Acad. Sci. USA*, 77:1078 (1980)
Coombs et al., *Chem. Biol.*, 5:475 (1998)
Cregg et al. *Mol. Cell. Biol.*, 5: 3376, 1985
Das et al., *J. Bacteriol.*, 158: 1165 (1984)
Davidow et al., *Curr. Genet.*, 10:39 (1985)
Davies et al., *Ann. Rev. Microbiol.*, 32:469 (1978)
Dayhoff et al. (1978) *Atlas of Protein Sequence and Structure* (Natl. Biomed. Res. Found., Washington, D.C.)
de Boer et al., *Proc. Natl. Acad. Sci. USA*, 80:21 (1983)
De Louvencourt et al., *J. Bacteriol.* 154:737 (1983)
De Louvencourt et al., *J. Bacteriol.*, 254:737 (1983)
Dijkema et al., *EMBO J.*, 4:761 (1985)
Dower et al., *Nuc. Acids Res.*, 16:6127 (1988)
Felgner et al., *J. Biol. Chem.*, 261:2550 (1994)
Felgner et al., *Proc. Natl. Acad. Sci.*, 84:7413 (1987)
Fiedler et al., *Anal. Biochem*, 170:38 (1988)
Franke et al., *J. Gen. Virol.*, 66:2761 (1985)
Fraser et al., *In Vitro Cell. Dev. Biol.*, 25:225 (1989)
Freifelder, Physical Biochemistry: Applications to Biochemistry and Molecular Biology, W.H. Freeman and Co., 2nd edition, New York, N.Y. (1982)
Friesen et al., "The Regulation of Baculovirus Gene Expression", in: The Molecular Biology of Baculoviruses (ed. Walter Doerfler), 1986
Gaillardin et al., *Curr. Genet.* 10:49 (1985)
Ghrayeb et al., *EMBO J.*, 3:2437 (1984)
Gleeson et al., *J. Gen. Microbiol.*, 132:3459 (1986)
Gluzman, *Cell*, 23:175 (1981)
Goeddel et al., *Nuc. Acids Res.*, 8:4057 (1980)
Gorman et al., *Proc. Natl. Acad. Sci. USA.*, 79:6777 (1982b)

Graham and van der Eb, *Virology,* 52:456 (1973)
Gregor and Proudfoot, *EMBO J.,* 12:4771 (1998)
Guan et al., *Gene,* 67:21 (1997)
Harlander, "Transformation of *Streptococcus lactis* by electroporation", in: *Streptococcal Genetics* (ed. J. Ferretti and R. Curtiss III), 1987
Harlow and Lane, Antibodies: A Laboratory Manual, Cold Spring Harbor Laboratory Press, Cold Spring Harbor, N.Y. (1988)
Henikoff et al., *Nature,* 283:835 (1981)
Hinnen et al., *Proc. Natl. Acad. Sci. USA,* 25:1929 (1978)
Hollenberg et al., "The Expression of Bacterial Antibiotic Resistance Genes in the Yeast *Saccharomyces cerevisiae*", in: Plasmids of Medical, Environmental and Commercial Importance (eds. K. N. Timmis and A. Punier), 1979
Hollenberg et al., *Curr. Topics Microbiol. Immunol.,* 96:119 (1981)
Ito et al. *J. Bacteriol.,* 153:163 (1983)
Kaufman et al., *Mol. Cell. Biol.,* 9:946 (1989)
Kawai and Nishizawa, Mol. Celt. Biol., 4:1172 (1984)
King and Possee, The baculovirus expression system. A laboratory guide. Chapman and Hall, London, England (1992)
Kohrer et al., *Proc. Natl. Acad. Sci. (USA),* 91:14310 (2001)
Kowal et al., *Proc. Natl. Acad. Sci. (USA),* 98:2268 (2001)
Kunkel et al. *Methods in Enzymol.,* 154:367 (1987)
Kunkel, *Proc. Natl. Acad. Sci. USA,* 82:488. (1985)
Kurtze et al., *J. Basic Microbiol,* 25:141 (1985)
Kurtz et al., *Mol. Cell. Biol.,* 6:142 (1986)
Kushner, "An improved method for transformation of *Escherichia coli* with ColE1-derived plasmids", in: Genetic Engineering: Proceedings of the International Symposium on Genetic Engineering (eds. H. W. Boyer and S., Nicosia), 1978
Kyte et al., *J. Mol. Biol.,* 157:105 (1982)
Lebacq-Verheyden et al., *Mol. Cell. Biol.,* 8:3129 (1988)
Lewin, Genes VII, Oxford University Press, New York, N.Y. (2000).
Lopez-Ferber et al. *Methods Mol. Biol.,* 32:25 (1995)
Luckow and Summers, *Virology,* 17:31 (1989)
Maeda et al., *Nature,* 315:592 (1985)
Mandel et al., *J. Mol. Biol.,* 53:159 (1970)
Maniatis et al. *Science,* 236:1237 (1987)
Martin et al. *DNA,* 7: 99 (1988)
Marumoto et al., *J. Gen. Virol.,* 68:2599 (1987)
Masson et al., *FEMS Microbiol. Lett.,* 60:273 (1989)
Masui et al., in: Experimental Manipulation of Gene Expression, (1983)
McCarroll and King, *Curr. Opin. Biotechnol.,* 8:590 (1997)
Mercerau-Puigalon et al. *Gene,* 11:163 (1980)
Miller et al., *Ann. Rev. Microbiol.,* 42:177 (1988)
Miller et al., *Bioessays,* 4:91 (1989)
Miller et al. *Proc. Natl. Acad. Sci. USA,* 8:856 (1988)
Miyajima et al. *Gene,* 58: 273 (1987)
Myanohara et al., *Proc. Natl. Acad. Sci. USA,* 80:1 (1983)
Neuman et al., *EMBO J.,* 1:841 (1982)
Oka et al., *Proc. Natl. Acad. Sci. USA,* 82:7212 (1985)
O'Reilly et al., Baculovirus expression vectors: a laboratory manual. W.H. Freeman & Company, New York, N.Y. (1992)
Orr-Weaver et al., *Methods in Enzymol.* 101:228 (1983)
Palva et al. *Proc. Natl. Acad. Sci. USA,* 79: 5582 (1982)
Panthier et al. *Curr. Genet.,* 2:109 (1980)
Pearson, *Genomics,* 11:635 (1991)
Perry et al., *Infec. Immun.,* 32:1295 (1981)
Powell et al., *Appl. Environ. Microbiol.,* 54:655 (1988)
Proudfoot and Whitelaw, "Termination and 3' end processing of eukaryotic RNA", in: Transcription and Splicing (eds. B. D. Hames and D. M. Glover), 1988
Proudfoot, *Trends Biochem. Sci.,* 14:105 (1989)
Raibaud et al., *Ann. Rev. Genet.,* 18:173 (1984)
Richardson, *Crit. Rev. Biochem. Mol. Biol.,* 28:1 (1993)
Rine et al., *Proc. Natl. Acad. Sci. USA,* 80:6750 (1983)
Roggenkamp et al., *Mol. Gen. Genet.,* 202:302 (1986)
Sambrook and Russell, Molecular Cloning: A Laboratory Manual, 3rd edition (Jan. 15, 2001) Cold Spring Harbor Laboratory Press, ISBN: 0879695765
Sanford et al. *Methods Enzymol.,* 217:483 (1993)
Sassone-Corsi and Borelli, *Trends Genet.,* 2:215 (1986)
Shimatake et al. *Nature,* 292:128 (1981)
Shimizu et al., *Mol. Cell. Biol.,* 6:1074 (1986)
Shine et al., Nature, 254:34, (1975)
Smith & Waterman, *J. Mol. Biol.,* 147:195 (1981)
Smith et al. *Mol. Cell. Biol.,* 3: 2156 (1983)
Smith et al., *Proc. Natl. Acad. Sci. USA,* 82: 8404 (1985)
Somkuti et al. *Proc. 4th Eur. Cone. Biotechnology,* 1:412 (1987)
Steitz et al., "Genetic signals and nucleotide sequences in messenger RNA", in: Biological Regulation and Development: Gene Expression (ed. R. F. Goldberger) (1979)
Stinchcomb et al., *J. Mol. Biol.,* 158:157 (1982)
Studier et al., *J. Mol. Biol.,* 189:113 (1986)
Summers and Smith, Texas Agricultural Experiment Station Bulletin No. 1555, 1987
Tabor et al., *Proc. Natl. Acad. Sci. USA,* 82:1074 (1985)
Taketo, *Biochim. Biophys. Acta,* 949:318 (1988)
Vaheri and Pagano, *Virology,* 27:434 (1965)
Van den Berg et al., *Bio/Technology,* 8:135 (1990)
VanDevanter et al., *Nucleic Acids Res.,* 12:6159 (1984)
Vlak et al. *J. Gen. Virol.,* 69:765 (1988)
Walker and Gaastra, eds. (1983) *Techniques in Molecular Biology* (Macmillan Publishing Company, New York)
Walsh, Proteins Biochemistry and Biotechnology, John Wiley & Sons, LTD., West Sussex, England (2002)
Wang et al., *J. Bacteriol.,* 172:949 (1990)
Waterman, *Bulletin of Mathematical Biology,* 46:473 (1984)
Watson, Molecular Biology of the Gene, 4th edition, Benjamin/Cummings Publishing Company, Inc., Menlo Park, Calif. (1987)
Weissmann, "The cloning of interferon and other mistakes", in: Interferon 3 (ed. I. Gresser), 1981
Williams et al., *Genes & Development,* 5:2481, 1991
Wright, *Nature,* 321: 718 (1986)
Yelverton et al., *Nuc. Acids Res.,* 9:731 (1981)
Zhao et al., *Microbiol. Mol. Biol. Rev.,* 63:405 (1999)
Zimmerman, *Biochem. Biophys. Acta.,* 694:227 (1982)

All publications, patents and patent applications and priority U.S. patent application Ser. No. 60/383,370 are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. An expression cassette comprising a nucleotide sequence with the operably linked nucleic acid sequences:

5' Pr-(TIS)$_D$-(IBFP1)$_E$-(CL1)$_G$-ORF-[CL2-ORF]$_L$-(CL3)$_M$-(IBFP2)$_Q$-(SSC)$_R$-(CL4)$_T$-(Ft)$_W$-(Tr)$_X$-3' wherein
the Pr is a promoter sequence,
the TIS encodes a translation initiation sequence,
the IBFP1 encodes a first inclusion body fusion partner comprising an amino acid sequence of any of SEQ ID NOS: 7-14 or a variant thereof, wherein the variant has 75% or greater sequence homology to at least one of SEQ ID NOS: 7-14 and wherein the variant includes a hydrophobic core consisting of residues 22-29 of SEQ ID NO:130,
the CL1 encodes a first cleavable peptide linker,
the ORFs encode a preselected polypeptide,
the CL2 encodes a second cleavable peptide linker,
the CL3 encodes a third cleavable peptide linker,
the IBFP2 encodes a second inclusion body fusion partner comprising an amino acid sequence of any of SEQ ID NOS: 7-14 or a variant thereof, wherein the variant has 75% or greater sequence homology to at least one of SEQ ID NOS: 7-14 and wherein the variant includes the hydrophobic core consisting of residues 22-29 of SEQ ID NO:130,
the SSC is a suppressible stop codon,
the CL4 encodes a fourth cleavable peptide linker,
the Ft encodes a fusion tag, and
the Tr is a transcription terminator sequence,
wherein each of D or X is independently 0 or an integer of 1 to 4,
wherein R is 0 or an integer of 1 to 2,
wherein each of E, G, L, M, Q, T or W is independently 0 or an integer of 1 to 20,
wherein either one or both of a IBFP1 or a IBFP2 is present, and
wherein expression of the nucleic acid sequence produces a tandem polypeptide that forms an inclusion body when expressed in a cell,
wherein at least one of a CL1, a CL2, a CL3 or a CL4 is present.

2. The expression cassette of claim 1 further comprising a nucleic acid sequence that encodes a signal sequence that is operably linked to the amino-terminus or the carboxyl-terminus of the tandem polypeptide.

3. The expression cassette of claim 2, wherein the signal sequence directs the operably linked tandem polypeptide to a periplasmic space, to an inner membrane, or to an outer membrane of the cell.

4. The expression cassette of claim 2, wherein the signal sequence is obtained from a protein selected from the group consisting of a phage fd major coat protein, a phage fd minor coat protein, an alkaline phosphatase, a maltose binding protein, a leucine-specific binding protein, a β-lactamase, a lipoprotein, a LamB and an OmpA.

5. The expression cassette of claim 1, wherein the nucleic acid sequence of either or both of the IBFP1 or the IBFP2 encodes an inclusion body fusion partner that modulates isolation enhancement of an inclusion body formed from the tandem polypeptide.

6. The expression cassette of claim 5, wherein the isolation enhancement of the inclusion body is self-adhesion, solubility, purification stability, resistance to proteolysis, or altered isoelectric point.

7. The expression cassette of claim 1, wherein the promoter includes an operator selected from the group consisting of a lac operator, a lambda phage operator, a β-galactosidase operator, an arabinose operator, a lexA operator, and a trp operator.

8. The expression cassette of claim 1, wherein the promoter is a T7lac promoter, a tac promoter, a lac promoter, a lambda phage promoter, a heat shock promoter, or a chlorella virus promoter.

9. The expression cassette of claim 1, wherein the translation initiation sequence is obtained from a gene encoding a protein selected from the group consisting of a phage T7 gene 10, a phage Qβ A, a phage Qβ coat, a phage Qβ replicase, a phage lambda Cro, a phage fl coat, a phage φX174 A, a phage φX174 B, a phage φX174 E, a lipoprotein, a RecA, a GalE, a GalT, a LacI, a LacZ, aRibosomal L10, a Ribosomal L7/L12, and a RNA polymerase β subunit.

10. The expression cassette of claim 1, wherein each of the first cleavable peptide linker, the second cleavable peptide linker, the third cleavable peptide linker, or the fourth cleavable peptide linker can independently be cleaved by a cleavage agent selected from the group consisting of a palladium, a cyanogen bromide, a Clostripain, a Thrombin, a Trypsin, a Trypsin-like protease, a Carboxypeptidase, an Enterokinase, a Kex 2 protease, an Omp T protease, a Factor Xa protease, a Subtilisin, a HIV protease, a Rhinovirus protease, a Furilisin protease, an IgA protease, a Human Pace protease, a Collagenase, a Plum pos potyvirus, a Poliovirus 2Apro protease, a Poliovirus 3C protease, a Nia protease, a Genenase, a Furin, a Chymotrypsin, an Elastase, a Subtilisin, a Proteinase K, a Pepsin, a Rennin, a microbial aspartic proteases, a Papain, a Ficin, a Bromelain, a Collagenase, a Thermolysin, an Endoprotease Arg-C, an Endoprotease Glu-C, an Endoprotease Lys-C, a Kallikrein and a Plasmin.

11. The expression cassette of claim 1, wherein the ORF encodes a GLP-1, a GLP-2, a PTH, a GRF, a clostripain, or a variant thereof.

12. The expression cassette of claim 1, wherein the ORF contains a suppressible stop codon.

13. The expression cassette of claim 1, wherein the suppressible stop codon is an amber codon or an ochre codon.

14. The expression cassette of claim 13, wherein the suppressible stop codon creates a cleavable peptide linker.

15. The expression cassette of claim 14, wherein the cleavable peptide linker is cleaved by a tissue specific protease.

16. The expression cassette of claim 15, wherein the tissue specific protease is a prostate specific antigen.

17. The expression cassette of claim 1, wherein the fusion tag is a β-gal, a GST, a CAT, a TrpE, a SPA, a SPG, a MBP, a SBD, a $CBD_{CenA}$, a $CBD_{Cex}$, a Biotin-binding domain, a recA, Flag, a poly(Arg), a Poly(Asp), a Glutamine, a poly(His), a poly(Phe), a poly(Cys), a green fluorescent protein, a red fluorescent protein, a yellow fluorescent protein, a cayenne fluorescent protein, a biotin, an avidin, a streptavidin, or an antibody epitope.

18. The expression cassette of claim 1, wherein the termination sequence is a T7 terminator.

19. A nucleic acid construct comprising a vector operably linked to the expression cassette of claim 1.

20. The nucleic acid construct of claim 19, wherein the vector is a virus, a plasmid, a phagemid, a bacterial artificial chromosome, a yeast artificial chromosome, a bacteriophage, an f-factor, or a cosmid.

21. A cell comprising the nucleic acid construct of claim 19.

22. The cell of claim 21, wherein the cell is a prokaryotic cell or a eukaryotic cell.

23. The cell of claim 21, wherein the cell is a bacterium.

24. The cell of claim 23, wherein the bacterium is *Escherichia coli*.

25. The cell of claim 21, wherein the cell is a yeast cell, an insect cell or a mammalian cell.

26. The expression cassette of claim 1, wherein at least one of the first cleavable peptide linker, the second cleavable peptide linker, the third cleavable peptide linker, and the fourth cleavable peptide linker is cleavable by palladium.

27. The expression cassette of claim 1, wherein the amino acid at residue 23 of SEQ ID NO:130 is threonine.

28. The expression cassette of claim 1, wherein the amino acid at residue 28 of SEQ ID NO:130 is lysine.

29. The expression cassette of claim 1, wherein the amino acid at residue 23 of SEQ ID NO:130 is threonine and the amino acid at residue 28 of SEQ ID NO:130 is lysine.

30. An expression cassette comprising a nucleotide sequence with the operably linked nucleic acid sequences:

5'  Pr-$(TIS)_D$$(IBFP1)_E$-$(CL1)_G$-ORF-$[CL2-ORF]_L$-$(CL3)_M$-$(IBFP2)_Q$-$(SSC)_R$-$(CL4)_T$-$(Ft)_W$-$(Tr)_X$-3' wherein
the Pr is a promoter sequence,
the TIS encodes a translation initiation sequence,
the IBFP1 encodes a first inclusion body fusion partner comprising an amino acid sequence of any of SEQ ID NOS: 2-6, 12, or 15 or a variant thereof, wherein the variant has 75% or greater sequence homology to at least one of SEQ ID NOS: 2-6, 12, or 15 and wherein the variant includes a hydrophobic core consisting of the amino acid sequence of SEQ ID NO:92 or the amino acid sequence of SEQ ID NO:92 with a single amino acid substitution therein,
the CL1 encodes a first cleavable peptide linker,
the ORFs encode a preselected polypeptide,
the CL2 encodes a second cleavable peptide linker,
the CL3 encodes a third cleavable peptide linker,
the IBFP2 encodes a second inclusion body fusion partner comprising an amino acid sequence of any of SEQ ID NOS: 2-6, 12, or 15 or a variant thereof, wherein the variant has 75% or greater sequence homology to at least one of SEQ ID NOS: 2-6, 12, or 15 and wherein the variant includes the hydrophobic core consisting of SEQ ID NO:92 or a sequence having a single amino acid substitution of SEQ ID NO:92,
the SSC is a suppressible stop codon,
the CL4 encodes a fourth cleavable peptide linker,
the Ft encodes a fusion tag, and
the Tr is a transcription terminator sequence,
wherein each of D or X is independently 0 or an integer of 1 to 4,
wherein R is 0 or an integer of 1 to 2,
wherein each of E, G, L, M, Q, T or W is independently 0 or an integer of 1 to 20,
wherein either one or both of a IBFP1 or a IBFP2 is present, and
wherein expression of the nucleic acid sequence produces a tandem polypeptide that forms an inclusion body when expressed in a cell,
wherein at least one of a CL1, a CL2, a CL3 or a CL4 is present.

31. The expression cassette of claim 30, wherein the amino acid substitution is at residue 4 of SEQ ID NO:92.

* * * * *

SEQUENCE LISTING

<160> NUMBER OF SEQ ID NOS: 149

<210> SEQ ID NO 1
<211> LENGTH: 29
<212> TYPE: PRT
<213> ORGANISM: Artificial Sequence
<220> FEATURE:
<223> OTHER INFORMATION: A synthetic sequence of an inclusion body
      fusion partner.

<400> SEQUENCE: 1

Gly Ser Gly Gln Gly Gln Ala Gln Tyr Leu Ser Ala Ser Cys Val Val
1               5                   10                  15

Phe Thr Asn Tyr Ser Gly Asp Thr Ala Ser Gln Val Asp
            20                  25

<210> SEQ ID NO 2
<211> LENGTH: 29
<212> TYPE: PRT
<213> ORGANISM: Artificial Sequence
<220> FEATURE:
<223> OTHER INFORMATION: A synthetic sequence of an inclusion body
      fusion partner.

<400> SEQUENCE: 2

Gly Ser Gly Gln Gly Gln Ala Gln Tyr Leu Ala Ala Ser Leu Val Val
1               5                   10                  15

Phe Thr Asn Tyr Ser Gly Asp Thr Ala Ser Gln Val Asp
            20                  25

<210> SEQ ID NO 3
<211> LENGTH: 24
<212> TYPE: PRT
<213> ORGANISM: Artificial Sequence
<220> FEATURE:
<223> OTHER INFORMATION: A synthetic sequence of an inclusion body
      fusion partner.

<400> SEQUENCE: 3

Gly Ser Gln Tyr Leu Ala Ala Ser Leu Val Val Phe Thr Asn Tyr Ser
1               5                   10                  15

Gly Asp Thr Ala Ser Gln Val Asp
            20

<210> SEQ ID NO 4
<211> LENGTH: 23
<212> TYPE: PRT
<213> ORGANISM: Artificial Sequence
<220> FEATURE:
<223> OTHER INFORMATION: A synthetic sequence of an inclusion body
      fusion partner.

<400> SEQUENCE: 4

Gly Ser Gly Gln Gly Gln Ala Gln Tyr Leu Ala Ala Ser Leu Val Val
1               5                   10                  15

Phe Thr Asn Tyr Ser Gly Asp
            20

<210> SEQ ID NO 5
<211> LENGTH: 18
<212> TYPE: PRT
<213> ORGANISM: Artificial Sequence
<220> FEATURE:
<223> OTHER INFORMATION: A synthetic sequence of an inclusion body
      fusion partner.

<400> SEQUENCE: 5

Gly Ser Gln Tyr Leu Ala Ala Ser Leu Val Val Phe Thr Asn Tyr Ser
1               5                   10                  15

Gly Asp

<210> SEQ ID NO 6
<211> LENGTH: 24
<212> TYPE: PRT
<213> ORGANISM: Artificial Sequence
<220> FEATURE:
<223> OTHER INFORMATION: A synthetic sequence of an inclusion body
      fusion partner.

<400> SEQUENCE: 6

Gly Ser Gln Tyr Leu Ala Ala Val Leu Val Val Phe Thr Asn Tyr Ser
1               5                   10                  15

Gly Asp Thr Ala Ser Gln Val Asp
            20

<210> SEQ ID NO 7
<211> LENGTH: 29
<212> TYPE: PRT
<213> ORGANISM: Artificial Sequence
<220> FEATURE:
<223> OTHER INFORMATION: A synthetic sequence of an inclusion body
      fusion partner.

<400> SEQUENCE: 7

Gly Ser Gly Gln Gly Gln Ala Gln Tyr Leu Thr Ala Ser Leu Val Lys
1               5                   10                  15

Phe Thr Asn Tyr Ser Gly Asp Thr Ala Ser Gln Val Asp
            20                  25

<210> SEQ ID NO 8
<211> LENGTH: 29
<212> TYPE: PRT
<213> ORGANISM: Artificial Sequence
<220> FEATURE:
<223> OTHER INFORMATION: A synthetic sequence of an inclusion body
      fusion partner.

<400> SEQUENCE: 8

Gly Ser Gly Gln Gly Gln Ala Gln Tyr Leu Thr Ala Ser Leu Val Gln
1               5                   10                  15

Phe Thr Asn Tyr Ser Gly Asp Thr Ala Ser Gln Val Asp
            20                  25

<210> SEQ ID NO 9
<211> LENGTH: 29
<212> TYPE: PRT
<213> ORGANISM: Artificial Sequence
<220> FEATURE:
<223> OTHER INFORMATION: A synthetic sequence of an inclusion body
      fusion partner.

<400> SEQUENCE: 9

Gly Ser Gly Gln Gly Gln Ala Gln Tyr Leu Pro Ala Ser Leu Val Lys
1               5                   10                  15

Phe Thr Asn Tyr Ser Gly Asp Thr Ala Ser Gln Val Asp
            20                  25

<210> SEQ ID NO 10
<211> LENGTH: 29
<212> TYPE: PRT

```
<213> ORGANISM: Artificial Sequence
<220> FEATURE:
<223> OTHER INFORMATION: A synthetic sequence of an inclusion body
      fusion partner.

<400> SEQUENCE: 10

Gly Ser Gly Gln Gly Gln Ala Gln Tyr Leu Pro Ala Ser Leu Val Gln
1               5                   10                  15

Phe Thr Asn Tyr Ser Gly Asp Thr Ala Ser Gln Val Asp
            20                  25

<210> SEQ ID NO 11
<211> LENGTH: 29
<212> TYPE: PRT
<213> ORGANISM: Artificial Sequence
<220> FEATURE:
<223> OTHER INFORMATION: A synthetic sequence of an inclusion body
      fusion partner.

<400> SEQUENCE: 11

Gly Ser Gly Gln Gly Gln Ala Gln Tyr Leu Ala Ala Ser Leu Val Lys
1               5                   10                  15

Phe Thr Asn Tyr Ser Gly Asp Thr Ala Ser Gln Val Asp
            20                  25

<210> SEQ ID NO 12
<211> LENGTH: 29
<212> TYPE: PRT
<213> ORGANISM: Artificial Sequence
<220> FEATURE:
<223> OTHER INFORMATION: A synthetic sequence of an inclusion body
      fusion partner.

<400> SEQUENCE: 12

Gly Ser Gly Gln Gly Gln Ala Gln Tyr Leu Ala Ala Ser Leu Val Gln
1               5                   10                  15

Phe Thr Asn Tyr Ser Gly Asp Thr Ala Ser Gln Val Asp
            20                  25

<210> SEQ ID NO 13
<211> LENGTH: 29
<212> TYPE: PRT
<213> ORGANISM: Artificial Sequence
<220> FEATURE:
<223> OTHER INFORMATION: A synthetic sequence of an inclusion body
      fusion partner.

<400> SEQUENCE: 13

Gly Ser Gly Gln Gly Gln Ala Gln Tyr Leu Ser Ala Ser Leu Val Lys
1               5                   10                  15

Phe Thr Asn Tyr Ser Gly Asp Thr Ala Ser Gln Val Asp
            20                  25

<210> SEQ ID NO 14
<211> LENGTH: 29
<212> TYPE: PRT
<213> ORGANISM: Artificial Sequence
<220> FEATURE:
<223> OTHER INFORMATION: A synthetic sequence of an inclusion body
      fusion partner.

<400> SEQUENCE: 14

Gly Ser Gly Gln Gly Gln Ala Gln Tyr Leu Ser Ala Ser Leu Val Gln
1               5                   10                  15

Phe Thr Asn Tyr Ser Gly Asp Thr Ala Ser Gln Val Asp
```

```
                    20                  25

<210> SEQ ID NO 15
<211> LENGTH: 29
<212> TYPE: PRT
<213> ORGANISM: Artificial Sequence
<220> FEATURE:
<223> OTHER INFORMATION: A synthetic sequence of an inclusion body
      fusion partner.

<400> SEQUENCE: 15

Gly Ser Gly Gln Gly Gln Ala Gln Tyr Leu Ala Ala Val Leu Val Val
 1               5                  10                  15

Phe Thr Asn Tyr Ser Gly Asp Thr Ala Ser Gln Val Asp
                20                  25

<210> SEQ ID NO 16
<211> LENGTH: 87
<212> TYPE: DNA
<213> ORGANISM: Artificial Sequence
<220> FEATURE:
<223> OTHER INFORMATION: A synthetic sequence of an inclusion body
      fusion partner.

<400> SEQUENCE: 16
ggcagtggcc agggacaggc tcaatatcta tcggcctcct gcgttgtgtt caccaactac      60
tcgggcgaca cggccagcca ggtggac                                         87

<210> SEQ ID NO 17
<211> LENGTH: 87
<212> TYPE: DNA
<213> ORGANISM: Artificial Sequence
<220> FEATURE:
<223> OTHER INFORMATION: A synthetic sequence of an inclusion body
      fusion partner.

<400> SEQUENCE: 17
ggatccggcc agggacaggc tcaatatcta gcggcctcct tggttgtgtt caccaactac      60
tcgggcgaca cggccagcca ggtggac                                         87

<210> SEQ ID NO 18
<211> LENGTH: 87
<212> TYPE: DNA
<213> ORGANISM: Artificial Sequence
<220> FEATURE:
<223> OTHER INFORMATION: A synthetic sequence of an inclusion body
      fusion partner.

<400> SEQUENCE: 18
ggatccggcc agggtcaggc tcaatatctg gctgcctccc tggttgtgtt caccaactac      60
tcgggcgaca cggccagcca ggtggac                                         87

<210> SEQ ID NO 19
<211> LENGTH: 69
<212> TYPE: DNA
<213> ORGANISM: Artificial Sequence
<220> FEATURE:
<223> OTHER INFORMATION: A synthetic sequence of an inclusion body
      fusion partner.

<400> SEQUENCE: 19
ggatccggcc agggtcaggc tcaatatctg gctgcctccc tggttgtgtt caccaactac      60
tcgggcgac                                                             69
```

```
<210> SEQ ID NO 20
<211> LENGTH: 54
<212> TYPE: DNA
<213> ORGANISM: Artificial Sequence
<220> FEATURE:
<223> OTHER INFORMATION: A synthetic sequence of an inclusion body
      fusion partner.

<400> SEQUENCE: 20
ggatcccaat atctggctgc ctccctggtt gtgttcacca actactcggg cgac            54

<210> SEQ ID NO 21
<211> LENGTH: 72
<212> TYPE: DNA
<213> ORGANISM: Artificial Sequence
<220> FEATURE:
<223> OTHER INFORMATION: A synthetic sequence of an inclusion body
      fusion partner.

<400> SEQUENCE: 21
ggatcccaat atctggctgc cgtgctggtt gtgttcacca actactcggg cgacacggcc      60
agccaggtgg ac                                                         72

<210> SEQ ID NO 22
<211> LENGTH: 87
<212> TYPE: DNA
<213> ORGANISM: Artificial Sequence
<220> FEATURE:
<223> OTHER INFORMATION: A synthetic sequence of an inclusion body
      fusion partner.

<400> SEQUENCE: 22
ggatccggcc agggtcaggc tcaatatctg acggcctccc tggttaaatt caccaactac      60
tcgggcgaca cggccagcca ggtggac                                         87

<210> SEQ ID NO 23
<211> LENGTH: 87
<212> TYPE: DNA
<213> ORGANISM: Artificial Sequence
<220> FEATURE:
<223> OTHER INFORMATION: A synthetic sequence of an inclusion body
      fusion partner.

<400> SEQUENCE: 23
ggatccggcc agggtcaggc tcaatatctg acggcctccc tggttcaatt caccaactac      60
tcgggcgaca cggccagcca ggtggac                                         87

<210> SEQ ID NO 24
<211> LENGTH: 87
<212> TYPE: DNA
<213> ORGANISM: Artificial Sequence
<220> FEATURE:
<223> OTHER INFORMATION: A synthetic sequence of an inclusion body
      fusion partner.

<400> SEQUENCE: 24
ggatccggcc agggtcaggc tcaatatctg ccggcctccc tggttaaatt caccaactac      60
tcgggcgaca cggccagcca ggtggac                                         87

<210> SEQ ID NO 25
<211> LENGTH: 87
<212> TYPE: DNA
<213> ORGANISM: Artificial Sequence
<220> FEATURE:
```

```
<223> OTHER INFORMATION: A synthetic sequence of an inclusion body
      fusion partner.

<400> SEQUENCE: 25
ggatccggcc agggtcaggc tcaatatctg ccggcctccc tggttcaatt caccaactac      60
tcgggcgaca cggccagcca ggtggac                                          87

<210> SEQ ID NO 26
<211> LENGTH: 87
<212> TYPE: DNA
<213> ORGANISM: Artificial Sequence
<220> FEATURE:
<223> OTHER INFORMATION: A synthetic sequence of an inclusion body
      fusion partner.

<400> SEQUENCE: 26
ggatccggcc agggtcaggc tcaatatctg gcggcctccc tggttaaatt caccaactac      60
tcgggcgaca cggccagcca ggtggac                                          87

<210> SEQ ID NO 27
<211> LENGTH: 87
<212> TYPE: DNA
<213> ORGANISM: Artificial Sequence
<220> FEATURE:
<223> OTHER INFORMATION: A synthetic sequence of an inclusion body
      fusion partner.

<400> SEQUENCE: 27
ggatccggcc agggtcaggc tcaatatctg gcggcctccc tggttcaatt caccaactac      60
tcgggcgaca cggccagcca ggtggac                                          87

<210> SEQ ID NO 28
<211> LENGTH: 87
<212> TYPE: DNA
<213> ORGANISM: Artificial Sequence
<220> FEATURE:
<223> OTHER INFORMATION: A synthetic sequence of an inclusion body
      fusion partner.

<400> SEQUENCE: 28
ggatccggcc agggtcaggc tcaatatctg tcggcctccc tggttaaatt caccaactac      60
tcgggcgaca cggccagcca ggtggac                                          87

<210> SEQ ID NO 29
<211> LENGTH: 87
<212> TYPE: DNA
<213> ORGANISM: Artificial Sequence
<220> FEATURE:
<223> OTHER INFORMATION: A synthetic sequence of an inclusion body
      fusion partner.

<400> SEQUENCE: 29
ggatccggcc agggtcaggc tcaatatctg tcggcctccc tggttcaatt caccaactac      60
tcgggcgaca cggccagcca ggtggac                                          87

<210> SEQ ID NO 30
<211> LENGTH: 87
<212> TYPE: DNA
<213> ORGANISM: Artificial Sequence
<220> FEATURE:
<223> OTHER INFORMATION: A synthetic sequence of an inclusion body
      fusion partner.

<400> SEQUENCE: 30
```

```
ggatccggcc agggtcaggc tcaatatctg gctgccgtgc tggttgtgtt caccaactac    60
tcgggcgaca cggccagcca ggtggac                                        87
```

<210> SEQ ID NO 31
<211> LENGTH: 30
<212> TYPE: PRT
<213> ORGANISM: Unknown
<220> FEATURE:
<223> OTHER INFORMATION: GLP-1(7-36).

<400> SEQUENCE: 31

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 32
<211> LENGTH: 31
<212> TYPE: PRT
<213> ORGANISM: Unknown
<220> FEATURE:
<223> OTHER INFORMATION: GLP-1(7-37).

<400> SEQUENCE: 32

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 33
<211> LENGTH: 30
<212> TYPE: PRT
<213> ORGANISM: Artificial Sequence
<220> FEATURE:
<223> OTHER INFORMATION: A synthetic sequence of a modified
      preselected peptide.

<400> SEQUENCE: 33

His Ala Glu Gly Thr Phe Thr Ser Asp Val Ser Ser Tyr Leu Glu Gly
1               5                   10                  15

Gln Ala Ala Arg Glu Phe Ile Ala Trp Leu Val Lys Gly Arg
            20                  25                  30

<210> SEQ ID NO 34
<211> LENGTH: 31
<212> TYPE: PRT
<213> ORGANISM: Artificial Sequence
<220> FEATURE:
<223> OTHER INFORMATION: A synthetic sequence of a modified
      preselected peptide.

<400> SEQUENCE: 34

His Ala Glu Gly Thr Phe Thr Ser Asp Val Ser Ser Tyr Leu Glu Gly
1               5                   10                  15

Gln Ala Ala Arg Glu Phe Ile Ala Trp Leu Val Lys Gly Arg Gly
            20                  25                  30

<210> SEQ ID NO 35
<211> LENGTH: 34
<212> TYPE: PRT
<213> ORGANISM: Unknown
<220> FEATURE:
<223> OTHER INFORMATION: GLP-2(1-34).

```
<400> SEQUENCE: 35

His Ala Asp Gly Ser Phe Ser Asp Gly Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp Arg

<210> SEQ ID NO 36
<211> LENGTH: 33
<212> TYPE: PRT
<213> ORGANISM: Unknown
<220> FEATURE:
<223> OTHER INFORMATION: GLP-2(1-33).

<400> SEQUENCE: 36

His Ala Asp Gly Ser Phe Ser Asp Gly Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 37
<211> LENGTH: 33
<212> TYPE: PRT
<213> ORGANISM: Artificial Sequence
<220> FEATURE:
<223> OTHER INFORMATION: A synthetic sequence of a modified preselected
      peptide.

<400> SEQUENCE: 37

His Gly Asp Gly Ser Phe Ser Asp Gly Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 38
<211> LENGTH: 34
<212> TYPE: PRT
<213> ORGANISM: Artificial Sequence
<220> FEATURE:
<223> OTHER INFORMATION: A synthetic sequence of a modified preselected
      peptide.

<400> SEQUENCE: 38

His Gly Asp Gly Ser Phe Ser Asp Gly Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp Arg

<210> SEQ ID NO 39
<211> LENGTH: 44
<212> TYPE: PRT
<213> ORGANISM: Unknown
<220> FEATURE:
<223> OTHER INFORMATION: GRF(1-44).

<400> SEQUENCE: 39

Tyr Ala Asp Ala Ile Phe Thr Asn Ser Tyr Arg Lys Val Leu Gly Gln
1               5                   10                  15
```

```
Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Leu
        35                  40

<210> SEQ ID NO 40
<211> LENGTH: 34
<212> TYPE: PRT
<213> ORGANISM: Unknown
<220> FEATURE:
<223> OTHER INFORMATION: PTH(1-34).

<400> SEQUENCE: 40

Ser Val Ser Glu Ile Gln Leu Met His Asn Leu Gly Lys His Leu Asn
 1               5                  10                  15

Ser Met Glu Arg Val Glu Trp Leu Arg Lys Lys Leu Gln Asp Val His
            20                  25                  30

Asn Phe

<210> SEQ ID NO 41
<211> LENGTH: 37
<212> TYPE: PRT
<213> ORGANISM: Unknown
<220> FEATURE:
<223> OTHER INFORMATION: PTH(1-37).

<400> SEQUENCE: 41

Ser Val Ser Glu Ile Gln Leu Met His Asn Leu Gly Lys His Leu Asn
 1               5                  10                  15

Ser Met Glu Arg Val Glu Trp Leu Arg Lys Lys Leu Gln Asp Val His
            20                  25                  30

Asn Phe Val Ala Leu
        35

<210> SEQ ID NO 42
<211> LENGTH: 84
<212> TYPE: PRT
<213> ORGANISM: Unknown
<220> FEATURE:
<223> OTHER INFORMATION: PTH(1-84).

<400> SEQUENCE: 42

Ser Val Ser Glu Ile Gln Leu Met His Asn Leu Gly Lys His Leu Asn
 1               5                  10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asp Lys Ala Asp Val Asn Val Leu Thr Lys
65                  70                  75                  80

Ala Lys Ser Gln

<210> SEQ ID NO 43
<211> LENGTH: 12
<212> TYPE: PRT
<213> ORGANISM: Unknown
<220> FEATURE:
<223> OTHER INFORMATION: Amyloid P Component (27-38).

<400> SEQUENCE: 43
```

```
Glu Lys Pro Leu Gln Asn Phe Thr Leu Cys Phe Arg
1               5                  10

<210> SEQ ID NO 44
<211> LENGTH: 17
<212> TYPE: PRT
<213> ORGANISM: Unknown
<220> FEATURE:
<223> OTHER INFORMATION: (Tyr0)-Fibrinopeptide A.

<400> SEQUENCE: 44

Tyr Ala Asp Ser Gly Glu Gly Asp Phe Leu Ala Glu Gly Gly Gly Val
1               5                  10                  15

Arg

<210> SEQ ID NO 45
<211> LENGTH: 10
<212> TYPE: PRT
<213> ORGANISM: Unknown
<220> FEATURE:
<223> OTHER INFORMATION: Urechistachykinin II.

<400> SEQUENCE: 45

Ala Ala Gly Met Gly Phe Phe Gly Ala Arg
1               5                  10

<210> SEQ ID NO 46
<211> LENGTH: 17
<212> TYPE: PRT
<213> ORGANISM: Unknown
<220> FEATURE:
<223> OTHER INFORMATION: Amyloid  B-Protein (12-28).

<400> SEQUENCE: 46

Val His His Gln Lys Leu Val Phe Phe Ala Glu Asp Val Gly Ser Asn
1               5                  10                  15

Lys

<210> SEQ ID NO 47
<211> LENGTH: 14
<212> TYPE: PRT
<213> ORGANISM: Unknown
<220> FEATURE:
<223> OTHER INFORMATION: Amyloid  B-Protein (22-35).

<400> SEQUENCE: 47

Glu Asp Val Gly Ser Asn Lys Gly Ala Ile Ile Gly Leu Met
1               5                  10

<210> SEQ ID NO 48
<211> LENGTH: 29
<212> TYPE: PRT
<213> ORGANISM: Camelus

<400> SEQUENCE: 48

Tyr Gly Phe Met Thr Ser Glu Lys Ser Gln Thr Pro Leu Val Thr Leu
1               5                  10                  15

Phe Lys Asn Ala Ile Ile Lys Asn Ala His Lys Gly Gln
            20                  25

<210> SEQ ID NO 49
<211> LENGTH: 25
<212> TYPE: PRT
<213> ORGANISM: Sus scrofa
```

<400> SEQUENCE: 49

Val Gln Tyr Pro Val Glu His Pro Asp Lys Phe Leu Lys Phe Gly Met
1               5                   10                  15

Thr Pro Ser Lys Gly Val Leu Phe Tyr
            20                  25

<210> SEQ ID NO 50
<211> LENGTH: 21
<212> TYPE: PRT
<213> ORGANISM: Mus musculus

<400> SEQUENCE: 50

Cys Ser Cys Asn Ser Trp Leu Asp Lys Glu Cys Val Tyr Phe Cys His
1               5                   10                  15

Leu Asp Ile Ile Trp
            20

<210> SEQ ID NO 51
<211> LENGTH: 90
<212> TYPE: DNA
<213> ORGANISM: Unknown
<220> FEATURE:
<223> OTHER INFORMATION: GLP-1(7-36).

<400> SEQUENCE: 51
catgctgagg gtaccttcac ctccgacgtt tcctcctacc tggaaggtca ggctgctaaa    60
gaattcatcg cttggctggt taaaggtcgt                                    90

<210> SEQ ID NO 52
<211> LENGTH: 93
<212> TYPE: DNA
<213> ORGANISM: Unknown
<220> FEATURE:
<223> OTHER INFORMATION: GLP-1(7-37).

<400> SEQUENCE: 52
catgctgagg gtaccttcac ctccgacgtt tcctcctacc tggaaggtca ggctgctaaa    60
gaattcatcg cttggctggt taaaggtcgt ggt                                93

<210> SEQ ID NO 53
<211> LENGTH: 90
<212> TYPE: DNA
<213> ORGANISM: Artificial Sequence
<220> FEATURE:
<223> OTHER INFORMATION: A synthetic sequence of a modified preselected
      peptide.

<400> SEQUENCE: 53
catgctgagg gtaccttcac ctccgacgtt tcctcctacc tggaaggtca ggctgctcgt    60
gaattcatcg cttggctggt taaaggtcgt                                    90

<210> SEQ ID NO 54
<211> LENGTH: 93
<212> TYPE: DNA
<213> ORGANISM: Artificial Sequence
<220> FEATURE:
<223> OTHER INFORMATION: A synthetic sequence of a modified preselected
      peptide.

<400> SEQUENCE: 54
catgctgagg gtaccttcac ctccgacgtt tcctcctacc tggaaggtca ggctgctcgt    60

```
gaattcatcg cttggctggt taaaggtcgt ggt                                    93

<210> SEQ ID NO 55
<211> LENGTH: 102
<212> TYPE: DNA
<213> ORGANISM: Unknown
<220> FEATURE:
<223> OTHER INFORMATION: GLP-2(1-34).

<400> SEQUENCE: 55
catgctgatg gttctttctc tgatgagatg aacaccattc ttgataatct tgccgcccgt      60
gactttatca actggttgat tcagaccaaa atcactgacc gt                        102

<210> SEQ ID NO 56
<211> LENGTH: 99
<212> TYPE: DNA
<213> ORGANISM: Unknown
<220> FEATURE:
<223> OTHER INFORMATION: GLP-2(1-33).

<400> SEQUENCE: 56
catgctgatg gttctttctc tgatgagatg aacaccattc ttgataatct tgccgcccgt      60
gactttatca actggttgat tcagaccaaa atcactgac                             99

<210> SEQ ID NO 57
<211> LENGTH: 99
<212> TYPE: DNA
<213> ORGANISM: Artificial Sequence
<220> FEATURE:
<223> OTHER INFORMATION: A synthetic sequence of a modified preselected
      peptide.

<400> SEQUENCE: 57
catggtgatg gttctttctc tgatgagatg aacaccattc ttgataatct tgccgcccgt      60
gactttatca actggttgat tcagaccaaa atcactgac                             99

<210> SEQ ID NO 58
<211> LENGTH: 102
<212> TYPE: DNA
<213> ORGANISM: Artificial Sequence
<220> FEATURE:
<223> OTHER INFORMATION: A synthetic sequence of a modified preselected
      peptide.

<400> SEQUENCE: 58
catggtgatg gttctttctc tgatgagatg aacaccattc ttgataatct tgccgcccgt      60
gactttatca actggttgat tcagaccaaa atcactgacc gt                        102

<210> SEQ ID NO 59
<211> LENGTH: 132
<212> TYPE: DNA
<213> ORGANISM: Unknown
<220> FEATURE:
<223> OTHER INFORMATION: GRF(1-44).

<400> SEQUENCE: 59
tacgctgacg ctatcttcac caactcttac cgtaaagttc tgggtcagct gtctgctcgt      60
aaactgctgc aggacatcat gtcccgtcag cagggtgaat ctaaccagga acgtggtgct    120
cgtgctcgtc tg                                                        132

<210> SEQ ID NO 60
<211> LENGTH: 102
```

```
<212> TYPE: DNA
<213> ORGANISM: Unknown
<220> FEATURE:
<223> OTHER INFORMATION: PTH(1-34).

<400> SEQUENCE: 60
tctgtttctg aaatccagct gatgcacaac ctgggtaaac acctgaactc tatggaacgt     60
gttgaatggc tgcgtaaaaa actgcaggac gttcacaact tc                       102

<210> SEQ ID NO 61
<211> LENGTH: 111
<212> TYPE: DNA
<213> ORGANISM: Unknown
<220> FEATURE:
<223> OTHER INFORMATION: PTH(1-37).

<400> SEQUENCE: 61
tctgtttctg aaatccagct gatgcacaac ctgggtaaac acctgaactc tatggaacgt     60
gttgaatggc tgcgtaaaaa actgcaggac gttcacaact tcgttgctct g             111

<210> SEQ ID NO 62
<211> LENGTH: 252
<212> TYPE: DNA
<213> ORGANISM: Unknown
<220> FEATURE:
<223> OTHER INFORMATION: PTH(1-84).

<400> SEQUENCE: 62
tctgtttctg aaatccagct gatgcacaac ctgggtaaac acctgaactc tatggaacgt     60
gttgaatggc tgcgtaaaaa actgcaggac gttcacaact tcgttgctct gggtgctccg    120
ctggctccgc gtgacgctgg ttcccagcgt ccgcgtaaaa aagaagacaa cgttctggtt    180
gaatcccacg aaaaatccct gggtgaagct gacaaagctg acgttaacgt tctgaccaaa    240
gctaaatccc ag                                                        252

<210> SEQ ID NO 63
<211> LENGTH: 36
<212> TYPE: DNA
<213> ORGANISM: Unknown
<220> FEATURE:
<223> OTHER INFORMATION: Amyloid P Component (27-38).

<400> SEQUENCE: 63
gaaaaaccgc tgcagaactt caccctgtgc ttccgt                              36

<210> SEQ ID NO 64
<211> LENGTH: 51
<212> TYPE: DNA
<213> ORGANISM: Unknown
<220> FEATURE:
<223> OTHER INFORMATION: (Tyr0)-Fibrinopeptide A.

<400> SEQUENCE: 64
tacgctgatt ccggtgaagg tgatttcctg gctgaaggtg gtggtgtccg t             51

<210> SEQ ID NO 65
<211> LENGTH: 30
<212> TYPE: DNA
<213> ORGANISM: Unknown
<220> FEATURE:
<223> OTHER INFORMATION: Urechistachykinin II.

<400> SEQUENCE: 65
```

-continued

```
gctgctggta tgggtttctt cggtgcgcgt                                      30
```

<210> SEQ ID NO 66
<211> LENGTH: 51
<212> TYPE: DNA
<213> ORGANISM: Unknown
<220> FEATURE:
<223> OTHER INFORMATION: Amyloid B-Protein (12-28).

<400> SEQUENCE: 66

```
gtccatcatc agaaactggt cttcttcgct gaagatgtcg gttccaacaa a             51
```

<210> SEQ ID NO 67
<211> LENGTH: 42
<212> TYPE: DNA
<213> ORGANISM: Unknown
<220> FEATURE:
<223> OTHER INFORMATION: Amyloid B-Protein (22-35).

<400> SEQUENCE: 67

```
gaagatgtcg gttccaacaa aggtgctatt attggtctga tg                       42
```

<210> SEQ ID NO 68
<211> LENGTH: 93
<212> TYPE: DNA
<213> ORGANISM: Camelus

<400> SEQUENCE: 68

```
tacggtggtt tcatgacctc cgaaaaatcc cagaccccgc tggtcaccct gttcaaaaac    60
gctattatta aaacgctcaa taaaaaggt cag                                  93
```

<210> SEQ ID NO 69
<211> LENGTH: 75
<212> TYPE: DNA
<213> ORGANISM: Sus scrofa

<400> SEQUENCE: 69

```
gtccagtacc cggtcgaaca tccggataaa ttcctgaaat tcggtatgac cccgtccaaa    60
ggtgtcctgt ctac                                                      75
```

<210> SEQ ID NO 70
<211> LENGTH: 63
<212> TYPE: DNA
<213> ORGANISM: Mus musculus

<400> SEQUENCE: 70

```
tgctcctgca actcctggct ggataaagaa tgcgtctact tctgccatct ggatattatt    60
tgg                                                                  63
```

<210> SEQ ID NO 71
<211> LENGTH: 8
<212> TYPE: PRT
<213> ORGANISM: Artificial Sequence
<220> FEATURE:
<223> OTHER INFORMATION: A synthetic sequence of a cleavable peptide
      linker.

<400> SEQUENCE: 71

Ala Phe Leu Gly Pro Gly Asp Arg
 1               5

<210> SEQ ID NO 72
<211> LENGTH: 4

```
<212> TYPE: PRT
<213> ORGANISM: Artificial Sequence
<220> FEATURE:
<223> OTHER INFORMATION: A synthetic sequence of a cleavable peptide
      linker.

<400> SEQUENCE: 72

Val Asp Asp Arg
1

<210> SEQ ID NO 73
<211> LENGTH: 4
<212> TYPE: PRT
<213> ORGANISM: Artificial Sequence
<220> FEATURE:
<223> OTHER INFORMATION: A synthetic sequence of a cleavable peptide
      linker.

<400> SEQUENCE: 73

Gly Ser Asp Arg
1

<210> SEQ ID NO 74
<211> LENGTH: 4
<212> TYPE: PRT
<213> ORGANISM: Artificial Sequence
<220> FEATURE:
<223> OTHER INFORMATION: A synthetic sequence of a cleavable peptide
      linker.

<400> SEQUENCE: 74

Ile Thr Asp Arg
1

<210> SEQ ID NO 75
<211> LENGTH: 4
<212> TYPE: PRT
<213> ORGANISM: Artificial Sequence
<220> FEATURE:
<223> OTHER INFORMATION: A synthetic sequence of a cleavable peptide
      linker.

<400> SEQUENCE: 75

Pro Gly Asp Arg
1

<210> SEQ ID NO 76
<211> LENGTH: 24
<212> TYPE: DNA
<213> ORGANISM: Artificial Sequence
<220> FEATURE:
<223> OTHER INFORMATION: A synthetic sequence of a cleavable peptide
      linker.

<400> SEQUENCE: 76
gctttcctgg ggccgggtga tcgt                                              24

<210> SEQ ID NO 77
<211> LENGTH: 12
<212> TYPE: DNA
<213> ORGANISM: Artificial Sequence
<220> FEATURE:
<223> OTHER INFORMATION: A synthetic sequence of a cleavable peptide
      linker.

<400> SEQUENCE: 77
gtcgacgatc gt                                                           12
```

<210> SEQ ID NO 78
<211> LENGTH: 12
<212> TYPE: DNA
<213> ORGANISM: Artificial Sequence
<220> FEATURE:
<223> OTHER INFORMATION: A synthetic sequence of a cleavable peptide
      linker.

<400> SEQUENCE: 78
ggatctgacc gt                                                          12

<210> SEQ ID NO 79
<211> LENGTH: 12
<212> TYPE: DNA
<213> ORGANISM: Artificial Sequence
<220> FEATURE:
<223> OTHER INFORMATION: A synthetic sequence of a cleavable peptide
      linker.

<400> SEQUENCE: 79
atcactgacc gt                                                          12

<210> SEQ ID NO 80
<211> LENGTH: 12
<212> TYPE: DNA
<213> ORGANISM: Artificial Sequence
<220> FEATURE:
<223> OTHER INFORMATION: A synthetic sequence of a cleavable peptide
      linker.

<400> SEQUENCE: 80
ccgggtgacc gt                                                          12

<210> SEQ ID NO 81
<211> LENGTH: 8
<212> TYPE: PRT
<213> ORGANISM: Artificial Sequence
<220> FEATURE:
<223> OTHER INFORMATION: A synthetic FLAG sequence.

<400> SEQUENCE: 81

Asp Tyr Lys Asp Asp Asp Asp Lys
 1               5

<210> SEQ ID NO 82
<211> LENGTH: 39
<212> TYPE: DNA
<213> ORGANISM: Artificial Sequence
<220> FEATURE:
<223> OTHER INFORMATION: A synthetic T7 translation initiation sequence.

<400> SEQUENCE: 82
tctagaaata attttgttta actttaagaa ggagatata                             39

<210> SEQ ID NO 83
<211> LENGTH: 12
<212> TYPE: PRT
<213> ORGANISM: Artificial Sequence
<220> FEATURE:
<223> OTHER INFORMATION: A synthetic T7 tag sequence.

<400> SEQUENCE: 83

Met Ala Ser Met Thr Gly Gly Gln Gln Met Gly Arg
 1               5                  10

<210> SEQ ID NO 84

```
<211> LENGTH: 42
<212> TYPE: DNA
<213> ORGANISM: Artificial Sequence
<220> FEATURE:
<223> OTHER INFORMATION: A synthetic T7 tag sequence.

<400> SEQUENCE: 84
atggctagca tgactggtgg acagcaaatg ggtcgcggat cc              42

<210> SEQ ID NO 85
<211> LENGTH: 34
<212> TYPE: DNA
<213> ORGANISM: Artificial Sequence
<220> FEATURE:
<223> OTHER INFORMATION: A synthetic primer.

<400> SEQUENCE: 85
tgcatttcta gaattgtgaa ttgttatccg ctca                       34

<210> SEQ ID NO 86
<211> LENGTH: 34
<212> TYPE: DNA
<213> ORGANISM: Artificial Sequence
<220> FEATURE:
<223> OTHER INFORMATION: A synthetic primer.

<400> SEQUENCE: 86
tgcatttcta gaattgtgaa ttgttatccg ctca                       34

<210> SEQ ID NO 87
<211> LENGTH: 261
<212> TYPE: DNA
<213> ORGANISM: Artificial Sequence
<220> FEATURE:
<223> OTHER INFORMATION: A synthetic PCR product.

<400> SEQUENCE: 87
tcaaagatct tatcgactgc acggtgcacc aatgcttctg gcgtcaggca gccatcggaa    60
gctgtggtat ggctgtgcag gtcgtaaatc actgcataat tcgtgtcgct caaggcgcac  120
tcccgttctg gataatgttt tttgcgccga catcataacg gttctggcaa atattctgaa  180
atgagctgtt gacaattaat catcggctcg tataatgtgt ggaattgtga gcggataaca  240
attcacaatt ctagaaatgc a                                            261

<210> SEQ ID NO 88
<211> LENGTH: 30
<212> TYPE: DNA
<213> ORGANISM: Artificial Sequence
<220> FEATURE:
<223> OTHER INFORMATION: A synthetic primer.

<400> SEQUENCE: 88
ccgctcgagt tatgccagac gagcacgagc                            30

<210> SEQ ID NO 89
<211> LENGTH: 54
<212> TYPE: DNA
<213> ORGANISM: Artificial Sequence
<220> FEATURE:
<223> OTHER INFORMATION: A synthetic primer.

<400> SEQUENCE: 89
gctatggtcg acgacgacga caaatgccac tacgctgacg ctatcttcac caac          54
```

```
<210> SEQ ID NO 90
<211> LENGTH: 54
<212> TYPE: DNA
<213> ORGANISM: Artificial Sequence
<220> FEATURE:
<223> OTHER INFORMATION: A synthetic primer.

<400> SEQUENCE: 90
cgcggatccg gccagggtca ggctcaatat ctggcggcct ccctggttgt gttc        54

<210> SEQ ID NO 91
<211> LENGTH: 36
<212> TYPE: DNA
<213> ORGANISM: Artificial Sequence
<220> FEATURE:
<223> OTHER INFORMATION: A synthetic primer.

<400> SEQUENCE: 91
gagctcgagt tatgccagac gagcacgagc accacg                            36

<210> SEQ ID NO 92
<211> LENGTH: 8
<212> TYPE: PRT
<213> ORGANISM: Artificial Sequence
<220> FEATURE:
<223> OTHER INFORMATION: A synthetic hydrophobic core sequence.

<400> SEQUENCE: 92

Leu Ala Ala Ser Leu Val Val Phe
1               5

<210> SEQ ID NO 93
<211> LENGTH: 66
<212> TYPE: DNA
<213> ORGANISM: Artificial Sequence
<220> FEATURE:
<223> OTHER INFORMATION: A synthetic primer.

<400> SEQUENCE: 93
cgcggatccg gccagggtca ggctcaatat gacgaagctt ccgacgttga attcaccaac  60
tactcg                                                             66

<210> SEQ ID NO 94
<211> LENGTH: 19
<212> TYPE: DNA
<213> ORGANISM: Artificial Sequence
<220> FEATURE:
<223> OTHER INFORMATION: A synthetic primer.

<400> SEQUENCE: 94
tcagtcacga tgaattccc                                               19

<210> SEQ ID NO 95
<211> LENGTH: 45
<212> TYPE: DNA
<213> ORGANISM: Artificial Sequence
<220> FEATURE:
<223> OTHER INFORMATION: A synthetic primer.
<220> FEATURE:
<221> NAME/KEY: misc_feature
<222> LOCATION: 30
<223> OTHER INFORMATION: n = a or t or g or c.

<400> SEQUENCE: 95
gatccggcca gggtcaggct caatatctgn cggcctccct ggttm                  45
```

```
<210> SEQ ID NO 96
<211> LENGTH: 45
<212> TYPE: DNA
<213> ORGANISM: Artificial Sequence
<220> FEATURE:
<223> OTHER INFORMATION: A synthetic primer.
<220> FEATURE:
<221> NAME/KEY: misc_feature
<222> LOCATION: 20
<223> OTHER INFORMATION: n = a or t or g or c.

<400> SEQUENCE: 96
aattkaacca gggaggcagn cagatattga gcctgaccct ggccg          45

<210> SEQ ID NO 97
<211> LENGTH: 8
<212> TYPE: PRT
<213> ORGANISM: Artificial Sequence
<220> FEATURE:
<223> OTHER INFORMATION: A synthetic modified hydrophobic core sequence.

<400> SEQUENCE: 97

Leu Ala Ala Ser Leu Val Gln Phe
1               5

<210> SEQ ID NO 98
<211> LENGTH: 8
<212> TYPE: PRT
<213> ORGANISM: Artificial Sequence
<220> FEATURE:
<223> OTHER INFORMATION: A synthetic modified hydrophobic core sequence.

<400> SEQUENCE: 98

Leu Ser Ala Ser Leu Val Gln Phe
1               5

<210> SEQ ID NO 99
<211> LENGTH: 8
<212> TYPE: PRT
<213> ORGANISM: Artificial Sequence
<220> FEATURE:
<223> OTHER INFORMATION: A synthetic modified hydrophobic core sequence.

<400> SEQUENCE: 99

Leu Thr Ala Ser Leu Val Lys Phe
1               5

<210> SEQ ID NO 100
<211> LENGTH: 40
<212> TYPE: DNA
<213> ORGANISM: Artificial Sequence
<220> FEATURE:
<223> OTHER INFORMATION: A synthetic primer.

<400> SEQUENCE: 100
accgctcgag gatatcttag aagttgtgaa cgtcctgcag          40

<210> SEQ ID NO 101
<211> LENGTH: 49
<212> TYPE: DNA
<213> ORGANISM: Artificial Sequence
<220> FEATURE:
<223> OTHER INFORMATION: A synthetic primer.

<400> SEQUENCE: 101
cagcgttaac ccggaattct ctgttggtgg tggtggtggt ccgcgttct          49
```

-continued

```
<210> SEQ ID NO 102
<211> LENGTH: 57
<212> TYPE: DNA
<213> ORGANISM: Artificial Sequence
<220> FEATURE:
<223> OTHER INFORMATION: A synthetic primer.

<400> SEQUENCE: 102
ccggaattct ctgttggtgg tggtggtggt ccgcgttgcc actctgtttc tgaaatc      57

<210> SEQ ID NO 103
<211> LENGTH: 51
<212> TYPE: DNA
<213> ORGANISM: Artificial Sequence
<220> FEATURE:
<223> OTHER INFORMATION: A synthetic primer.

<400> SEQUENCE: 103
ctcggatccc aatatctggc tgccgtgctg gttgtgttca ccaactactc g            51

<210> SEQ ID NO 104
<211> LENGTH: 5
<212> TYPE: PRT
<213> ORGANISM: Artificial Sequence
<220> FEATURE:
<223> OTHER INFORMATION: A synthetic deleted portion of the VG leader
      sequence.

<400> SEQUENCE: 104

Gly Gln Gly Gln Ala
 1               5

<210> SEQ ID NO 105
<211> LENGTH: 8
<212> TYPE: PRT
<213> ORGANISM: Artificial Sequence
<220> FEATURE:
<223> OTHER INFORMATION: A synthetic modified Vg hydrophobic sequence.

<400> SEQUENCE: 105

Leu Ala Ala Val Leu Val Val Phe
 1               5

<210> SEQ ID NO 106
<211> LENGTH: 6
<212> TYPE: PRT
<213> ORGANISM: Artificial Sequence
<220> FEATURE:
<223> OTHER INFORMATION: A synthetic deleted portion of the VG sequence.

<400> SEQUENCE: 106

Thr Ala Ser Gln Val Asp
 1               5

<210> SEQ ID NO 107
<211> LENGTH: 33
<212> TYPE: DNA
<213> ORGANISM: Artificial Sequence
<220> FEATURE:
<223> OTHER INFORMATION: A synthetic primer.

<400> SEQUENCE: 107
gacgttaacg tcgcccgagt agttggtgaa cac                                33

<210> SEQ ID NO 108
<211> LENGTH: 19
<212> TYPE: DNA
```

```
<213> ORGANISM: Artificial Sequence
<220> FEATURE:
<223> OTHER INFORMATION: A synthetic primer.

<400> SEQUENCE: 108
gagcggataa caattcaca                                                19

<210> SEQ ID NO 109
<211> LENGTH: 5
<212> TYPE: PRT
<213> ORGANISM: Artificial Sequence
<220> FEATURE:
<223> OTHER INFORMATION: A synthetic deleted sequence.

<400> SEQUENCE: 109

Pro Glu Phe Ser Val
 1               5

<210> SEQ ID NO 110
<211> LENGTH: 45
<212> TYPE: DNA
<213> ORGANISM: Artificial Sequence
<220> FEATURE:
<223> OTHER INFORMATION: A synthetic primer.

<400> SEQUENCE: 110
gacgttaacg gtggtggtgg tggttgccac tctgtttctg aaatc               45

<210> SEQ ID NO 111
<211> LENGTH: 22
<212> TYPE: DNA
<213> ORGANISM: Artificial Sequence
<220> FEATURE:
<223> OTHER INFORMATION: A synthetic primer.

<400> SEQUENCE: 111
tgctagttat tgctcagcgg tg                                        22

<210> SEQ ID NO 112
<211> LENGTH: 27
<212> TYPE: DNA
<213> ORGANISM: Artificial Sequence
<220> FEATURE:
<223> OTHER INFORMATION: A synthetic primer.

<400> SEQUENCE: 112
ggtgctagca tggagaaaaa aatcact                                   27

<210> SEQ ID NO 113
<211> LENGTH: 21
<212> TYPE: DNA
<213> ORGANISM: Artificial Sequence
<220> FEATURE:
<223> OTHER INFORMATION: A synthetic primer.

<400> SEQUENCE: 113
atcctcgagc tgccaagggt t                                         21

<210> SEQ ID NO 114
<211> LENGTH: 30
<212> TYPE: DNA
<213> ORGANISM: Artificial Sequence
<220> FEATURE:
<223> OTHER INFORMATION: A synthetic primer.

<400> SEQUENCE: 114
```

```
atcgctagcg ttaacgtcca cctggctggc                                    30
```

<210> SEQ ID NO 115
<211> LENGTH: 29
<212> TYPE: DNA
<213> ORGANISM: Artificial Sequence
<220> FEATURE:
<223> OTHER INFORMATION: A synthetic primer.

<400> SEQUENCE: 115

```
cccgggtcga caactttaag aaggagata                                     29
```

<210> SEQ ID NO 116
<211> LENGTH: 39
<212> TYPE: DNA
<213> ORGANISM: Artificial Sequence
<220> FEATURE:
<223> OTHER INFORMATION: A synthetic primer.

<400> SEQUENCE: 116

```
atggctagca tagatcccgt cgttttacaa cgtcgtgac                          39
```

<210> SEQ ID NO 117
<211> LENGTH: 39
<212> TYPE: DNA
<213> ORGANISM: Artificial Sequence
<220> FEATURE:
<223> OTHER INFORMATION: A synthetic primer.

<400> SEQUENCE: 117

```
cggctcgagt tattattttt gacaccagac caactggta                          39
```

<210> SEQ ID NO 118
<211> LENGTH: 54
<212> TYPE: DNA
<213> ORGANISM: Artificial Sequence
<220> FEATURE:
<223> OTHER INFORMATION: A synthetic primer.

<400> SEQUENCE: 118

```
gctatggtcg acgacgacga caaatgccac catgctgaag gtaccttcac ctcc         54
```

<210> SEQ ID NO 119
<211> LENGTH: 48
<212> TYPE: DNA
<213> ORGANISM: Artificial Sequence
<220> FEATURE:
<223> OTHER INFORMATION: A synthetic primer.

<400> SEQUENCE: 119

```
atgcatctcg agttagtggc aacgaccttt aaccagccaa gcgatgaa                48
```

<210> SEQ ID NO 120
<211> LENGTH: 101
<212> TYPE: PRT
<213> ORGANISM: Artificial Sequence
<220> FEATURE:
<223> OTHER INFORMATION: A synthetic sequence for the T7tagVgCH-GRF
      (1-44)A cassette.

<400> SEQUENCE: 120

```
Met Ala Ser Met Thr Gly Gly Gln Gln Met Gly Arg Gly Ser Gly Gln
 1               5                  10                  15

Gly Gln Ala Gln Tyr Leu Ala Ala Ser Leu Val Val Phe Thr Asn Tyr
            20                  25                  30
```

```
Ser Gly Asp Thr Ala Ser Gln Val Asp Val Asn Gly Pro Arg Ala Met
        35                  40                  45

Val Asp Asp Asp Lys Cys His Tyr Ala Asp Ala Ile Phe Thr Asn
 50                  55                  60

Ser Tyr Arg Lys Val Leu Gly Gln Leu Ser Ala Arg Lys Leu Leu Gln
 65                  70                  75                  80

Asp Ile Met Ser Arg Gln Gln Gly Glu Ser Asn Gln Glu Arg Gly Ala
                 85                  90                  95

Arg Ala Arg Leu Ala
             100

<210> SEQ ID NO 121
<211> LENGTH: 312
<212> TYPE: DNA
<213> ORGANISM: Artificial Sequence
<220> FEATURE:
<223> OTHER INFORMATION: A synthetic sequence for the T7tagVgCH-GRF
      (1-44)A cassette.

<400> SEQUENCE: 121
atggctagca tgactggtgg acagcaaatg ggtcgcggat ccggccaggg acaggctcaa      60
tatctagcgg cctccttggt tgtgttcacc aactactcgg gcgacacggc cagccaggtg     120
gacgttaacg gtccgcgtgc tatggtcgac gacgacgaca atgccacta cgctgacgct     180 atcttcacca actcttaccg taaagttctg ggtcagctgt ctgctcgtaa actgctgcag     240
gacatcatgt cccgtcagca gggtgaatct aaccaggaac gtggtgctcg tgctcgtctg     300
gcataactcg ag                                                         312

<210> SEQ ID NO 122
<211> LENGTH: 76
<212> TYPE: PRT
<213> ORGANISM: Artificial Sequence
<220> FEATURE:
<223> OTHER INFORMATION: A synthetic sequence for the T7tag-GRF(1-44)A
      cassette.

<400> SEQUENCE: 122

Met Ala Ser Met Thr Gly Gly Gln Gln Met Gly Arg Gly Ser Glu Phe
 1               5                  10                  15

Ser Phe Val Asn Gly Pro Arg Ala Met Val Asp Asp Asp Lys Tyr
             20                  25                  30

Ala Asp Ala Ile Phe Thr Asn Ser Tyr Arg Lys Val Leu Gly Gln Leu
                 35                  40                  45

Ser Ala Arg Lys Leu Leu Gln Asp Ile Met Ser Arg Gln Gln Gly Glu
 50                  55                  60

Ser Asn Gln Glu Arg Gly Ala Arg Ala Arg Leu Ala
 65                  70                  75

<210> SEQ ID NO 123
<211> LENGTH: 258
<212> TYPE: DNA
<213> ORGANISM: Artificial Sequence
<220> FEATURE:
<223> OTHER INFORMATION: A synthetic sequence for the T7tag-GRF(1-44)A
      cassette.

<400> SEQUENCE: 123
atggctagca tgactggtgg acagcaaatg ggtcgcggat ccgaattctc cttcgttaac      60
ggtccgcgtg ctatggtcga cgacgacgac cactacgctg acgctatctt caccaactct     120
```

```
taccgtaaag ttctgggtca gctgtctgct cgtaaactgc tgcaggacat catgtcccgt    180
cagcagggtg aatctaacca ggaacgtggt gctcgtgctc gtctggcata agatgacaag    240
cttgcggccg cactcgag                                                  258
```

```
<210> SEQ ID NO 124
<211> LENGTH: 99
<212> TYPE: PRT
<213> ORGANISM: Artificial Sequence
<220> FEATURE:
<223> OTHER INFORMATION: A synthetic sequence for the T7tagVg-GRF(1-44)A
      cassette.

<400> SEQUENCE: 124
```

```
Met Ala Ser Met Thr Gly Gly Gln Gln Met Gly Arg Gly Ser Gly Gln
 1               5                  10                  15

Gly Gln Ala Gln Tyr Leu Ala Ala Ser Leu Val Val Phe Thr Asn Tyr
            20                  25                  30

Ser Gly Asp Thr Ala Ser Gln Val Asp Val Asn Gly Pro Arg Ala Met
        35                  40                  45

Val Asp Asp Asp Lys Tyr Ala Asp Ala Ile Phe Thr Asn Ser Tyr
50                  55                  60

Arg Lys Val Leu Gly Gln Leu Ser Ala Arg Lys Leu Leu Gln Asp Ile
65                  70                  75                  80

Met Ser Arg Gln Gln Gly Glu Ser Asn Gln Glu Arg Gly Ala Arg Ala
                85                  90                  95

Arg Leu Ala
```

```
<210> SEQ ID NO 125
<211> LENGTH: 327
<212> TYPE: DNA
<213> ORGANISM: Artificial Sequence
<220> FEATURE:
<223> OTHER INFORMATION: A synthetic sequence for the T7tagVg-GRF(1-44)A
      cassette.

<400> SEQUENCE: 125
atggctagca tgactggtgg acagcaaatg ggtcgcggat ccggccaggg acaggctcaa    60
tatctagcgg cctccttggt tgtgttcacc aactactcgg gcgacacggc cagccaggtg   120
gacgttaacg gtccgcgtgc tatggtcgac gacgacgaca aatacgctga cgctatcttc   180
accaactctt accgtaaagt tctgggtcag ctgtctgctc gtaaactgct gcaggacatc   240
atgtcccgtc agcagggtga atctaaccag gaacgtggtg ctcgtgctcg tctggcataa   300
gatgacaagc ttgcggccgc actcgag                                       327
```

```
<210> SEQ ID NO 126
<211> LENGTH: 103
<212> TYPE: PRT
<213> ORGANISM: Artificial Sequence
<220> FEATURE:
<223> OTHER INFORMATION: A synthetic sequence for the T7tagVg(opt)CH-GRF
      (1-44)A cassette.

<400> SEQUENCE: 126
```

```
Met Ala Ser Met Thr Gly Gly Gln Gln Met Gly Arg Gly Ser Gly Gln
 1               5                  10                  15

Gly Gln Ala Gln Tyr Leu Ala Ala Ser Leu Val Val Phe Thr Asn Tyr
            20                  25                  30

Ser Gly Asp Thr Ala Ser Gln Val Asp Val Asn Gly Pro Arg Ala Met
        35                  40                  45
```

```
Val Asp Asp Asp Lys Cys His Tyr Ala Asp Ala Ile Phe Thr Asn
 50                  55                  60

Ser Tyr Arg Lys Val Leu Gly Gln Leu Ser Ala Arg Lys Leu Leu Gln
 65                  70                  75                  80

Asp Ile Met Ser Arg Gln Gln Gly Glu Ser Asn Gln Glu Arg Gly Ala
                 85                  90                  95

Arg Ala Arg Leu Ala Leu Glu
            100

<210> SEQ ID NO 127
<211> LENGTH: 312
<212> TYPE: DNA
<213> ORGANISM: Artificial Sequence
<220> FEATURE:
<223> OTHER INFORMATION: A synthetic sequence for the T7tagVg(opt)CH-GRF
      (1-44)A cassette.

<400> SEQUENCE: 127
atggctagca tgactggtgg acagcaaatg ggtcgcggat ccggccaggg tcaggctcaa    60
tatctggcgg cctccctggt tgtgttcacc aactactcgg gcgacacggc cagccaggtg   120
gacgttaacg gtccgcgtgc tatggtcgac gacgacgaca aatgccacta cgctgacgct   180
atcttcacca actcttaccg taaagttctg ggtcagctgt ctgctcgtaa actgctgcag   240
gacatcatgt cccgtcagca gggtgaatct aaccaggaac gtggtgctcg tgctcgtctg   300
gcataactcg ag                                                      312

<210> SEQ ID NO 128
<211> LENGTH: 103
<212> TYPE: PRT
<213> ORGANISM: Artificial Sequence
<220> FEATURE:
<223> OTHER INFORMATION: A synthetic sequence for the T7tagVgMut1CH-GRF
      (1-44)A cassette.

<400> SEQUENCE: 128

Met Ala Ser Met Thr Gly Gly Gln Gln Met Gly Arg Gly Ser Gly Gln
  1               5                  10                  15

Gly Gln Ala Gln Tyr Asp Glu Ala Ser Asp Val Glu Phe Thr Asn Tyr
                 20                  25                  30

Ser Gly Asp Thr Ala Ser Gln Val Asp Val Asn Gly Pro Arg Ala Met
                 35                  40                  45

Val Asp Asp Asp Lys Cys His Tyr Ala Asp Ala Ile Phe Thr Asn
 50                  55                  60

Ser Tyr Arg Lys Val Leu Gly Gln Leu Ser Ala Arg Lys Leu Leu Gln
 65                  70                  75                  80

Asp Ile Met Ser Arg Gln Gln Gly Glu Ser Asn Gln Glu Arg Gly Ala
                 85                  90                  95

Arg Ala Arg Leu Ala Leu Glu
            100

<210> SEQ ID NO 129
<211> LENGTH: 312
<212> TYPE: DNA
<213> ORGANISM: Artificial Sequence
<220> FEATURE:
<223> OTHER INFORMATION: A synthetic sequence for the T7tagVgMut1CH-GRF
      (1-44)A cassette.

<400> SEQUENCE: 129
```

```
atggctagca tgactggtgg acagcaaatg gtcgcggat ccggccaggg tcaggctcaa    60
tatgacgaag cttccgacgt tgaattcacc aactactcgg gcgacacggc cagccaggtg   120
gacgttaacg gtccgcgtgc tatggtcgac gacgacgaca aatgccacta cgctgacgct   180
atcttcacca actcttaccg taaagttctg ggtcagctgt ctgctcgtaa actgctgcag   240
gacatcatgt cccgtcagca gggtgaatct aaccaggaac gtggtgctcg tgctcgtctg   300
gcataactcg ag                                                      312
```

<210> SEQ ID NO 130
<211> LENGTH: 103
<212> TYPE: PRT
<213> ORGANISM: Artificial Sequence
<220> FEATURE:
<223> OTHER INFORMATION: A synthetic sequence for the T7tagVgMut4CH-GRF
      (1-44)A cassette.
<220> FEATURE:
<221> NAME/KEY: SITE
<222> LOCATION: 23
<223> OTHER INFORMATION: Xaa = Thr or Pro or Ala or Ser.
<220> FEATURE:
<221> NAME/KEY: SITE
<222> LOCATION: 28
<223> OTHER INFORMATION: Xaa = Lys or Gln.

<400> SEQUENCE: 130

```
Met Ala Ser Met Thr Gly Gly Gln Gln Met Gly Arg Gly Ser Gly Gln
 1               5                  10                  15

Gly Gln Ala Gln Tyr Leu Xaa Ala Ser Leu Val Xaa Phe Thr Asn Tyr
            20                  25                  30

Ser Gly Asp Thr Ala Ser Gln Val Asp Val Asn Gly Pro Arg Ala Met
        35                  40                  45

Val Asp Asp Asp Asp Lys Cys His Tyr Ala Asp Ala Ile Phe Thr Asn
 50                  55                  60

Ser Tyr Arg Lys Val Leu Gly Gln Leu Ser Ala Arg Lys Leu Leu Gln
 65                  70                  75                  80

Asp Ile Met Ser Arg Gln Gln Gly Glu Ser Asn Gln Glu Arg Gly Ala
                85                  90                  95

Arg Ala Arg Leu Ala Leu Glu
            100
```

<210> SEQ ID NO 131
<211> LENGTH: 312
<212> TYPE: DNA
<213> ORGANISM: Artificial Sequence
<220> FEATURE:
<223> OTHER INFORMATION: A synthetic sequence for the T7tagVgMut4CH-GRF
      (1-44)A cassette.
<220> FEATURE:
<221> NAME/KEY: misc_structure
<222> LOCATION: 67
<223> OTHER INFORMATION: n = a or t or g or c.

<400> SEQUENCE: 131

```
atggctagca tgactggtgg acagcaaatg gtcgcggat ccggccaggg tcaggctcaa    60
tatctgncgg cctccctggt tmaattcacc aactactcgg gcgacacggc cagccaggtg   120
gacgttaacg gtccgcgtgc tatggtcgac gacgacgaca aatgccacta cgctgacgct   180
atcttcacca actcttaccg taaagttctg ggtcagctgt ctgctcgtaa actgctgcag   240
gacatcatgt cccgtcagca gggtgaatct aaccaggaac gtggtgctcg tgctcgtctg   300
gcataactcg ag                                                      312
```

<210> SEQ ID NO 132
<211> LENGTH: 89
<212> TYPE: PRT
<213> ORGANISM: Artificial Sequence
<220> FEATURE:
<223> OTHER INFORMATION: A synthetic sequence for the T7tagVg-PTH(1-34) cassette.

<400> SEQUENCE: 132

Met Ala Ser Met Thr Gly Gly Gln Gln Met Gly Arg Gly Ser Gly Gln
1               5                   10                  15

Gly Gln Ala Gln Tyr Leu Ala Ala Ser Leu Val Val Phe Thr Asn Tyr
            20                  25                  30

Ser Gly Asp Thr Ala Ser Gln Val Asp Val Asn Pro Glu Phe Ser Val
        35                  40                  45

Gly Gly Gly Gly Pro Arg Ser Val Ser Glu Ile Gln Leu Met His
50                  55                  60

Asn Leu Gly Lys His Leu Asn Ser Met Glu Arg Val Glu Trp Leu Arg
65                  70                  75                  80

Lys Lys Leu Gln Asp Val His Asn Phe
                85

<210> SEQ ID NO 133
<211> LENGTH: 282
<212> TYPE: DNA
<213> ORGANISM: Artificial Sequence
<220> FEATURE:
<223> OTHER INFORMATION: A synthetic sequence for the T7tagVg-PTH(1-34) cassette.

<400> SEQUENCE: 133
atggctagca tgactggtgg acagcaaatg ggtcgcggat ccggccaggg tcaggctcaa      60
tatctggctg cctccctggt tgtgttcacc aactactcgg gcgacacggc cagccaggtg     120
gacgttaacc cggaattctc tgttggtggt ggtggtggtc cgcgttctgt ttctgaaatc     180
cagctgatgc acaacctggg taaacacctg aactctatgg aacgtgttga atggctgcgt     240
aaaaaactgc aggacgttca caacttctaa gatatcctcg ag                       282

<210> SEQ ID NO 134
<211> LENGTH: 19
<212> TYPE: PRT
<213> ORGANISM: Artificial Sequence
<220> FEATURE:
<223> OTHER INFORMATION: A synthetic sequence for a linker sequence containing a paladium cleavage site.

<400> SEQUENCE: 134

Val Asn Pro Glu Phe Ser Val Gly Gly Gly Gly Gly Pro Arg Cys His
1               5                   10                  15

Ser Val Ser

<210> SEQ ID NO 135
<211> LENGTH: 57
<212> TYPE: DNA
<213> ORGANISM: Artificial Sequence
<220> FEATURE:
<223> OTHER INFORMATION: A synthetic sequence for a linker sequence containing a paladium cleavage site.

<400> SEQUENCE: 135
gttaacccgg aattctctgt tggtggtggt ggtggtccgc gttgccactc tgtttct       57

<210> SEQ ID NO 136
<211> LENGTH: 50
<212> TYPE: PRT
<213> ORGANISM: Artificial Sequence
<220> FEATURE:
<223> OTHER INFORMATION: A synthetic Del 3 leader sequence.

<400> SEQUENCE: 136

```
Met Ala Ser Met Thr Gly Gly Gln Gln Met Gly Arg Gly Ser Gly Gln
1               5                   10                  15

Gly Gln Ala Gln Tyr Leu Ala Ala Ser Leu Val Val Phe Thr Asn Tyr
            20                  25                  30

Ser Gly Asp Thr Ala Ser Gln Val Asp Val Asn Gly Gly Gly Gly
        35                  40                  45

Cys His
    50
```

<210> SEQ ID NO 137
<211> LENGTH: 150
<212> TYPE: DNA
<213> ORGANISM: Artificial Sequence
<220> FEATURE:
<223> OTHER INFORMATION: A synthetic Del 3 leader sequence.

<400> SEQUENCE: 137

```
atggctagca tgactggtgg acagcaaatg ggtcgcggat ccggccaggg tcaggctcaa    60
tatctggctg cctccctggt tgtgttcacc aactactcgg gcgacacggc cagccaggtg   120
gacgttaacg gtggtggtgg tggttgccac                                    150
```

<210> SEQ ID NO 138
<211> LENGTH: 44
<212> TYPE: PRT
<213> ORGANISM: Artificial Sequence
<220> FEATURE:
<223> OTHER INFORMATION: A synthetic Del 2 and 3 leader sequence.

<400> SEQUENCE: 138

```
Met Ala Ser Met Thr Gly Gly Gln Gln Met Gly Arg Gly Ser Gly Gln
1               5                   10                  15

Gly Gln Ala Gln Tyr Leu Ala Ala Ser Leu Val Val Phe Thr Asn Tyr
            20                  25                  30

Ser Gly Asp Val Asn Gly Gly Gly Gly Gly Cys His
        35                  40
```

<210> SEQ ID NO 139
<211> LENGTH: 132
<212> TYPE: DNA
<213> ORGANISM: Artificial Sequence
<220> FEATURE:
<223> OTHER INFORMATION: A synthetic Del 2 and 3 leader sequence.

<400> SEQUENCE: 139

```
atggctagca tgactggtgg acagcaaatg ggtcgcggat ccggccaggg tcaggctcaa    60
tatctggctg cctccctggt tgtgttcacc aactactcgg gcgacgttaa cggtggtggt   120
ggtggttgcc ac                                                       132
```

<210> SEQ ID NO 140
<211> LENGTH: 34
<212> TYPE: PRT
<213> ORGANISM: Artificial Sequence
<220> FEATURE:

<223> OTHER INFORMATION: A synthetic PTH sequence.

<400> SEQUENCE: 140

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 141
<211> LENGTH: 117
<212> TYPE: DNA
<213> ORGANISM: Artificial Sequence
<220> FEATURE:
<223> OTHER INFORMATION: A synthetic PTH sequence.

<400> SEQUENCE: 141
tctgtttctg aaatccagct gatgcacaac ctgggtaaac acctgaactc tatggaacgt      60
gttgaatggc tgcgtaaaaa actgcaggac gttcacaact tctaagatat cctcgag       117

<210> SEQ ID NO 142
<211> LENGTH: 46
<212> TYPE: PRT
<213> ORGANISM: Artificial Sequence
<220> FEATURE:
<223> OTHER INFORMATION: A synthetic sequence for a NheI-releaseable
      T7Vg fragment.

<400> SEQUENCE: 142

Met Ala Ser Met Thr Gly Gly Gln Gln Met Gly Arg Gly Ser Gly Gln
1               5                   10                  15

Gly Gln Ala Gln Tyr Leu Ala Ala Ser Leu Val Val Phe Thr Asn Tyr
            20                  25                  30

Ser Gly Asp Thr Ala Ser Gln Val Asp Val Asn Ala Ser Asp
        35                  40                  45

<210> SEQ ID NO 143
<211> LENGTH: 138
<212> TYPE: DNA
<213> ORGANISM: Artificial Sequence
<220> FEATURE:
<223> OTHER INFORMATION: A synthetic sequence for a NheI-releaseable
      T7Vg fragment.

<400> SEQUENCE: 143
atggctagca tgactggtgg acagcaaatg ggtcgcggat ccggccaggg tcaggctcaa      60
tatctggctg cctccctggt tgtgttcacc aactactcgg gcgacacggc cagccaggtg    120
gacgttaacg ctagcgat                                                  138

<210> SEQ ID NO 144
<211> LENGTH: 88
<212> TYPE: PRT
<213> ORGANISM: Artificial Sequence
<220> FEATURE:
<223> OTHER INFORMATION: A synthetic sequence of a T7tagVgCH-GLP-1(7-36)
      CH cassette.

<400> SEQUENCE: 144

Met Ala Ser Met Thr Gly Gly Gln Gln Met Gly Arg Gly Ser Gly Gln
1               5                   10                  15

Gly Gln Ala Gln Tyr Leu Ala Ala Ser Leu Val Val Phe Thr Asn Tyr
            20                  25                  30

Ser Gly Asp Thr Ala Ser Gln Val Asp Val Asn Gly Pro Arg Ala Met
    35                  40                  45

Val Asp Asp Asp Lys Cys His His Ala Glu Gly Thr Phe Thr Ser
 50                  55                  60

Asp Val Ser Ser Tyr Leu Glu Gly Gln Ala Ala Lys Glu Phe Ile Ala
 65                  70                  75                  80

Trp Leu Val Lys Gly Arg Cys His
                85

<210> SEQ ID NO 145
<211> LENGTH: 273
<212> TYPE: DNA
<213> ORGANISM: Artificial Sequence
<220> FEATURE:
<223> OTHER INFORMATION: A synthetic sequence of a T7tagVgCH-GLP-1(7-36)
      CH cassette.

<400> SEQUENCE: 145
atggctagca tgactggtgg acagcaaatg ggtcgcggat ccggccaggg tcaggctcaa     60
tatctggcgg cctccctggt tgtgttcacc aactactcgg gcgacacggc cagccaggtg    120
gacgttaacg gtccgcgtgc tatggtcgac gacgacgaca atgccacca tgctgaaggt    180 accttcacct ccgacgtttc ctcctacctg gaaggtcagg ctgctaaaga attcatcgct    240
tggctggtta aaggtcgttg ccactaactc gag                                 273

<210> SEQ ID NO 146
<211> LENGTH: 15
<212> TYPE: PRT
<213> ORGANISM: Artificial Sequence
<220> FEATURE:
<223> OTHER INFORMATION: A synthetic linker.

<400> SEQUENCE: 146

Val Asn Gly Pro Arg Ala Met Val Asp Asp Asp Lys Cys His
 1               5                  10                  15

<210> SEQ ID NO 147
<211> LENGTH: 59
<212> TYPE: DNA
<213> ORGANISM: Artificial Sequence
<220> FEATURE:
<223> OTHER INFORMATION: A synthetic primer.

<400> SEQUENCE: 147
ccgcggatcc ggccagggac aggctcaata tctatgggcc tccttggttg tgttcacca     59

<210> SEQ ID NO 148
<211> LENGTH: 60
<212> TYPE: DNA
<213> ORGANISM: Artificial Sequence
<220> FEATURE:
<223> OTHER INFORMATION: A synthetic primer.

<400> SEQUENCE: 148
cgcgttaacg tccaacctgg ctggccgtgt cgcccgagta gttggtgaac acaaccaagg    60

<210> SEQ ID NO 149
<211> LENGTH: 6
<212> TYPE: PRT
<213> ORGANISM: Artificial Sequence
<220> FEATURE:
<223> OTHER INFORMATION: Prostate specific antigen preferred cleavage
      sequence.

```
<220> FEATURE:
<221> NAME/KEY: SITE
<222> LOCATION: 3
<223> OTHER INFORMATION: Xaa = Tyr or Phe.
<220> FEATURE:
<221> NAME/KEY: SITE
<222> LOCATION: 6
<223> OTHER INFORMATION: Xaa = Gly or Ser.

<400> SEQUENCE: 149

Ser Ser Xaa Tyr Ser Xaa
  1               5
```